(12) United States Patent
Song et al.

(10) Patent No.: US 8,329,619 B2
(45) Date of Patent: Dec. 11, 2012

(54) SUBSTITUTED QUINOLINONES HAVING HERBICIDAL ACTION

(75) Inventors: Dschun Song, Mannheim (DE); Julia Major, Mannheim (DE); Johannes Hutzler, Waldsee (DE); Trevor William Newton, Neustadt (DE); Matthias Witschel, Bad Duerkheim (DE); William Karl Moberg, Neustadt (DE); Liliana Parra Rapado, Offenburg (DE); Tao Qu, Ludwigshafen (DE); Frank Stelzer, Mannheim (DE); Andree Van Der Kloet, Heidelberg (DE); Thomas Seitz, Viernheim (DE); Thomas Ehrhardt, Speyer (DE); Klaus Kreuz, Denzlingen (DE); Klaus Grossmann, Neuhofen (DE); Anna Aleksandra Michrowska, Mannheim (DE); Anja Simon, Weinheim (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/915,608

(22) Filed: Oct. 29, 2010

(65) Prior Publication Data

US 2011/0105329 A1    May 5, 2011

(30) Foreign Application Priority Data

Nov. 3, 2009 (EP) ..................... 09174833

(51) Int. Cl.
*A01N 43/42* (2006.01)
*A61K 31/47* (2006.01)
*C07D 215/00* (2006.01)

(52) U.S. Cl. ........ 504/247; 514/311; 514/315; 546/152; 546/153

(58) Field of Classification Search .................. 504/247; 514/311, 312; 546/152, 153
See application file for complete search history.

(56) References Cited

FOREIGN PATENT DOCUMENTS

WO  WO 2008/009908  1/2008
WO  WO 2008/071918  6/2008

OTHER PUBLICATIONS

Eistert B., et al., "Ringerweiterung von 1.1-Dimethyl-indandion-(2.3)", Chem. Ber. (1969) 102, 2429-2439.
Gomtsyan, A. et al. "Identification of (R)-1-(5-tert-butyl-2,3-dihydro-1H-inden-1-yl)-3-(1H-indazol-4-yl)urea (ABT-102) as a potent TRPV1 antagonist for pain management", J. Med. Chem. (2008) 51, 392-395.
Petrovskaia, O. et al., "ChemInform Abstract: Investigations of the reaction mechanisms of 1,2-indandiones with amino acids", J. Org. Chem. (2001) 66, 7666-7675.
Thummel, R. et al., "Polyaza Cavity-shaped Molecules. Annelated Derivatives of 2-(2'-pyridyl)-1,8-naphthyridine and 2,2'-Bi-1,8-naphthyridine", J. Org. Chem. (1984) 49, 2208-2212.

*Primary Examiner* — Paul V. Ward
(74) *Attorney, Agent, or Firm* — Brinks Hofer Gilson & Lione

(57) ABSTRACT

Substituted quinolinones of the formula I

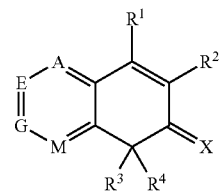

in which the variables are defined according to the description, their agriculturally suitable salts, processes and intermediates for preparing the compounds of the formula I, compositions comprising them and their use as herbicides, i.e. for controlling harmful plants, and also a method for controlling unwanted vegetation which comprises allowing a herbicidally effective amount of at least one compound of the formula I to act on plants, their seed and/or their habitat.

19 Claims, No Drawings

SUBSTITUTED QUINOLINONES HAVING HERBICIDAL ACTION

This application claims priority under 35 U.S.C. §119 to European Patent Application No. 09174833.5, filed Nov. 3, 2009, the entire contents of which is hereby incorporated herein by reference.

The present invention relates to quinolinones of the formula I

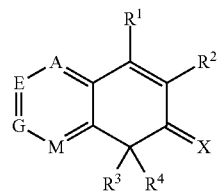

in which the variables have the following meaning:
$R^1$ is $O-R^A$, $S(O)_n-R^A$ or $O-S(O)_n-R^A$;
 $R^A$ is hydrogen, $C_1$-$C_4$-alkyl, $Z-C_3$-$C_6$-cycloalkyl, $C_1$-$C_4$-haloalkyl, $C_2$-$C_6$-alkenyl, $Z-C_3$-$C_6$-cycloalkenyl, $C_2$-$C_6$-alkynyl, Z-(tri-$C_1$-$C_4$-alkyl)silyl, $Z-C(=O)-R^a$, $-NR^i-C(O)-NR^iR^{ii}$, $Z-P(=O)(R^a)_2$, $NR^iR^{ii}$, a 3- to 7-membered monocyclic or 9- or 10-membered bicyclic saturated, unsaturated or aromatic heterocycle which contains 1, 2, 3 or 4 heteroatoms selected from the group consisting of O, N and S, which may be partially or fully substituted by groups $R^a$ and/or $R^b$,
 $R^a$ is hydrogen, OH, $C_1$-$C_8$-alkyl, $C_1$-$C_4$-haloalkyl, $Z-C_3$-$C_6$-cycloalkyl, $C_2$-$C_8$-alkenyl, $Z-C_5$-$C_6$-cycloalkenyl, $C_2$-$C_8$-alkynyl, $Z-C_1$-$C_6$-alkoxy, $Z-C_1$-$C_4$-haloalkoxy, $Z-C_3$-$C_8$-alkenyloxy, $Z-C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3, 4 or 5 groups $R^b$;
 $R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, $Z-C_3$-$C_6$-cycloalkyl, $Z-C_1$-$C_8$-alkoxy, $Z-C_1$-$C_8$-haloalkoxy, $Z-C(=O)-R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z;
 $R^i$ and $R^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;
 Z is a covalent bond or $C_1$-$C_4$-alkylene;
 n is 0, 1 or 2;
$R^2$ is phenyl, naphthyl or a 5- or 6-membered monocyclic or 9- or 10-membered bicyclic aromatic heterocycle which contains 1, 2, 3 or 4 heteroatoms selected from the group consisting of O, N and S, where the cyclic groups are unsubstituted or substituted by 1, 2, 3 or 4 groups $R^b$;
 $R^b$ independently of one another are Z—CN, Z—OH, Z—NO$_2$, Z-halogen, $C_1$-$C_8$-alkyl, $C_1$-$C_4$-haloalkyl, $C_2$-$C_8$-alkenyl, $C_2$-$C_8$-alkynyl, $Z-C_1$-$C_8$-alkoxy, $Z-C_1$-$C_8$-haloalkoxy, $Z-C_3$-$C_{10}$-cycloalkyl, $O-Z-C_3$-$C_{10}$-cycloalkyl, $Z-C(=O)-R^a$, $NR^iR^{ii}$, Z-(tri-$C_1$-$C_4$-alkyl)silyl, Z-phenyl and $S(O)_nR^{bb}$,
 where $R^{bb}$ is $C_1$-$C_8$-alkyl or $C_1$-$C_6$-haloalkyl and
 n is 0, 1 or 2;
 $R^b$ together with the group $R^b$ attached to the adjacent carbon atom may also form a five- or six-membered saturated or partially or fully unsaturated ring which, in addition to carbon atoms, may contain 1, 2 or 3 heteroatoms selected from the group consisting of O, N and S;
X is O, S or $N-R^5$;
 $R^3$, $R^4$, $R^5$ independently of one another are hydrogen, $C_1$-$C_6$-alkyl, $C_1$-$C_4$-haloalkyl, $C_2$-$C_6$-alkenyl, $C_3$-$C_6$-alkynyl, $Z-C_3$-$C_{10}$-cycloalkyl, $C_1$-$C_6$-alkoxy-$C_1$-$C_6$-alkyl, $C_1$-$C_6$-cyanoalkyl, Z-phenyl, $Z-C(=O)-R^{a2}$ or tri-$C_1$-$C_4$-alkylsilyl;
 $R^{a2}$ is $C_1$-$C_6$-alkyl, $C_1$-$C_4$-haloalkyl, $Z-C_1$-$C_6$-alkoxy, $Z-C_1$-$C_4$-haloalkoxy or $NR^iR^{ii}$;
A, E, G, M are N or C—$R^b$, at least one of these groups being N;
 $R^b$ is hydrogen or one of the groups mentioned for $R^b$;
where in the groups $R^A$, $R^3$, $R^4$ and $R^5$ and their substituents, the carbon chains and/or the cyclic groups may be partially or fully substituted by groups $R^b$,
or a N-oxide or an agriculturally suitable salt thereof.

Moreover, the invention relates to processes and intermediates for preparing the quinolinones of the formula I and the N-oxides thereof, the agriculturally usable salts thereof, and also to active compound combinations comprising them, to compositions comprising them and to their use as herbicides, i.e. for controlling harmful plants, and also to a method for controlling unwanted vegetation which comprises allowing a herbicidally effective amount of at least one quinolinone of the formula I or of an agriculturally suitable salt of I to act on plants, their seed and/or their habitat.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

WO 2008/009908 and WO 2008/071918 describe herbicidal pyridopyrazines; however, their herbicidal action at low application rates and/or their compatibility with crop plants leave scope for improvement.

It is an object of the present invention to provide compounds having herbicidal action. To be provided are in particular active compounds having strong herbicidal action, in particular even at low application rates, whose compatibility with crop plants is sufficient for commercial application.

These and further objects are achieved by the compounds of the formula I defined at the outset and by their N-oxides and also their agriculturally suitable salts.

The quinolinones of the formula I according to the invention can be obtained analogously to known synthesis routes.

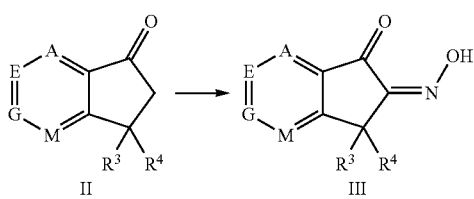

The reaction of the compounds of the formula II with hydroxylamine is usually carried out at temperatures of from −78° C. to 120° C., preferably from 0° C. to 50° C., in an inert organic solvent in the presence of a base [cf. lit. J. Med. Chem. 2008, 51, 392].

Suitable solvents are aliphatic hydrocarbons, aromatic hydrocarbons, such as toluene, o-, m- and p-xylene, halogenated hydrocarbons, ethers, nitriles, ketones, and also dimethyl sulfoxide, dimethylformamide and dimethylacetamide, particularly preferably toluene. It is also possible to use mixtures of the solvents mentioned.

Suitable bases are, in general, inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, and also alkali metal bicarbonates, organometallic compounds, alkylmagnesium halides, and also alkali metal and alkaline earth metal alkoxides, and dimethoxymagnesium, moreover organic bases, for example tertiary amines, such as trimethylamine, triethylamine, tributylamine, diisopropylethylamine and N-methylpiperidine, pyridine, substituted pyridines, such as collidine, lutidine and 4-dimethylaminopyridine, and also bicyclic amines. Particular preference is given to pyridine.

The bases are generally employed in catalytic amounts; however, they can also be used in equimolar amounts, in excess or, if appropriate, as solvents.

The starting materials of the formula II required for preparing the compounds I are known from the literature [J. Org. Chem., 1984, 49 (12), 2208] or can be prepared in accordance with the literature cited.

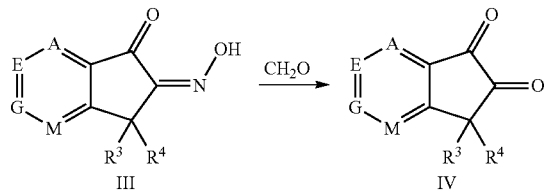

The reaction of the compounds of the formula III with formaldehyde is preferably carried out with an aqueous formaldehyde solution usually at temperatures of from −78° C. to 120° C., preferably from 0° C. to 50° C., in an inert organic solvent in the presence of an acid [cf. lit. J. Org. Chem. 2001, 66, 7666].

Suitable solvents are water, aliphatic hydrocarbons, aromatic hydrocarbons, halogenated hydrocarbons, ethers, nitriles, and also dimethyl sulfoxide, dimethylformamide and dimethylacetamide, particularly preferably water. It is also possible to use mixtures of the solvents mentioned.

Suitable acids and acid catalysts are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and also organic acids, such as formic acid, acetic acid, propionic acid, oxalic acid, toluenesulfonic acid, benzenesulfonic acid, camphorsulfonic acid, citric acid and trifluoroacetic acid.

The acids are generally employed in catalytic amounts; however, they can also be used in equimolar amounts, in excess or, if appropriate, as solvents.

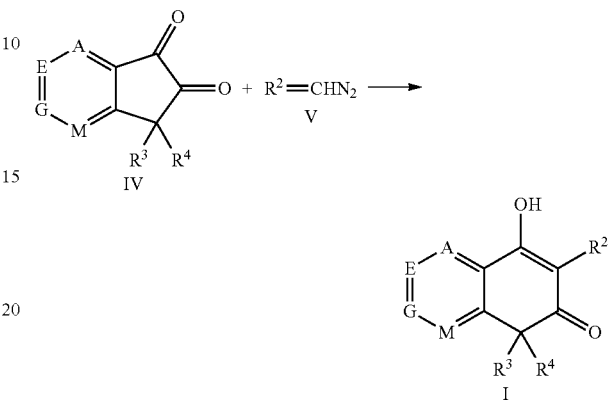

The reaction of the compounds of the formula IV with diazomethane compounds of the formula V is usually carried out at temperatures of from −78° C. to 120° C., preferably from 0° C. to 50° C., in an inert organic solvent [cf. Lit. Chem. Ber. 1969, 102, 2429].

Suitable solvents are aliphatic hydrocarbons, aromatic hydrocarbons, halogenated hydrocarbons, ethers, such as diethyl ether, diisopropyl ether, tert-butyl methyl ether, dioxane, anisole and tetrahydrofuran, nitriles, ketones, and also dimethyl sulfoxide, dimethylformamide and dimethylacetamide, particularly preferably ethers. It is also possible to use mixtures of the solvents mentioned.

The starting materials are generally reacted with one another in equimolar amounts.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, the purification can also be carried out by recrystallization or digestion.

If the synthesis yields mixtures of isomers, a separation is generally however not necessarily required since in some cases the individual isomers can be interconverted during work-up for use or during application (for example under the action of light, acids or bases). Such conversions may also take place after application, for example in the case of the treatment of plants in the treated plant or in the harmful plant to be controlled.

The organic moieties mentioned for the substituents of the compounds according to the invention are collective terms for individual enumerations of the individual group members. All hydrocarbon chains, such as alkyl, haloalkyl, alkenyl, alkynyl, and the alkyl moieties and alkenyl moieties in alkoxy, haloalkoxy, alkylamino, dialkylamino, N-alkylsulfonylamino, alkenyloxy, alkynyloxy, alkoxyamino, alkylaminosulfonylamino, dialkylaminosulfonylamino, alkenylamino, alkynylamino, N-(alkenyl)-N-(alkyl)amino, N-(alkynyl)-N-(alkyl)amino, N-(alkoxy)-N-(alkyl)amino, N-(alkenyl)-N-(alkoxy)amino or N-(alkynyl)-N-(alkoxy) amino can be straight-chain or branched.

The prefix $C_n$-$C_m$— indicates the respective number of carbons of the hydrocarbon unit. Unless indicated otherwise, halogenated substituents preferably carry one to five identical or different halogen atoms, in particular fluorine atoms or chlorine atoms.

The meaning halogen denotes in each case fluorine, chlorine, bromine or iodine.

Examples of other meanings are:

alkyl and the alkyl moieties for example in alkoxy, alkylamino, dialkylamino, N-alkylsulfonylamino, alkylaminosulfonylamino, dialkylaminosulfonylamino, N-(alkenyl)-N-(alkyl)amino, N-(alkynyl)-N-(alkyl)amino, N-(alkoxy)-N-(alkyl)amino: saturated straight-chain or branched hydrocarbon radicals having one or more carbon atoms, for example 1 or 2, 1 to 4 or 1 to 6 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment according to the invention, alkyl denotes small alkyl groups, such as $C_1$-$C_4$-alkyl. In another embodiment according to the invention, alkyl denotes relatively large alkyl groups, such as $C_5$-$C_6$-alkyl.

Haloalkyl: an alkyl radical as mentioned above, some or all of whose hydrogen atoms are substituted by halogen atoms, such as fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl and the cycloalkyl moieties for example in cycloalkoxy or cycloalkylcarbonyl: monocyclic saturated hydrocarbon groups having three or more carbon atoms, for example 3 to 6 carbon ring members, such as cyclopropyl, cyclobutyl, cyclopentyl and cyclohexyl.

Alkenyl and the alkenyl moieties for example in alkenylamino, alkenyloxy, N-(alkenyl)-N-(alkyl)amino, N-(alkenyl)-N-(alkoxy)amino: monounsaturated straight-chain or branched hydrocarbon radicals having two or more carbon atoms, for example 2 to 4, 2 to 6 or 3 to 6 carbon atoms, and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Cycloalkenyl: monocyclic monounsaturated hydrocarbon groups having 3 to 6, preferably 5 or 6, carbon ring members, such as cyclopenten-1-yl, cyclopenten-3-yl, cyclohexen-1-yl, cyclohexen-3-yl, cyclohexen-4-yl.

Alkynyl and the alkynyl moieties for example in alkynyloxy, alkynylamino, N-(alkynyl)-N-(alkyl)amino or N-(alkynyl)-N-(alkoxy)amino: straight-chain or branched hydrocarbon groups having two or more carbon atoms, for example 2 to 4, 2 to 6 or 3 to 6 carbon atoms, and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy: alkyl as defined above which is attached via an oxygen atom, for example methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

3- to 7-membered monocyclic or 9- or 10-membered bicyclic saturated, unsaturated or aromatic heterocycle which contains 1, 2, 3, or 4 heteroatoms selected from the group consisting of O, N and S and which can be attached via C or N. Preferred from among these are 5- or 6-membered heterocycles.

Saturated or unsaturated heterocyclic groups which are attached via N, such as: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl.

Heteroaromatic groups which are attached via C, such as: pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl.

The compounds of the formula I may, depending on the substitution pattern, contain one or more further centers of chirality. Accordingly, the compounds according to the invention can be present as pure enantiomers or diastereomers or as enantiomer or diastereomer mixtures. The invention provides both the pure enantiomers or diastereomers and their mixtures.

The compounds of the formula I may also be present in the form of the N-oxides and/or of their agriculturally useful salts, the type of salt generally not being important. Suitable salts are generally the salts of those cations or the acid addition salts of those acids whose cations and anions, respectively, have no adverse effect on the herbicidal activity of the compounds I.

Suitable cations are in particular ions of the alkali metals, preferably lithium, sodium or potassium, of the alkaline earth metals, preferably calcium or magnesium, and of the transition metals, preferably manganese, copper, zinc or iron. Another cation that may be used is ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Another suitable ammonium cation is the pyridine nitrogen atom of the formula I quaternized by alkylation or arylation. Also suitable are phosphonium ions, sulfonium ions, preferably tri($C_1$-$C_4$-alkyl)sulfonium, or sulfoxonium ions, preferably tri($C_1$-$C_4$-alkyl)sulfoxonium.

Anions of suitable acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate, butyrate or trifluoroacetate.

With respect to the variables, the particularly preferred embodiments of the intermediates correspond to those of the groups of the formula I.

In a particular embodiment, the variables of the compounds of the formula I have the following meanings, these meanings, both on their own and in combination with one another, being particular embodiments of the compounds of the formula I:

In one preferred embodiment of the compounds of the formula I, A is N and E, G and M are C—$R^c$. These compounds correspond to the formula I.1

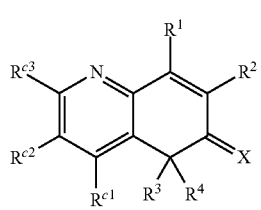

in which the groups $R^3$ and $R^4$ are hydrogen and $R^{c1}$, $R^{c2}$ and $R^{c3}$ each correspond to a group $R^c$ and preferably have the following meanings:
$R^{c1}$ is H, OH, CN, halogen, alkyl, alkoxy, haloalkyl, in particular H;
$R^{c2}$ is H, OH, CN, halogen, alkyl, alkoxy, haloalkyl, in particular H, Br, OH and $OCH_3$;
$R^{c3}$ is H, OH, CN, halogen, alkyl, alkoxy, haloalkyl, in particular H.

In a further embodiment of the compounds of the formula I, A, E and M are C—$R^c$ and G is N. These compounds correspond to the formula I.2

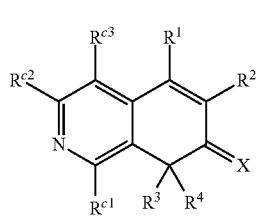

in which the groups $R^3$ and $R^4$ are hydrogen and $R^{c1}$, $R^{c2}$ and $R^{c4}$ each correspond to a group $R^c$ and preferably have the following meanings:
$R^{c1}$ is H, OH, CN, halogen, alkyl, alkoxy, haloalkyl, in particular H;
$R^{c2}$ is H, OH, CN, halogen, alkyl, alkoxy, haloalkyl, in particular H; and
$R^{c3}$ is H, OH, CN, halogen, alkyl, alkoxy, haloalkyl, in particular H, Br, OH and $OCH_3$.

In a further embodiment of the compounds of the formula I, A and G are N and E and M are C—$R^c$. These compounds correspond to the formula I.3

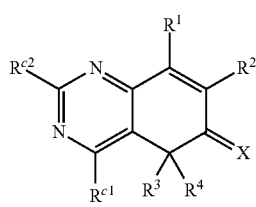

in which the groups $R^3$ and $R^4$ are hydrogen and $R^{c1}$ and $R^{c3}$ each correspond to a group $R^c$ and preferably have the following meanings:
$R^{c1}$ is H, OH, CN, halogen, alkyl, alkoxy, haloalkyl, in particular H, Br, OH and $OCH_3$;
$R^{c2}$ is H, OH, CN, halogen, alkyl, alkoxy, haloalkyl, in particular H, Br, OH and $OCH_3$.

In a further embodiment of the compounds of the formula I, A and M are N and E and G are C—$R^c$. These compounds correspond to the formula I.4

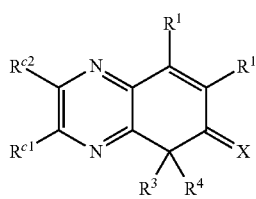

in which the groups $R^3$ and $R^4$ are hydrogen and $R^{c2}$ and $R^{c3}$ each correspond to a group $R^c$ and preferably have the following meanings:

$R^{c2}$ is H, OH, CN, halogen, alkyl, alkoxy, haloalkyl, in particular H;

$R^{c1}$ is H, OH, CN, halogen, alkyl, alkoxy, haloalkyl, in particular H, Br, OH and OCH$_3$.

In a further embodiment of the compounds of the formula I, A and E are N and G and M are C—R$^c$. These compounds correspond to the formula I.5,

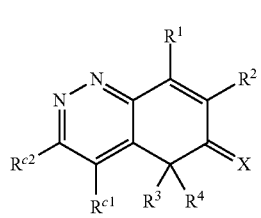

I.5 in which the groups $R^3$ and $R^4$ are hydrogen and $R^{c3}$ and $R^{c4}$ each correspond to a group $R^c$ and preferably have the following meanings:

$R^{c1}$ is H, OH, CN, halogen, alkyl, alkoxy, haloalkyl, in particular H, Br, OH and OCH$_3$;

$R^{c2}$ is H, OH, CN, halogen, alkyl, alkoxy, haloalkyl, in particular H.

Particularly preferred aspects of the compounds of the formula I relate to those of each of the formulae I.1 to I.5 in which the variables have the meanings preferred for formula I.

In a first preferred embodiment of the invention, $R^1$ is O—R$^4$.

In a further preferred embodiment of the invention, $R^1$ is S(O)$_n$—R$^4$ where n is preferably 0 or 2, in particular 2.

In a further preferred embodiment, $R^1$ is O—S(O)$_n$—R$^4$, where n is preferably 0 or 2, in particular 2, such as, for example, OS(O)$_2$—CH$_3$, OS(O)$_2$—O$_2$H$_5$, OS(O)$_2$—C$_3$H$_7$, OS(O)$_2$—C$_6$H$_5$ or OS(O)$_2$-(4-CH$_3$—C$_6$H$_4$).

In a further preferred embodiment, $R^1$ is O—S(O), —NR$^i$R$^{ii}$, which has in particular the groups NR$^i$R$^{ii}$ mentioned below as being preferred.

$R^4$ is in particular H, C$_1$-C$_6$-alkylcarbonyl, such as C(O)CH$_3$, C(O)CH$_2$CH$_3$, C(O)CH(CH$_3$)$_2$ or C(O)C(CH$_3$)$_3$; C$_1$-C$_6$-cycloalkylcarbonyl, such as cyclopropylcarbonyl, cyclopentylcarbonyl or cyclohexylcarbonyl; C$_2$-C$_6$-alkenylcarbonyl, such as C(O)CH=CH$_2$ or C(O)CH$_2$CH=CH$_2$, optionally subst. benzoyl, such as C(O)C$_6$H$_5$, C(O)[2-CH$_3$—C$_6$H$_4$], C(O)[4-CH$_3$—C$_6$H$_4$], C(O)[2-F—C$_6$H$_4$], C(O)[4-F—C$_6$H$_4$], or optionally subst. heteroaryl, such as pyridine, which is attached via a carbonyl group. Particularly preferably, $R^4$ is H or C$_1$-C$_6$-alkylcarbonyl.

More particularly preferably, $R^4$ is selected from the group consisting of H, OCH$_3$, C(O)CH$_3$, C(O)CH$_2$CH$_3$, C(O)CH(CH$_3$)$_2$, C(O)C(CH$_3$)$_3$, C(O)-c-C$_3$H$_5$, C(O)—C$_6$H$_5$, C(O)—CH$_2$C$_6$H$_5$, C(O)CH$_2$Cl, C(O)CF$_3$, C(O)CH$_2$OCH$_3$, C(O)N(CH$_3$)$_2$ and C(O)OCH$_2$CH$_3$.

In a further preferred embodiment of the invention, $R^4$ is NR$^i$R$^{ii}$.

In a further preferred embodiment of the invention, $R^4$ is Z—NR$^i$—C(O)—NR$^i$R$^{ii}$, where R$^i$ and R$^{ii}$ are as defined at the outset and preferably as defined below. In further embodiments, C$_1$-C$_4$-alkoxy, C$_1$-C$_4$-haloalkoxy and C$_1$-C$_4$-alkoxy-C$_1$-C$_4$-alkyl, in particular OCH$_3$, OC$_2$H$_5$, CH$_2$CH$_2$OCH$_3$ and CH$_2$CH$_2$Cl, may also be possible for R$^i$ and R$^{ii}$, independently of one another.

R$^i$ and R$^{ii}$ are preferably C$_1$-C$_8$-alkyl, C$_1$-C$_4$-haloalkyl, Z—C$_3$-C$_6$-cycloalkyl, Z—C$_1$-C$_8$-alkoxy, Z—C$_1$-C$_8$-haloalkoxy, Z-phenyl, Z—C(=O)—R$^a$ or Z-hetaryl. Here, preference is given to CH$_3$, C$_2$H$_5$, n-propyl, CH(CH$_3$)$_2$, butyl, 2-chloroethyl, cyclopentyl, cyclohexyl, 2-ethoxymethyl, 2-chloroethoxy, phenyl, pyrimidines or triazines whose rings are unsubstituted or substituted. Here, preferred substituents are C$_1$-C$_4$-alkylcarbonyl or C$_1$-C$_4$-haloalkylcarbonyl, in particular C(=O)—CH$_3$, C(=O)—C$_2$H$_5$, C(=O)—C$_3$H$_7$, C(=O)—CH(CH$_3$)$_2$, butylcarbonyl and C(=O)—CH$_2$Cl. Particularly preferred aspects of the group NR$^i$R$^{ii}$ are N(di-C$_1$-C$_4$-alkyl), in particular N(CH$_3$)—C$_1$-C$_4$-alkyl, such as N(CH$_3$)$_2$, N(CH$_3$)CH$_2$CH$_3$, N(CH$_3$)C$_3$H$_7$ and N(CH$_3$)CH(CH$_3$)$_2$.

Further particularly preferred aspects of NR$^i$R$^{ii}$ are NH-aryl, where aryl is preferably phenyl which is substituted—in particular in the 2- and 6-position—by one to three identical or different halogen, CH$_3$, halo-C$_1$-C$_2$-alkyl, halo-C$_1$-C$_2$-alkoxy and carboxyl groups, such as 2-C$_{1-6}$—COOH—C$_6$H$_3$, 2,6-Cl$_2$-C$_6$H$_3$, 2,6-Cl$_2$-C$_6$H$_3$, 2,6-Cl$_2$-3-C$_6$H$_2$, 2-CF$_3$, 6-CH$_2$CHF$_2$—C$_6$H$_3$, 2-CF$_3$-6-OCF$_3$—C$_6$H$_3$ and 2-CF$_3$-6-CH$_2$CHF$_2$—C$_6$H$_3$.

Further aspects of NR$^i$R$^{ii}$ are NH-heteroaryl, where heteroaryl is preferably one of the preferred heteroaromatic groups below, in particular triazinyl, pyrimidinyl or triazolopyrimidinyl, such as [1,2,4]triazolo[1,5-a]pyrimidin-2-yl, which groups may be substituted, in particular by C$_1$-C$_4$-alkoxy and/or halogen. Particular preference is given to 5,7-dimethoxy-[1,2,4]triazolo[1,5-a]pyrimidin-2-yl, 5,7-diethoxy-[1,2,4]-triazolo[1,5-a]pyrimidin-2-yl, 5-fluoro-7-methoxy-[1,2,4]triazolo[1,5-a]pyrimidin-2-yl and 5-fluoro-7-ethoxy-[1,2,4]triazolo[1,5-a]pyrimidin-2-yl.

In particularly preferred embodiments of the compounds of the formula I and in particular those of the formula I.1, $R^1$ is selected from the group consisting of OH, OCH$_3$, OC(O)CH$_3$, OC(O)CH$_2$CH$_3$, OC(O)CH(CH$_3$)$_2$, OC(O)C(CH$_3$)$_3$, OC(O)-c-C$_3$H$_5$, OC(O)—C$_6$H$_5$, OC(O)—CH$_2$C$_6$H$_5$, OC(O)CH$_2$Cl, OC(O)—CF$_3$, OC(O)—CH$_2$OCH$_3$, OC(O)—N(CH$_3$)$_2$ and OC(O)—OCH$_2$CH$_3$.

In particularly preferred embodiments of the compounds of the formula I and in particular those of the formula I.1, $R^2$ is phenyl which is substituted by a group selected from the group consisting of 2-Br, 2-Cl, 2,4-Cl$_2$, 2-Cl-4-F, 2-Cl-5-F, 2-Cl-6-F, 2-Cl-4-CF$_3$, 2-Cl-5-CF$_3$, 2-Cl-6-CF$_3$, 2-Cl-3,6-F$_2$, 2-F, 2,4-F$_2$, 2,5-F$_2$, 2,6-F$_2$, 2-F-4-CF$_3$, 2-F-5-CF$_3$, 2-F-6-CF$_3$, 2,3,6-F$_3$, 2-NO$_2$, 2-NO$_2$-4-F, 2-NO$_2$-5-F, 2-NO$_2$-6-F, 2-NO$_2$-4-CF$_3$, 2-NO$_2$-5-CF$_3$, 2-NO$_2$-6-CF$_3$, 2-NO$_2$-3,6-F$_2$, 2-CN, 2-CH$_3$, 2-CH$_3$-4-F, 2-CH$_3$-5-F, 2-CH$_3$-6-F, 2-CH$_3$-4-CF$_3$, 2-CH$_3$-5-CF$_3$, 2-CH$_3$-6-CF$_3$, 2-CH$_3$-3,6-F$_2$, 2-OCH$_3$, 2-OCH$_3$-4-F, 2-OCH$_3$-5-F, 2-OCH$_3$-6-F, 2-OCH$_3$-4-CF$_3$, 2-OCH$_3$-5-CF$_3$, 2-OCH$_3$-6-CF$_3$, 2-OCH$_3$-3,6-F$_2$, 2-CHF$_2$, 2-CHF$_2$-4-F, 2-CHF$_2$-5-F, 2-CHF$_2$-6-F, 2-CHF$_2$-4-CF$_3$, 2-CHF$_2$-5-CF$_3$, 2-CHF$_2$-6-CF$_3$, 2-CHF$_2$-3,6-F$_2$, 2-CF$_3$, 2-CF$_3$-4-F, 2-CF$_3$-5-F, 2-CF$_3$-6-F, 2-CF$_3$-4-CF$_3$, 2-CF$_3$-5-CF$_3$, 2-CF$_3$-6-CF$_3$, 2-CF$_3$-3,6-F$_2$, 2-OCHF$_2$, 2-OCHF$_2$-4-F, 2-OCHF$_2$-5-F, 2-OCHF$_2$-6-F, 2-OCHF$_2$-4-CF$_3$, 2-OCHF$_2$-5-CF$_3$, 2-OCHF$_2$-6-CF$_3$, 2-OCHF$_2$-3,6-F$_2$, 2-OCF$_3$, 2-OCF$_3$-4-F, 2-OCF$_3$-5-F, 2-OCF$_3$-6-F, 2-OCF$_3$-4-CF$_3$, 2-OCF$_3$-5-CF$_3$, 2-OCF$_3$-6-CF$_3$ and 2-OCF$_3$-3,6-F$_2$.

In a further preferred embodiment of the invention, $R^4$ is a 5- or 6-membered heterocycle optionally substituted by R$^b$ as defined above, which preferably has either 1, 2, 3 or 4 nitrogen atoms or 1 oxygen or 1 sulfur atom and if appropriate 1 or 2 nitrogen atoms as ring members and which is unsubstituted or may have 1 or 2 substituents selected from $R^b$. Preference is given to saturated or unsaturated groups attached via nitrogen, such as, for example:

Heteroaromatic groups: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl;

In another aspect, $R^4$ is a heteroaromatic group attached via carbon, such as pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, where each of the heterocycles mentioned here in an exemplary manner may have 1 or 2 substituents selected from $R^b$. Preferred groups $R^b$ are in particular F, Cl, CN, $NO_2$, $CH_3$, $C_2H_5$, $OCH_3$, $OC_2H_5$, $OCHF_2$, $OCF_3$ and $CF_3$.

In a further preferred aspect, $R^2$ is phenyl which is unsubstituted or partially or fully substituted by groups $R^b$. Particular preference is given to compounds in which a group $R^b$ is located in the ortho-position. Such compounds of the formula I are described by the formula I.A:

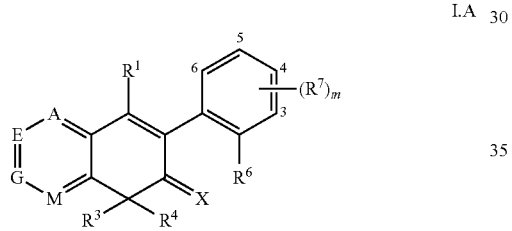

I.A

In formula I.A, the index m is zero or an integer from one to four, preferably 0, 1 or 2, in particular 0 or 1. $R^6$ and $R^7$ are groups $R^b$ as defined at the outset, preferably halogen, $NO_2$, $C_1$-$C_4$-alkyl, $C_1$-$C_2$-haloalkyl and $C_1$-$C_4$-alkoxy. One group $R^7$ is preferably located in position 5. A group $R^7$ in position 3 is a further preferred embodiment.

Particularly preferably, $R^6$ is Br, F, $NO_2$, CN, $CH_3$, $OCH_3$, $CF_3$, $OCF_3$, $CHF_2$ or $OCHF_2$. $R^6$ is particularly preferably halogen or halomethyl, such as Cl, F or $CF_3$. Especially preferably, $(R^7)_m$ is selected from the group consisting of 4-F, 5-F, 6-F, 4-$CF_3$, 5-$CF_3$ and 3,6-$F_2$.

The groups $R^3$ and $R^4$ are preferably hydrogen.

In a preferred embodiment, X is O.

In a further embodiment, X is S.

In a further embodiment, X is $NR^5$.

$R^5$ is preferably H, $C_1$-$C_6$-alkyl, such as $CH_3$, $C_2H_5$, n-$C_3H_7$, $CH(CH_3)_2$, n-$C_3H_9$, or $C(CH_3)_3$; $C_3$-$C_6$-cycloalkyl-$C_1$-$C_4$-alkyl, such as cyclopropylmethyl, $C_3$-$C_6$-alkenyl, such as $CH_2CH=CH_2$, $CH_2C(CH_3)=CH_2$, $CH_2CH_2H=CH_2$, $CH_2CH_2C(CH_3)=CH_2$, $CH_2CH_2CH_2CH=CH_2$, $CH_2CH_2CH_2C(CH_3)=CH_2$, or optionally subst. phenyl, such as $C_6H_5$, 4-$CH_3$—$C_6H_4$, 4-F—$C_6H_4$ or $S(O)_n$—$R^N$, where $R^N$ is $C_1$-$C_6$-haloalkyl, such as $CH_2CF_3$, $CH_2CHF_2$.

A further embodiment relates to the N-oxides of the compounds of the formula I.

A further embodiment relates to salts of the compounds of the formula I, in particular those which are obtainable by quaternization of the pyridine nitrogen atom, which may preferably take place by alkylation or arylation of the compounds of the formula I. Preferred salts of the compounds are thus the N-alkyl salts, in particular the N-methyl salts, and the N-phenyl salts.

In particular with a view to their use, preference is given to the compounds of the formula I compiled in the tables below, which compounds correspond to the formulae I.1A*, I.2A*, I.3A*, I.4A* and I.5A*, respectively. The groups mentioned for a substituent in the tables are furthermore per se, independently of the combination in which they are mentioned, a particularly preferred aspect of the substituent in question.

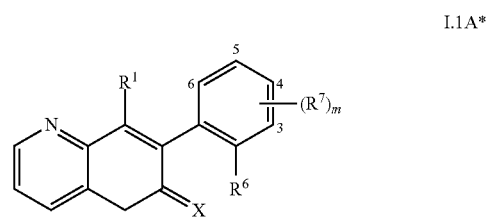

I.1A*

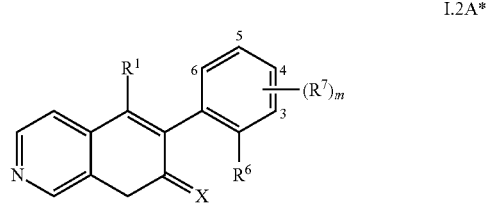

I.2A*

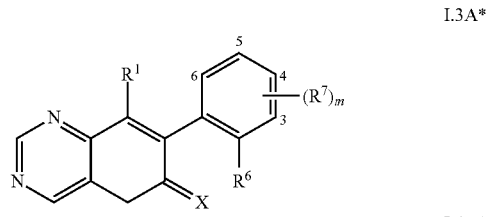

I.3A*

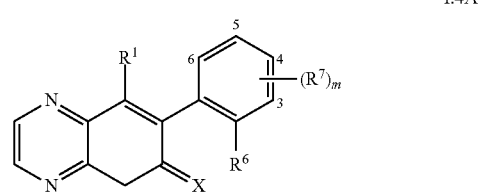

I.4A*

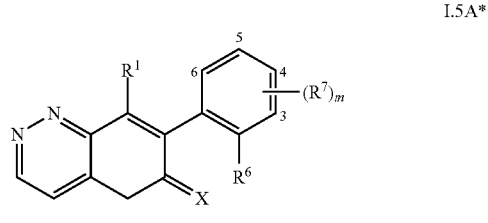

I.5A*

Table 1

Compounds of the formula I.1A*, in which X is oxygen, the index m in $(R^7)_m$ is zero and the combination of $R^1$ and $R^6$ for a compound corresponds in each case to one row of Table A Table 2

Compounds of the formula I.1A*, in which X is oxygen, $(R^7)_m$ is 4-Cl and the combination of $R^1$ and $R^6$ for a compound corresponds in each case to one row of Table A Table 3

Compounds of the formula I.1A*, in which X is oxygen, $(R^7)_m$ is 3-F and the combination of $R^1$ and $R^6$ for a compound corresponds in each case to one row of Table A Table 4
Compounds of the formula I.1A*, in which X is oxygen, $(R^7)_m$ is 4-F and the combination of $R^1$ and $R^6$ for a compound corresponds in each case to one row of Table A Table 5
Compounds of the formula I.1A*, in which X is oxygen, $(R^7)_m$ is 5-F and the combination of $R^1$ and $R^6$ for a compound corresponds in each case to one row of Table A Table 6
Compounds of the formula I.1A*, in which X is oxygen, $(R^7)_m$ is 6-F and the combination of $R^1$ and $R^6$ for a compound corresponds in each case to one row of Table A Table 7
Compounds of the formula I.1A*, in which X is oxygen, $(R^7)_m$ is 4-$CF_3$ and the combination of $R^1$ and $R^6$ for a compound corresponds in each case to one row of Table A Table 8
Compounds of the formula I.1A*, in which X is oxygen, $(R^7)_m$ is 5-$CF_3$ and the combination of $R^1$ and $R^6$ for a compound corresponds in each case to one row of Table A Table 9
Compounds of the formula I.1A*, in which X is oxygen, $(R^7)_m$ is 3,6-$F_2$ and the combination of $R^1$ and $R^6$ for a compound corresponds in each case to one row of Table A Table 10
Compounds of the formula I.1A*, in which X is sulfur, the index m in $(R^7)_m$ is zero and the combination of $R^1$ and $R^6$ for a compound corresponds in each case to one row of Table A Table 11
Compounds of the formula I.1A*, in which X is sulfur, $(R^7)_m$ is 4-Cl and the combination of $R^1$ and $R^6$ for a compound corresponds in each case to one row of Table A Table 12
Compounds of the formula I.1A*, in which X is sulfur, $(R^7)_m$ is 3-F and the combination of $R^1$ and $R^6$ for a compound corresponds in each case to one row of Table A Table 13
Compounds of the formula I.1A*, in which X is sulfur, $(R^7)_m$ is 4-F and the combination of $R^1$ and $R^6$ for a compound corresponds in each case to one row of Table A Table 14
Compounds of the formula I.1A*, in which X is sulfur, $(R^7)_m$ is 5-F and the combination of $R^1$ and $R^6$ for a compound corresponds in each case to one row of Table A Table 15
Compounds of the formula I.1A*, in which X is sulfur, $(R^7)_m$ is 6-F and the combination of $R^1$ and $R^6$ for a compound corresponds in each case to one row of Table A Table 16
Compounds of the formula I.1A*, in which X is sulfur, $(R^7)_m$ is 4-$CF_3$ and the combination of $R^1$ and $R^6$ for a compound corresponds in each case to one row of Table A Table 17
Compounds of the formula I.1A*, in which X is sulfur, $(R^7)_m$ is 5-$CF_3$ and the combination of $R^1$ and $R^6$ for a compound corresponds in each case to one row of Table A Table 18
Compounds of the formula I.1A*, in which X is sulfur, $(R^7)_m$ is 3,6-$F_2$ and the combination of $R^1$ and $R^6$ for a compound corresponds in each case to one row of Table A Table 19
Compounds of the formula I.1A*, in which X is sulfur, the index m in $(R^7)_m$ is zero and the combination of $R^1$ and $R^6$ for a compound corresponds in each case to one row of Table A Table 20
Compounds of the formula I.1A*, in which X is sulfur, $(R^7)_m$ is 4-Cl and the combination of $R^1$ and $R^6$ for a compound corresponds in each case to one row of Table A Table 21
Compounds of the formula I.1A*, in which X is sulfur, $(R^7)_m$ is 3-F and the combination of $R^1$ and $R^6$ for a compound corresponds in each case to one row of Table A Table 22
Compounds of the formula I.1A*, in which X is sulfur, $(R^7)_m$ is 4-F and the combination of $R^1$ and $R^6$ for a compound corresponds in each case to one row of Table A Table 23
Compounds of the formula I.1A*, in which X is sulfur, $(R^7)_m$ is 5-F and the combination of $R^1$ and $R^6$ for a compound corresponds in each case to one row of Table A Table 24
Compounds of the formula I.1A*, in which X is sulfur, $(R^7)_m$ is 6-F and the combination of $R^1$ and $R^6$ for a compound corresponds in each case to one row of Table A Table 25
Compounds of the formula I.1A*, in which X is sulfur, $(R^7)_m$ is 4-$CF_3$ and the combination of $R^1$ and $R^6$ for a compound corresponds in each case to one row of Table A Table 26
Compounds of the formula I.1A*, in which X is sulfur, $(R^7)_m$ is 5-$CF_3$ and the combination of $R^1$ and $R^6$ for a compound corresponds in each case to one row of Table A Table 27
Compounds of the formula I.1A*, in which X is sulfur, $(R^7)_m$ is 3,6-$F_2$ and the combination of $R^1$ and $R^6$ for a compound corresponds in each case to one row of Table A Table 28
Compounds of the formula I.1A*, in which X is N—H, the index m in $(R^7)_m$ is zero and the combination of $R^1$ and $R^6$ for a compound corresponds in each case to one row of Table A Table 29
Compounds of the formula I.1A*, in which X is N—$CH_3$, the index m in $(R^7)_m$ is zero and the combination of $R^1$ and $R^6$ for a compound corresponds in each case to one row of Table A Table 30
Compounds of the formula I.1A*, in which X is N—$C_2H_5$, the index m in $(R^7)_m$ is zero and the combination of $R^1$ and $R^6$ for a compound corresponds in each case to one row of Table A Table 31
Compounds of the formula I.1A*, in which X is N-n-$C_3H_7$, the index m in $(R^7)_m$ is zero and the combination of $R^1$ and $R^6$ for a compound corresponds in each case to one row of Table A Table 32
Compounds of the formula I.1A*, in which X is N—CH($CH_3$)$_2$, the index m in $(R^7)_m$ is zero and the combination of $R^1$ and $R^6$ for a compound corresponds in each case to one row of Table A Table 33
Compounds of the formula I.1A*, in which X is N-n-$C_4H_9$, the index m in $(R^7)_m$ is zero and the combination of $R^1$ and $R^6$ for a compound corresponds in each case to one row of Table A Table 34
Compounds of the formula I.1A*, in which X is N—$CH_2CH$=$CH_2$, the index m in $(R^7)_m$ is zero and the combination of $R^1$ and $R^6$ for a compound corresponds in each case to one row of Table A Table 35
Compounds of the formula I.1A*, in which X is N—$CH_2C≡CH$, the index m in $(R^7)_m$ is zero and the combination of $R^1$ and $R^6$ for a compound corresponds in each case to one row of Table A Table 36
Compounds of the formula I.1A*, in which X is N—$CH_2CN$, the index m in $(R^7)_m$ is zero and the combination of $R^1$ and $R^6$ for a compound corresponds in each case to one row of Table A Table 37
Compounds of the formula I.1A*, in which X is N—$CH_2CF_3$, the index m in $(R^7)_m$ is zero and the combination of $R^1$ and $R^6$ for a compound corresponds in each case to one row of Table A Table 38
Compounds of the formula I.1A*, in which X is N—$CH_2C_6H_5$, the index m in $(R^7)_m$ is zero and the combination of $R^1$ and $R^6$ for a compound corresponds in each case to one row of Table A Table 39
Compounds of the formula I.1A*, in which X is N—H, $(R^7)_m$ is 4-Cl and the combination of $R^1$ and $R^6$ for a compound corresponds in each case to one row of Table A Table 40
Compounds of the formula I.1A*, in which X is N—$CH_3$, $(R^7)_m$ is 4-Cl and the combination of $R^1$ and $R^6$ for a compound corresponds in each case to one row of Table A Table 41
Compounds of the formula I.1A*, in which X is N—$C_2H_5$, $(R^7)_m$ is 4-Cl and the combination of $R^1$ and $R^6$ for a compound corresponds in each case to one row of Table A Table 42
Compounds of the formula I.1A*, in which X is N-n-$C_3H_7$, $(R^7)_m$ is 4-Cl and the combination of $R^1$ and $R^6$ for a compound corresponds in each case to one row of Table A Table 43
Compounds of the formula I.1A*, in which X is N—$CH(CH_3)_2$, $(R^7)_m$ is 4-Cl and the combination of $R^1$ and $R^6$ for a compound corresponds in each case to one row of Table A Table 44
Compounds of the formula I.1A*, in which X is N-n-$C_4H_9$, $(R^7)_m$ is 4-Cl and the combination of $R^1$ and $R^6$ for a compound corresponds in each case to one row of Table A Table 45
Compounds of the formula I.1A*, in which X is N—$CH_2CH=CH_2$, $(R^7)_m$ is 4-Cl and the combination of $R^1$ and $R^6$ for a compound corresponds in each case to one row of Table A Table 46
Compounds of the formula I.1A*, in which X is N—$CH_2C≡CH$, $(R^7)_m$ is 4-Cl and the combination of $R^1$ and $R^6$ for a compound corresponds in each case to one row of Table A Table 47
Compounds of the formula I.1A*, in which X is N—$CH_2CN$, $(R^7)_m$ is 4-Cl and the combination of $R^1$ and $R^6$ for a compound corresponds in each case to one row of Table A Table 48
Compounds of the formula I.1A*, in which X is N—$CH_2CF_3$, $(R^7)_m$ is 4-Cl and the combination of $R^1$ and $R^6$ for a compound corresponds in each case to one row of Table A Table 49
Compounds of the formula I.1A*, in which X is N—$CH_2C_6H_5$, $(R^7)_m$ is 4-Cl and the combination of $R^1$ and $R^6$ for a compound corresponds in each case to one row of Table A Table 50
Compounds of the formula I.1A*, in which X is N—H, $(R^7)_m$ is 3-F and the combination of $R^1$ and $R^6$ for a compound corresponds in each case to one row of Table A Table 51
Compounds of the formula I.1A*, in which X is N—$CH_3$, $(R^7)_m$ is 3-F and the combination of $R^1$ and $R^6$ for a compound corresponds in each case to one row of Table A Table 52
Compounds of the formula I.1A*, in which X is N—$C_2H_5$, $(R^7)_m$ is 3-F and the combination of $R^1$ and $R^6$ for a compound corresponds in each case to one row of Table A Table 53
Compounds of the formula I.1A*, in which X is N-n-$C_3H_7$, $(R^7)_m$ is 3-F and the combination of $R^1$ and $R^6$ for a compound corresponds in each case to one row of Table A Table 54
Compounds of the formula I.1A*, in which X is N—$CH(CH_3)_2$, $(R^7)_m$ is 3-F and the combination of $R^1$ and $R^6$ for a compound corresponds in each case to one row of Table A Table 55
Compounds of the formula I.1A*, in which X is N-n-$C_4H_9$, $(R^7)_m$ is 3-F and the combination of $R^1$ and $R^6$ for a compound corresponds in each case to one row of Table A Table 56
Compounds of the formula I.1A*, in which X is N—$CH_2CH=CH_2$, $(R^7)_m$ is 3-F and the combination of $R^1$ and $R^6$ for a compound corresponds in each case to one row of Table A Table 57
Compounds of the formula I.1A*, in which X is N—$CH_2C≡CH$, $(R^7)_m$ is 3-F and the combination of $R^1$ and $R^6$ for a compound corresponds in each case to one row of Table A Table 58
Compounds of the formula I.1A*, in which X is N—$CH_2CN$, $(R^7)_m$ is 3-F and the combination of $R^1$ and $R^6$ for a compound corresponds in each case to one row of Table A Table 59
Compounds of the formula I.1A*, in which X is N—$CH_2CF_3$, $(R^7)_m$ is 3-F and the combination of $R^1$ and $R^6$ for a compound corresponds in each case to one row of Table A Table 60
Compounds of the formula I.1A*, in which X is N—$CH_2C_6H_5$, $(R^7)_m$ is 3-F and the combination of $R^1$ and $R^6$ for a compound corresponds in each case to one row of Table A Table 61
Compounds of the formula I.1A*, in which X is N—H, $(R^7)_m$ is 4-F and the combination of $R^1$ and $R^6$ for a compound corresponds in each case to one row of Table A Table 62
Compounds of the formula I.1A*, in which X is N—$CH_3$, $(R^7)_m$ is 4-F and the combination of $R^1$ and $R^6$ for a compound corresponds in each case to one row of Table A Table 63
Compounds of the formula I.1A*, in which X is N—$C_2H_5$, $(R^7)_m$ is 4-F and the combination of $R^1$ and $R^6$ for a compound corresponds in each case to one row of Table A Table 64
Compounds of the formula I.1A*, in which X is N-n-$C_3H_7$, $(R^7)_m$ is 4-F and the combination of $R^1$ and $R^6$ for a compound corresponds in each case to one row of Table A Table 65
Compounds of the formula I.1A*, in which X is N—$CH(CH_3)_2$, $(R^7)_m$ is 4-F and the combination of $R^1$ and $R^6$ for a compound corresponds in each case to one row of Table A Table 66
Compounds of the formula I.1A*, in which X is N-n-$C_4H_9$, $(R^7)_m$ is 4-F and the combination of $R^1$ and $R^6$ for a compound corresponds in each case to one row of Table A Table 67
Compounds of the formula I.1A*, in which X is N—$CH_2CH$=$CH_2$, $(R^7)_m$ is 4-F and the combination of $R^1$ and $R^6$ for a compound corresponds in each case to one row of Table A Table 68
Compounds of the formula I.1A*, in which X is N—$CH_2C$≡$CH$, $(R^7)_m$ is 4-F and the combination of $R^1$ and $R^6$ for a compound corresponds in each case to one row of Table A Table 69
Compounds of the formula I.1A*, in which X is N—$CH_2CN$, $(R^7)_m$ is 4-F and the combination of $R^1$ and $R^6$ for a compound corresponds in each case to one row of Table A Table 70
Compounds of the formula I.1A*, in which X is N—$CH_2CF_3$, $(R^7)_m$ is 4-F and the combination of $R^1$ and $R^6$ for a compound corresponds in each case to one row of Table A Table 71
Compounds of the formula I.1A*, in which X is N—$CH_2C_6H_5$, $(R^7)_m$ is 4-F and the combination of $R^1$ and $R^6$ for a compound corresponds in each case to one row of Table A Table 72
Compounds of the formula I.1A*, in which X is N—H, $(R^7)_m$ is 5-F and the combination of $R^1$ and $R^6$ for a compound corresponds in each case to one row of Table A Table 73
Compounds of the formula I.1A*, in which X is N—$CH_3$, $(R^7)_m$ is 5-F and the combination of $R^1$ and $R^6$ for a compound corresponds in each case to one row of Table A Table 74
Compounds of the formula I.1A*, in which X is N—$C_2H_5$, $(R^7)_m$ is 5-F and the combination of $R^1$ and $R^6$ for a compound corresponds in each case to one row of Table A Table 75
Compounds of the formula I.1A*, in which X is N-n-$C_3H_7$, $(R^7)_m$ is 5-F and the combination of $R^1$ and $R^6$ for a compound corresponds in each case to one row of Table A Table 76
Compounds of the formula I.1A*, in which X is N—CH($CH_3$)$_2$, $(R^7)_m$ is 5-F and the combination of $R^1$ and $R^6$ for a compound corresponds in each case to one row of Table A Table 77
Compounds of the formula I.1A*, in which X is N-n-$C_4H_9$, $(R^7)_m$ is 5-F and the combination of $R^1$ and $R^6$ for a compound corresponds in each case to one row of Table A Table 78
Compounds of the formula I.1A*, in which X is N—$CH_2CH$=$CH_2$, $(R^7)_m$ is 5-F and the combination of $R^1$ and $R^6$ for a compound corresponds in each case to one row of Table A Table 79
Compounds of the formula I.1A*, in which X is N—$CH_2C$≡$CH$, $(R^7)_m$ is 5-F and the combination of $R^1$ and $R^6$ for a compound corresponds in each case to one row of Table A Table 80
Compounds of the formula I.1A*, in which X is N—$CH_2CN$, $(R^7)_m$ is 5-F and the combination of $R^1$ and $R^6$ for a compound corresponds in each case to one row of Table A Table 81
Compounds of the formula I.1A*, in which X is N—$CH_2CF_3$, $(R^7)_m$ is 5-F and the combination of $R^1$ and $R^6$ for a compound corresponds in each case to one row of Table A Table 82
Compounds of the formula I.1A*, in which X is N—$CH_2C_6H_5$, $(R^7)_m$ is 5-F and the combination of $R^1$ and $R^6$ for a compound corresponds in each case to one row of Table A Table 83
Compounds of the formula I.1A*, in which X is N—H, $(R^7)_m$ is 6-F and the combination of $R^1$ and $R^6$ for a compound corresponds in each case to one row of Table A Table 84
Compounds of the formula I.1A*, in which X is N—$CH_3$, $(R^7)_m$ is 6-F and the combination of $R^1$ and $R^6$ for a compound corresponds in each case to one row of Table A Table 85
Compounds of the formula I.1A*, in which X is N—$C_2H_5$, $(R^7)_m$ is 6-F and the combination of $R^1$ and $R^6$ for a compound corresponds in each case to one row of Table A Table 86
Compounds of the formula I.1A*, in which X is N-n-$C_3H_7$, $(R^7)_m$ is 6-F and the combination of $R^1$ and $R^6$ for a compound corresponds in each case to one row of Table A Table 87
Compounds of the formula I.1A*, in which X is N—CH($CH_3$)$_2$, $(R^7)_m$ is 6-F and the combination of $R^1$ and $R^6$ for a compound corresponds in each case to one row of Table A Table 88
Compounds of the formula I.1A*, in which X is N-n-$C_4H_9$, $(R^7)_m$ is 6-F and the combination of $R^1$ and $R^6$ for a compound corresponds in each case to one row of Table A Table 89
Compounds of the formula I.1A*, in which X is N—$CH_2CH$=$CH_2$, $(R^7)_m$ is 6-F and the combination of $R^1$ and $R^6$ for a compound corresponds in each case to one row of Table A Table 90
Compounds of the formula I.1A*, in which X is N—$CH_2C$≡$CH$, $(R^7)_m$ is 6-F and the combination of $R^1$ and $R^6$ for a compound corresponds in each case to one row of Table A Table 91
Compounds of the formula I.1A*, in which X is N—$CH_2CN$, $(R^7)_m$ is 6-F and the combination of $R^1$ and $R^6$ for a compound corresponds in each case to one row of Table A Table 92
Compounds of the formula I.1A*, in which X is N—$CH_2CF_3$, $(R^7)_m$ is 6-F and the combination of $R^1$ and $R^6$ for a compound corresponds in each case to one row of Table A Table 93
Compounds of the formula I.1A*, in which X is N—$CH_2C_6H_5$, $(R^7)_m$ is 6-F and the combination of $R^1$ and $R^6$ for a compound corresponds in each case to one row of Table A Table 94
Compounds of the formula I.1A*, in which X is N—H, $(R^7)_m$ is 4-$CF_3$ and the combination of $R^1$ and $R^6$ for a compound corresponds in each case to one row of Table A Table 95
Compounds of the formula I.1A*, in which X is N—$CH_3$, $(R^7)_m$ is 4-$CF_3$ and the combination of $R^1$ and $R^6$ for a compound corresponds in each case to one row of Table A Table 96
Compounds of the formula I.1A*, in which X is N—$C_2H_5$, $(R^7)_m$ is 4-$CF_3$ and the combination of $R^1$ and $R^6$ for a compound corresponds in each case to one row of Table A Table 97
Compounds of the formula I.1A*, in which X is N-n-$C_3H_7$, $(R^7)_m$ is 4-$CF_3$ and the combination of $R^1$ and $R^6$ for a compound corresponds in each case to one row of Table A Table 98
Compounds of the formula I.1A*, in which X is N—CH($CH_3$)$_2$, $(R^7)_m$ is 4-$CF_3$ and the combination of $R^1$ and $R^6$ for a compound corresponds in each case to one row of Table A Table 99
Compounds of the formula I.1A*, in which X is N-n-$C_4H_9$, $(R^7)_m$ is 4-$CF_3$ and the combination of $R^1$ and $R^6$ for a compound corresponds in each case to one row of Table A Table 100
Compounds of the formula I.1A*, in which X is N—$CH_2CH$=$CH_2$, $(R^7)_m$ is 4-$CF_3$ and the combination of $R^1$ and $R^6$ for a compound corresponds in each case to one row of Table A Table 101
Compounds of the formula I.1A*, in which X is N—$CH_2C$≡CH, $(R^7)_m$ is 4-$CF_3$ and the combination of $R^1$ and $R^6$ for a compound corresponds in each case to one row of Table A Table 102
Compounds of the formula I.1A*, in which X is N—$CH_2CN$, $(R^7)_m$ is 4-$CF_3$ and the combination of $R^1$ and $R^6$ for a compound corresponds in each case to one row of Table A Table 103
Compounds of the formula I.1A*, in which X is N—$CH_2CF_3$, $(R^7)_m$ is 4-$CF_3$ and the combination of $R^1$ and $R^6$ for a compound corresponds in each case to one row of Table A Table 104
Compounds of the formula I.1A*, in which X is N—$CH_2C_6H_5$, $(R^7)_m$ is 4-$CF_3$ and the combination of $R^1$ and $R^6$ for a compound corresponds in each case to one row of Table A Table 105
Compounds of the formula I.1A*, in which X is N—H, $(R^7)_m$ is 5-$CF_3$ and the combination of $R^1$ and $R^6$ for a compound corresponds in each case to one row of Table A Table 106
Compounds of the formula I.1A*, in which X is N—$CH_3$, $(R^7)_m$ is 5-$CF_3$ and the combination of $R^1$ and $R^6$ for a compound corresponds in each case to one row of Table A Table 107
Compounds of the formula I.1A*, in which X is N—$C_2H_5$, $(R^7)_m$ is 5-$CF_3$ and the combination of $R^1$ and $R^6$ for a compound corresponds in each case to one row of Table A Table 108
Compounds of the formula I.1A*, in which X is N-n-$C_3H_7$, $(R^7)_m$ is 5-$CF_3$ and the combination of $R^1$ and $R^6$ for a compound corresponds in each case to one row of Table A Table 109
Compounds of the formula I.1A*, in which X is N—CH($CH_3$)$_2$, $(R^7)_m$ is 5-$CF_3$ and the combination of $R^1$ and $R^6$ for a compound corresponds in each case to one row of Table A Table 110
Compounds of the formula I.1A*, in which X is N-n-$C_4H_9$, $(R^7)_m$ is 5-$CF_3$ and the combination of $R^1$ and $R^6$ for a compound corresponds in each case to one row of Table A Table 111
Compounds of the formula I.1A*, in which X is N—$CH_2CH$=$CH_2$, $(R^7)_m$ is 5-$CF_3$ and the combination of $R^1$ and $R^6$ for a compound corresponds in each case to one row of Table A Table 112
Compounds of the formula I.1A*, in which X is N—$CH_2C$≡CH, $(R^7)_m$ is 5-$CF_3$ and the combination of $R^1$ and $R^6$ for a compound corresponds in each case to one row of Table A Table 113
Compounds of the formula I.1A*, in which X is N—$CH_2CN$, $(R^7)_m$ is 5-$CF_3$ and the combination of $R^1$ and $R^6$ for a compound corresponds in each case to one row of Table A Table 114
Compounds of the formula I.1A*, in which X is N—$CH_2CF_3$, $(R^7)_m$ is 5-$CF_3$ and the combination of $R^1$ and $R^6$ for a compound corresponds in each case to one row of Table A Table 115
Compounds of the formula I.1A*, in which X is N—$CH_2C_6H_5$, $(R^7)_m$ is 5-$CF_3$ and the combination of $R^1$ and $R^6$ for a compound corresponds in each case to one row of Table A Table 116
Compounds of the formula I.1A*, in which X is N—H, $(R^7)_m$ is 3,6-$F_2$ and the combination of $R^1$ and $R^6$ for a compound corresponds in each case to one row of Table A Table 117
Compounds of the formula I.1A*, in which X is N—$CH_3$, $(R^7)_m$ is 3,6-$F_2$ and the combination of $R^1$ and $R^6$ for a compound corresponds in each case to one row of Table A Table 118
Compounds of the formula I.1A*, in which X is N—$C_2H_5$, $(R^7)_m$ is 3,6-$F_2$ and the combination of $R^1$ and $R^6$ for a compound corresponds in each case to one row of Table A Table 119
Compounds of the formula I.1A*, in which X is N-n-$C_3H_7$, $(R^7)_m$ is 3,6-$F_2$ and the combination of $R^1$ and $R^6$ for a compound corresponds in each case to one row of Table A Table 120
Compounds of the formula I.1A*, in which X is N—CH($CH_3$)$_2$, $(R^7)_m$ is 3,6-$F_2$ and the combination of $R^1$ and $R^6$ for a compound corresponds in each case to one row of Table A Table 121
Compounds of the formula I.1A*, in which X is N-n-$C_4H_9$, $(R^7)_m$ is 3,6-$F_2$ and the combination of $R^1$ and $R^6$ for a compound corresponds in each case to one row of Table A Table 122
Compounds of the formula I.1A*, in which X is N—$CH_2CH$=$CH_2$, $(R^7)_m$ is 3,6-$F_2$ and the combination of $R^1$ and $R^6$ for a compound corresponds in each case to one row of Table A Table 123
Compounds of the formula I.1A*, in which X is N—$CH_2C$≡CH, $(R^7)_m$ is 3,6-$F_2$ and the combination of $R^1$ and $R^6$ for a compound corresponds in each case to one row of Table A Table 124
Compounds of the formula I.1A*, in which X is N—$CH_2CN$, $(R^7)_m$ is 3,6-$F_2$ and the combination of $R^1$ and $R^6$ for a compound corresponds in each case to one row of Table A Table 125
Compounds of the formula I.1A*, in which X is N—$CH_2CF_3$, $(R^7)_m$ is 3,6-$F_2$ and the combination of $R^1$ and $R^6$ for a compound corresponds in each case to one row of Table A Table 126
Compounds of the formula I.1A*, in which X is N—$CH_2C_6H_5$, $(R^7)_m$ is 3,6-$F_2$ and the combination of $R^1$ and $R^6$ for a compound corresponds in each case to one row of Table A Table 127
Compounds of the formula I.2A*, in which X is oxygen, the index m in $(R^7)_m$ is zero and the combination of $R^1$ and $R^6$ for a compound corresponds in each case to one row of Table A Table 128
Compounds of the formula I.2A*, in which X is oxygen, $(R^7)_m$ is 4-Cl and the combination of $R^1$ and $R^6$ for a compound corresponds in each case to one row of Table A Table 129
Compounds of the formula I.2A*, in which X is oxygen, $(R^7)_m$ is 3-F and the combination of $R^1$ and $R^6$ for a compound corresponds in each case to one row of Table A Table 130
Compounds of the formula I.2A*, in which X is oxygen, $(R^7)_m$ is 4-F and the combination of $R^1$ and $R^6$ for a compound corresponds in each case to one row of Table A Table 131
Compounds of the formula I.2A*, in which X is oxygen, $(R^7)_m$ is 5-F and the combination of $R^1$ and $R^6$ for a compound corresponds in each case to one row of Table A Table 132
Compounds of the formula I.2A*, in which X is oxygen, $(R^7)_m$ is 6-F and the combination of $R^1$ and $R^6$ for a compound corresponds in each case to one row of Table A Table 133
Compounds of the formula I.2A*, in which X is oxygen, $(R^7)_m$ is 4-$CF_3$ and the combination of $R^1$ and $R^6$ for a compound corresponds in each case to one row of Table A Table 134
Compounds of the formula I.2A*, in which X is oxygen, $(R^7)_m$ is 5-$CF_3$ and the combination of $R^1$ and $R^6$ for a compound corresponds in each case to one row of Table A Table 135
Compounds of the formula I.2A*, in which X is oxygen, $(R^7)_m$ is 3,6-$F_2$ and the combination of $R^1$ and $R^6$ for a compound corresponds in each case to one row of Table A Table 136
Compounds of the formula I.2A*, in which X is sulfur, the index m in $(R^7)_m$ is zero and the combination of $R^1$ and $R^6$ for a compound corresponds in each case to one row of Table A Table 137
Compounds of the formula I.2A*, in which X is sulfur, $(R^7)_m$ is 4-Cl and the combination of $R^1$ and $R^6$ for a compound corresponds in each case to one row of Table A Table 138
Compounds of the formula I.2A*, in which X is sulfur, $(R^7)_m$ is 3-F and the combination of $R^1$ and $R^6$ for a compound corresponds in each case to one row of Table A Table 139
Compounds of the formula I.2A*, in which X is sulfur, $(R^7)_m$ is 4-F and the combination of $R^1$ and $R^6$ for a compound corresponds in each case to one row of Table A Table 140
Compounds of the formula I.2A*, in which X is sulfur, $(R^7)_m$ is 5-F and the combination of $R^1$ and $R^6$ for a compound corresponds in each case to one row of Table A Table 141
Compounds of the formula I.2A*, in which X is sulfur, $(R^7)_m$ is 6-F and the combination of $R^1$ and $R^6$ for a compound corresponds in each case to one row of Table A Table 142
Compounds of the formula I.2A*, in which X is sulfur, $(R^7)_m$ is 4-$CF_3$ and the combination of $R^1$ and $R^6$ for a compound corresponds in each case to one row of Table A Table 143
Compounds of the formula I.2A*, in which X is sulfur, $(R^7)_m$ is 5-$CF_3$ and the combination of $R^1$ and $R^6$ for a compound corresponds in each case to one row of Table A Table 144
Compounds of the formula I.2A*, in which X is sulfur, $(R^7)_m$ is 3,6-$F_2$ and the combination of $R^1$ and $R^6$ for a compound corresponds in each case to one row of Table A Table 145
Compounds of the formula I.2A*, in which X is sulfur, the index m in $(R^7)_m$ is zero and the combination of $R^1$ and $R^6$ for a compound corresponds in each case to one row of Table A Table 146
Compounds of the formula I.2A*, in which X is sulfur, $(R^7)_m$ is 4-Cl and the combination of $R^1$ and $R^6$ for a compound corresponds in each case to one row of Table A Table 147
Compounds of the formula I.2A*, in which X is sulfur, $(R^7)_m$ is 3-F and the combination of $R^1$ and $R^6$ for a compound corresponds in each case to one row of Table A Table 148
Compounds of the formula I.2A*, in which X is sulfur, $(R^7)_m$ is 4-F and the combination of $R^1$ and $R^6$ for a compound corresponds in each case to one row of Table A Table 149
Compounds of the formula I.2A*, in which X is sulfur, $(R^7)_m$ is 5-F and the combination of $R^1$ and $R^6$ for a compound corresponds in each case to one row of Table A Table 150
Compounds of the formula I.2A*, in which X is sulfur, $(R^7)_m$ is 6-F and the combination of $R^1$ and $R^6$ for a compound corresponds in each case to one row of Table A Table 151
Compounds of the formula I.2A*, in which X is sulfur, $(R^7)_m$ is 4-$CF_3$ and the combination of $R^1$ and $R^6$ for a compound corresponds in each case to one row of Table A Table 152
Compounds of the formula I.2A*, in which X is sulfur, $(R^7)_m$ is 5-$CF_3$ and the combination of $R^1$ and $R^6$ for a compound corresponds in each case to one row of Table A Table 153
Compounds of the formula I.2A*, in which X is sulfur, $(R^7)_m$ is 3,6-$F_2$ and the combination of $R^1$ and $R^6$ for a compound corresponds in each case to one row of Table A Table 154
Compounds of the formula I.2A*, in which X is N—H, the index m in $(R^7)_m$ is zero and the combination of $R^1$ and $R^6$ for a compound corresponds in each case to one row of Table A Table 155
Compounds of the formula I.2A*, in which X is N—$CH_3$, the index m in $(R^7)_m$ is zero and the combination of $R^1$ and $R^6$ for a compound corresponds in each case to one row of Table A Table 156
Compounds of the formula I.2A*, in which X is N—$C_2H_5$, the index m in $(R^7)_m$ is zero and the combination of $R^1$ and $R^6$ for a compound corresponds in each case to one row of Table A Table 157
Compounds of the formula I.2A*, in which X is N-n-$C_3H_7$, the index m in $(R^7)_m$ is zero and the combination of $R^1$ and $R^6$ for a compound corresponds in each case to one row of Table A Table 158
Compounds of the formula I.2A*, in which X is N—CH$(CH_3)_2$, the index m in $(R^7)_m$ is zero and the combination of $R^1$ and $R^6$ for a compound corresponds in each case to one row of Table A Table 159
Compounds of the formula I.2A*, in which X is N-n-$C_4H_9$, the index m in $(R^7)_m$ is zero and the combination of $R^1$ and $R^6$ for a compound corresponds in each case to one row of Table A Table 160
Compounds of the formula I.2A*, in which X is N—$CH_2CH$=$CH_2$, the index m in $(R^7)_m$ is zero and the combination of $R^1$ and $R^6$ for a compound corresponds in each case to one row of Table A Table 161
Compounds of the formula I.2A*, in which X is N—$CH_2C$≡$CH$, the index m in $(R^7)_m$ is zero and the combination of $R^1$ and $R^6$ for a compound corresponds in each case to one row of Table A Table 162
Compounds of the formula I.2A*, in which X is N—$CH_2CN$, the index m in $(R^7)_m$ is zero and the combination of $R^1$ and $R^6$ for a compound corresponds in each case to one row of Table A Table 163
Compounds of the formula I.2A*, in which X is N—$CH_2CF_3$, the index m in $(R^7)_m$ is zero and the combination of $R^1$ and $R^6$ for a compound corresponds in each case to one row of Table A Table 164
Compounds of the formula I.2A*, in which X is N—$CH_2C_6H_5$, the index m in $(R^7)_m$ is zero and the combination of $R^1$ and $R^6$ for a compound corresponds in each case to one row of Table A Table 165
Compounds of the formula I.2A*, in which X is N—H, $(R^7)_m$ is 4-Cl and the combination of $R^1$ and $R^6$ for a compound corresponds in each case to one row of Table A Table 166
Compounds of the formula I.2A*, in which X is N—$CH_3$, $(R^7)_m$ is 4-Cl and the combination of $R^1$ and $R^6$ for a compound corresponds in each case to one row of Table A Table 167
Compounds of the formula I.2A*, in which X is N—$C_2H_5$, $(R^7)_m$ is 4-Cl and the combination of $R^1$ and $R^6$ for a compound corresponds in each case to one row of Table A Table 168
Compounds of the formula I.2A*, in which X is N-n-$C_3H_7$, $(R^7)_m$ is 4-Cl and the combination of $R^1$ and $R^6$ for a compound corresponds in each case to one row of Table A Table 169
Compounds of the formula I.2A*, in which X is N—CH($CH_3$)$_2$, $(R^7)_m$ is 4-Cl and the combination of $R^1$ and $R^6$ for a compound corresponds in each case to one row of Table A Table 170
Compounds of the formula I.2A*, in which X is N-n-$C_4H_9$, $(R^7)_m$ is 4-Cl and the combination of $R^1$ and $R^6$ for a compound corresponds in each case to one row of Table A Table 171
Compounds of the formula I.2A*, in which X is N—$CH_2CH$=$CH_2$, $(R^7)_m$ is 4-Cl and the combination of $R^1$ and $R^6$ for a compound corresponds in each case to one row of Table A Table 172
Compounds of the formula I.2A*, in which X is N—$CH_2C$≡$CH$, $(R^7)_m$ is 4-Cl and the combination of $R^1$ and $R^6$ for a compound corresponds in each case to one row of Table A Table 173
Compounds of the formula I.2A*, in which X is N—$CH_2CN$, $(R^7)_m$ is 4-Cl and the combination of $R^1$ and $R^6$ for a compound corresponds in each case to one row of Table A Table 174
Compounds of the formula I.2A*, in which X is N—$CH_2CF_3$, $(R^7)_m$ is 4-Cl and the combination of $R^1$ and $R^6$ for a compound corresponds in each case to one row of Table A Table 175
Compounds of the formula I.2A*, in which X is N—$CH_2C_6H_5$, $(R^7)_m$ is 4-Cl and the combination of $R^1$ and $R^6$ for a compound corresponds in each case to one row of Table A Table 176
Compounds of the formula I.2A*, in which X is N—H, $(R^7)_m$ is 3-F and the combination of $R^1$ and $R^6$ for a compound corresponds in each case to one row of Table A Table 177
Compounds of the formula I.2A*, in which X is N—$CH_3$, $(R^7)_m$ is 3-F and the combination of $R^1$ and $R^6$ for a compound corresponds in each case to one row of Table A Table 178
Compounds of the formula I.2A*, in which X is N—$C_2H_5$, $(R^7)_m$ is 3-F and the combination of $R^1$ and $R^6$ for a compound corresponds in each case to one row of Table A Table 179
Compounds of the formula I.2A*, in which X is N-n-$C_3H_7$, $(R^7)_m$ is 3-F and the combination of $R^1$ and $R^6$ for a compound corresponds in each case to one row of Table A Table 180
Compounds of the formula I.2A*, in which X is N—CH($CH_3$)$_2$, $(R^7)_m$ is 3-F and the combination of $R^1$ and $R^6$ for a compound corresponds in each case to one row of Table A Table 181
Compounds of the formula I.2A*, in which X is N-n-$C_4H_9$, $(R^7)_m$ is 3-F and the combination of $R^1$ and $R^6$ for a compound corresponds in each case to one row of Table A Table 182
Compounds of the formula I.2A*, in which X is N—$CH_2CH$=$CH_2$, $(R^7)_m$ is 3-F and the combination of $R^1$ and $R^6$ for a compound corresponds in each case to one row of Table A Table 183
Compounds of the formula I.2A*, in which X is N—$CH_2C$≡$CH$, $(R^7)_m$ is 3-F and the combination of $R^1$ and $R^6$ for a compound corresponds in each case to one row of Table A Table 184
Compounds of the formula I.2A*, in which X is N—$CH_2CN$, $(R^7)_m$ is 3-F and the combination of $R^1$ and $R^6$ for a compound corresponds in each case to one row of Table A Table 185
Compounds of the formula I.2A*, in which X is N—$CH_2CF_3$, $(R^7)_m$ is 3-F and the combination of $R^1$ and $R^6$ for a compound corresponds in each case to one row of Table A Table 186
Compounds of the formula I.2A*, in which X is N—$CH_2C_6H_5$, $(R^7)_m$ is 3-F and the combination of $R^1$ and $R^6$ for a compound corresponds in each case to one row of Table A Table 187
Compounds of the formula I.2A*, in which X is N—H, $(R^7)_m$ is 4-F and the combination of $R^1$ and $R^6$ for a compound corresponds in each case to one row of Table A Table 188
Compounds of the formula I.2A*, in which X is N—$CH_3$, $(R^7)_m$ is 4-F and the combination of $R^1$ and $R^6$ for a compound corresponds in each case to one row of Table A Table 189
Compounds of the formula I.2A*, in which X is N—$C_2H_5$, $(R^7)_m$ is 4-F and the combination of $R^1$ and $R^6$ for a compound corresponds in each case to one row of Table A Table 190
Compounds of the formula I.2A*, in which X is N-n-$C_3H_7$, $(R^7)_m$ is 4-F and the combination of $R^1$ and $R^6$ for a compound corresponds in each case to one row of Table A Table 191
Compounds of the formula I.2A*, in which X is N—CH$(CH_3)_2$, $(R^7)_m$ is 4-F and the combination of $R^1$ and $R^6$ for a compound corresponds in each case to one row of Table A Table 192
Compounds of the formula I.2A*, in which X is N-n-$C_4H_9$, $(R^7)_m$ is 4-F and the combination of $R^1$ and $R^6$ for a compound corresponds in each case to one row of Table A Table 193
Compounds of the formula I.2A*, in which X is N—$CH_2CH$=$CH_2$, $(R^7)_m$ is 4-F and the combination of $R^1$ and $R^6$ for a compound corresponds in each case to one row of Table A Table 194
Compounds of the formula I.2A*, in which X is N—$CH_2C$≡CH, $(R^7)_m$ is 4-F and the combination of $R^1$ and $R^6$ for a compound corresponds in each case to one row of Table A Table 195
Compounds of the formula I.2A*, in which X is N—$CH_2CN$, $(R^7)_m$ is 4-F and the combination of $R^1$ and $R^6$ for a compound corresponds in each case to one row of Table A Table 196
Compounds of the formula I.2A*, in which X is N—$CH_2CF_3$, $(R^7)_m$ is 4-F and the combination of $R^1$ and $R^6$ for a compound corresponds in each case to one row of Table A Table 197
Compounds of the formula I.2A*, in which X is N—$CH_2C_6H_5$, $(R^7)_m$ is 4-F and the combination of $R^1$ and $R^6$ for a compound corresponds in each case to one row of Table A Table 198
Compounds of the formula I.2A*, in which X is N—H, $(R^7)_m$ is 5-F and the combination of $R^1$ and $R^6$ for a compound corresponds in each case to one row of Table A Table 199
Compounds of the formula I.2A*, in which X is N—$CH_3$, $(R^7)_m$ is 5-F and the combination of $R^1$ and $R^6$ for a compound corresponds in each case to one row of Table A Table 200
Compounds of the formula I.2A*, in which X is N—$C_2H_5$, $(R^7)_m$ is 5-F and the combination of $R^1$ and $R^6$ for a compound corresponds in each case to one row of Table A Table 201
Compounds of the formula I.2A*, in which X is N-n-$C_3H_7$, $(R^7)_m$ is 5-F and the combination of $R^1$ and $R^6$ for a compound corresponds in each case to one row of Table A Table 202
Compounds of the formula I.2A*, in which X is N—CH$(CH_3)_2$, $(R^7)_m$ is 5-F and the combination of $R^1$ and $R^6$ for a compound corresponds in each case to one row of Table A Table 203
Compounds of the formula I.2A*, in which X is N-n-$C_4H_9$, $(R^7)_m$ is 5-F and the combination of $R^1$ and $R^6$ for a compound corresponds in each case to one row of Table A Table 204
Compounds of the formula I.2A*, in which X is N—$CH_2CH$=$CH_2$, $(R^7)_m$ is 5-F and the combination of $R^1$ and $R^6$ for a compound corresponds in each case to one row of Table A Table 205
Compounds of the formula I.2A*, in which X is N—$CH_2C$≡CH, $(R^7)_m$ is 5-F and the combination of $R^1$ and $R^6$ for a compound corresponds in each case to one row of Table A Table 206
Compounds of the formula I.2A*, in which X is N—$CH_2CN$, $(R^7)_m$ is 5-F and the combination of $R^1$ and $R^6$ for a compound corresponds in each case to one row of Table A Table 207
Compounds of the formula I.2A*, in which X is N—$CH_2CF_3$, $(R^7)_m$ is 5-F and the combination of $R^1$ and $R^6$ for a compound corresponds in each case to one row of Table A Table 208
Compounds of the formula I.2A*, in which X is N—$CH_2C_6H_5$, $(R^7)_m$ is 5-F and the combination of $R^1$ and $R^6$ for a compound corresponds in each case to one row of Table A Table 209
Compounds of the formula I.2A*, in which X is N—H, $(R^7)_m$ is 6-F and the combination of $R^1$ and $R^6$ for a compound corresponds in each case to one row of Table A Table 210
Compounds of the formula I.2A*, in which X is N—$CH_3$, $(R^7)_m$ is 6-F and the combination of $R^1$ and $R^6$ for a compound corresponds in each case to one row of Table A Table 211
Compounds of the formula I.2A*, in which X is N—$C_2H_5$, $(R^7)_m$ is 6-F and the combination of $R^1$ and $R^6$ for a compound corresponds in each case to one row of Table A Table 212
Compounds of the formula I.2A*, in which X is N-n-$C_3H_7$, $(R^7)_m$ is 6-F and the combination of $R^1$ and $R^6$ for a compound corresponds in each case to one row of Table A Table 213
Compounds of the formula I.2A*, in which X is N—CH$(CH_3)_2$, $(R^7)_m$ is 6-F and the combination of $R^1$ and $R^6$ for a compound corresponds in each case to one row of Table A Table 214
Compounds of the formula I.2A*, in which X is N-n-$C_4H_9$, $(R^7)_m$ is 6-F and the combination of $R^1$ and $R^6$ for a compound corresponds in each case to one row of Table A Table 215
Compounds of the formula I.2A*, in which X is N—$CH_2CH$=$CH_2$, $(R^7)_m$ is 6-F and the combination of $R^1$ and $R^6$ for a compound corresponds in each case to one row of Table A Table 216
Compounds of the formula I.2A*, in which X is N—$CH_2C$≡CH, $(R^7)_m$ is 6-F and the combination of $R^1$ and $R^6$ for a compound corresponds in each case to one row of Table A Table 217
Compounds of the formula I.2A*, in which X is N—$CH_2CN$, $(R^7)_m$ is 6-F and the combination of $R^1$ and $R^6$ for a compound corresponds in each case to one row of Table A Table 218
Compounds of the formula I.2A*, in which X is N—$CH_2CF_3$, $(R^7)_m$ is 6-F and the combination of $R^1$ and $R^6$ for a compound corresponds in each case to one row of Table A Table 219
Compounds of the formula I.2A*, in which X is N—CH$_2$C$_6$H$_5$, (R$^7$)$_m$ is 6-F and the combination of R$^1$ and R$^6$ for a compound corresponds in each case to one row of Table A Table 220
Compounds of the formula I.2A*, in which X is N—H, (R$^7$)$_m$ is 4-CF$_3$ and the combination of R$^1$ and R$^6$ for a compound corresponds in each case to one row of Table A Table 221
Compounds of the formula I.2A*, in which X is N—CH$_3$, (R$^7$)$_m$ is 4-CF$_3$ and the combination of R$^1$ and R$^6$ for a compound corresponds in each case to one row of Table A Table 222
Compounds of the formula I.2A*, in which X is N—C$_2$H$_5$, (R$^7$)$_m$ is 4-CF$_3$ and the combination of R$^1$ and R$^6$ for a compound corresponds in each case to one row of Table A Table 223
Compounds of the formula I.2A*, in which X is N-n-C$_3$H$_7$, (R$^7$)$_m$ is 4-CF$_3$ and the combination of R$^1$ and R$^6$ for a compound corresponds in each case to one row of Table A Table 224
Compounds of the formula I.2A*, in which X is N—CH(CH$_3$)$_2$, (R$^7$)$_m$ is 4-CF$_3$ and the combination of R$^1$ and R$^6$ for a compound corresponds in each case to one row of Table A Table 225
Compounds of the formula I.2A*, in which X is N-n-C$_4$H$_9$, (R$^7$)$_m$ is 4-CF$_3$ and the combination of R$^1$ and R$^6$ for a compound corresponds in each case to one row of Table A Table 226
Compounds of the formula I.2A*, in which X is N—CH$_2$CH=CH$_2$, (R$^7$)$_m$ is 4-CF$_3$ and the combination of R$^1$ and R$^6$ for a compound corresponds in each case to one row of Table A Table 227
Compounds of the formula I.2A*, in which X is N—CH$_2$C≡CH, (R$^7$)$_m$ is 4-CF$_3$ and the combination of R$^1$ and R$^6$ for a compound corresponds in each case to one row of Table A Table 228
Compounds of the formula I.2A*, in which X is N—CH$_2$CN, (R$^7$)$_m$ is 4-CF$_3$ and the combination of R$^1$ and R$^6$ for a compound corresponds in each case to one row of Table A Table 229
Compounds of the formula I.2A*, in which X is N—CH$_2$CF$_3$, (R$^7$)$_m$ is 4-CF$_3$ and the combination of R$^1$ and R$^6$ for a compound corresponds in each case to one row of Table A Table 230
Compounds of the formula I.2A*, in which X is N—CH$_2$C$_6$H$_5$, (R$^7$)$_m$ is 4-CF$_3$ and the combination of R$^1$ and R$^6$ for a compound corresponds in each case to one row of Table A Table 231
Compounds of the formula I.2A*, in which X is N—H, (R$^7$)$_m$ is 5-CF$_3$ and the combination of R$^1$ and R$^6$ for a compound corresponds in each case to one row of Table A Table 232
Compounds of the formula I.2A*, in which X is N—CH$_3$, (R$^7$)$_m$ is 5-CF$_3$ and the combination of R$^1$ and R$^6$ for a compound corresponds in each case to one row of Table A Table 233
Compounds of the formula I.2A*, in which X is N—C$_2$H$_5$, (R$^7$)$_m$ is 5-CF$_3$ and the combination of R$^1$ and R$^6$ for a compound corresponds in each case to one row of Table A Table 234
Compounds of the formula I.2A*, in which X is N-n-C$_3$H$_7$, (R$^7$)$_m$ is 5-CF$_3$ and the combination of R$^1$ and R$^6$ for a compound corresponds in each case to one row of Table A Table 235
Compounds of the formula I.2A*, in which X is N—CH(CH$_3$)$_2$, (R$^7$)$_m$ is 5-CF$_3$ and the combination of R$^1$ and R$^6$ for a compound corresponds in each case to one row of Table A Table 236
Compounds of the formula I.2A*, in which X is N-n-C$_4$H$_9$, (R$^7$)$_m$ is 5-CF$_3$ and the combination of R$^1$ and R$^6$ for a compound corresponds in each case to one row of Table A Table 237
Compounds of the formula I.2A*, in which X is N—CH$_2$CH=CH$_2$, (R$^7$)$_m$ is 5-CF$_3$ and the combination of R$^1$ and R$^6$ for a compound corresponds in each case to one row of Table A Table 238
Compounds of the formula I.2A*, in which X is N—CH$_2$C≡CH, (R$^7$)$_m$ is 5-CF$_3$ and the combination of R$^1$ and R$^6$ for a compound corresponds in each case to one row of Table A Table 239
Compounds of the formula I.2A*, in which X is N—CH$_2$CN, (R$^7$)$_m$ is 5-CF$_3$ and the combination of R$^1$ and R$^6$ for a compound corresponds in each case to one row of Table A Table 240
Compounds of the formula I.2A*, in which X is N—CH$_2$CF$_3$, (R$^7$)$_m$ is 5-CF$_3$ and the combination of R$^1$ and R$^6$ for a compound corresponds in each case to one row of Table A Table 241
Compounds of the formula I.2A*, in which X is N—CH$_2$C$_6$H$_5$, (R$^7$)$_m$ is 5-CF$_3$ and the combination of R$^1$ and R$^6$ for a compound corresponds in each case to one row of Table A Table 242
Compounds of the formula I.2A*, in which X is N—H, (R$^7$)$_m$ is 3,6-F$_2$ and the combination of R$^1$ and R$^6$ for a compound corresponds in each case to one row of Table A Table 243
Compounds of the formula I.2A*, in which X is N—CH$_3$, (R$^7$)$_m$ is 3,6-F$_2$ and the combination of R$^1$ and R$^6$ for a compound corresponds in each case to one row of Table A Table 244
Compounds of the formula I.2A*, in which X is N—C$_2$H$_5$, (R$^7$)$_m$ is 3,6-F$_2$ and the combination of R$^1$ and R$^6$ for a compound corresponds in each case to one row of Table A Table 245
Compounds of the formula I.2A*, in which X is N-n-C$_3$H$_7$, (R$^7$)$_m$ is 3,6-F$_2$ and the combination of R$^1$ and R$^6$ for a compound corresponds in each case to one row of Table A Table 246
Compounds of the formula I.2A*, in which X is N—CH(CH$_3$)$_2$, (R$^7$)$_m$ is 3,6-F$_2$ and the combination of R$^1$ and R$^6$ for a compound corresponds in each case to one row of Table A Table 247
Compounds of the formula I.2A*, in which X is N-n-C$_4$H$_9$, (R$^7$)$_m$ is 3,6-F$_2$ and the combination of R$^1$ and R$^6$ for a compound corresponds in each case to one row of Table A Table 248
Compounds of the formula I.2A*, in which X is N—CH$_2$CH=CH$_2$, (R$^7$)$_m$ is 3,6-F$_2$ and the combination of R$^1$ and R$^6$ for a compound corresponds in each case to one row of Table A Table 249
Compounds of the formula I.2A*, in which X is N—CH$_2$C≡CH, $(R^7)_m$ is 3,6-F$_2$ and the combination of R$^1$ and R$^6$ for a compound corresponds in each case to one row of Table A Table 250
Compounds of the formula I.2A*, in which X is N—CH$_2$CN, $(R^7)_m$ is 3,6-F$_2$ and the combination of R$^1$ and R$^6$ for a compound corresponds in each case to one row of Table A Table 251
Compounds of the formula I.2A*, in which X is N—CH$_2$CF$_3$, $(R^7)_m$ is 3,6-F$_2$ and the combination of R$^1$ and R$^6$ for a compound corresponds in each case to one row of Table A Table 252
Compounds of the formula I.2A*, in which X is N—CH$_2$C$_6$H$_5$, $(R^7)_m$ is 3,6-F$_2$ and the combination of R$^1$ and R$^6$ for a compound corresponds in each case to one row of Table A Table 253
Compounds of the formula I.3A*, in which X is oxygen, the index m in $(R^7)_m$ is zero and the combination of R$^1$ and R$^6$ for a compound corresponds in each case to one row of Table A Table 254
Compounds of the formula I.3A*, in which X is oxygen, $(R^7)_m$ is 4-Cl and the combination of R$^1$ and R$^6$ for a compound corresponds in each case to one row of Table A Table 255
Compounds of the formula I.3A*, in which X is oxygen, $(R^7)_m$ is 3-F and the combination of R$^1$ and R$^6$ for a compound corresponds in each case to one row of Table A Table 256
Compounds of the formula I.3A*, in which X is oxygen, $(R^7)_m$ is 4-F and the combination of R$^1$ and R$^6$ for a compound corresponds in each case to one row of Table A Table 257
Compounds of the formula I.3A*, in which X is oxygen, $(R^7)_m$ is 5-F and the combination of R$^1$ and R$^6$ for a compound corresponds in each case to one row of Table A Table 258
Compounds of the formula I.3A*, in which X is oxygen, $(R^7)_m$ is 6-F and the combination of R$^1$ and R$^6$ for a compound corresponds in each case to one row of Table A Table 259
Compounds of the formula I.3A*, in which X is oxygen, $(R^7)_m$ is 4-CF$_3$ and the combination of R$^1$ and R$^6$ for a compound corresponds in each case to one row of Table A Table 260
Compounds of the formula I.3A*, in which X is oxygen, $(R^7)_m$ is 5-CF$_3$ and the combination of R$^1$ and R$^6$ for a compound corresponds in each case to one row of Table A Table 261
Compounds of the formula I.3A*, in which X is oxygen, $(R^7)_m$ is 3,6-F$_2$ and the combination of R$^1$ and R$^6$ for a compound corresponds in each case to one row of Table A Table 262
Compounds of the formula I.3A*, in which X is sulfur, the index m in $(R^7)_m$ is zero and the combination of R$^1$ and R$^6$ for a compound corresponds in each case to one row of Table A Table 263
Compounds of the formula I.3A*, in which X is sulfur, $(R^7)_m$ is 4-Cl and the combination of R$^1$ and R$^6$ for a compound corresponds in each case to one row of Table A Table 264
Compounds of the formula I.3A*, in which X is sulfur, $(R^7)_m$ is 3-F and the combination of R$^1$ and R$^6$ for a compound corresponds in each case to one row of Table A Table 265
Compounds of the formula I.3A*, in which X is sulfur, $(R^7)_m$ is 4-F and the combination of R$^1$ and R$^6$ for a compound corresponds in each case to one row of Table A Table 266
Compounds of the formula I.3A*, in which X is sulfur, $(R^7)_m$ is 5-F and the combination of R$^1$ and R$^6$ for a compound corresponds in each case to one row of Table A Table 267
Compounds of the formula I.3A*, in which X is sulfur, $(R^7)_m$ is 6-F and the combination of W and R$^6$ for a compound corresponds in each case to one row of Table A Table 268
Compounds of the formula I.3A*, in which X is sulfur, $(R^7)_m$ is 4-CF$_3$ and the combination of W and R$^6$ for a compound corresponds in each case to one row of Table A Table 269
Compounds of the formula I.3A*, in which X is sulfur, $(R^7)_m$ is 5-CF$_3$ and the combination of R$^1$ and R$^6$ for a compound corresponds in each case to one row of Table A Table 270
Compounds of the formula I.3A*, in which X is sulfur, $(R^7)_m$ is 3,6-F$_2$ and the combination of R$^1$ and R$^6$ for a compound corresponds in each case to one row of Table A Table 271
Compounds of the formula I.3A*, in which X is sulfur, the index m in $(R^7)_m$ is zero and the combination of R$^1$ and R$^6$ for a compound corresponds in each case to one row of Table A Table 272
Compounds of the formula I.3A*, in which X is sulfur, $(R^7)_m$ is 4-Cl and the combination of R$^1$ and R$^6$ for a compound corresponds in each case to one row of Table A Table 273
Compounds of the formula I.3A*, in which X is sulfur, $(R^7)_m$ is 3-F and the combination of R$^1$ and R$^6$ for a compound corresponds in each case to one row of Table A Table 274
Compounds of the formula I.3A*, in which X is sulfur, $(R^7)_m$ is 4-F and the combination of R$^1$ and R$^6$ for a compound corresponds in each case to one row of Table A Table 275
Compounds of the formula I.3A*, in which X is sulfur, $(R^7)_m$ is 5-F and the combination of R$^1$ and R$^6$ for a compound corresponds in each case to one row of Table A Table 276
Compounds of the formula I.3A*, in which X is sulfur, $(R^7)_m$ is 6-F and the combination of R$^1$ and R$^6$ for a compound corresponds in each case to one row of Table A Table 277
Compounds of the formula I.3A*, in which X is sulfur, $(R^7)_m$ is 4-CF$_3$ and the combination of R$^1$ and R$^6$ for a compound corresponds in each case to one row of Table A Table 278
Compounds of the formula I.3A*, in which X is sulfur, $(R^7)_m$ is 5-CF$_3$ and the combination of R$^1$ and R$^6$ for a compound corresponds in each case to one row of Table A Table 279
Compounds of the formula I.3A*, in which X is sulfur, $(R^7)_m$ is 3,6-F$_2$ and the combination of W and R$^6$ for a compound corresponds in each case to one row of Table A Table 280
Compounds of the formula I.3A*, in which X is N—H, the index m in $(R^7)_m$ is zero and the combination of W and R$^6$ for a compound corresponds in each case to one row of Table A Table 281
Compounds of the formula I.3A*, in which X is N—CH$_3$, the index m in $(R^7)_m$ is zero and the combination of R$^1$ and R$^6$ for a compound corresponds in each case to one row of Table A Table 282
Compounds of the formula I.3A*, in which X is N—$C_2H_5$, the index m in $(R^7)_m$ is zero and the combination of $R^1$ and $R^6$ for a compound corresponds in each case to one row of Table A Table 283
Compounds of the formula I.3A*, in which X is N-n-$C_3H_7$, the index m in $(R^7)_m$ is zero and the combination of $R^1$ and $R^6$ for a compound corresponds in each case to one row of Table A Table 284
Compounds of the formula I.3A*, in which X is N—CH$(CH_3)_2$, the index m in $(R^7)_m$ is zero and the combination of $R^1$ and $R^6$ for a compound corresponds in each case to one row of Table A Table 285
Compounds of the formula I.3A*, in which X is N-n-$C_4H_9$, the index m in $(R^7)_m$ is zero and the combination of $R^1$ and $R^6$ for a compound corresponds in each case to one row of Table A Table 286
Compounds of the formula I.3A*, in which X is N—$CH_2CH$=$CH_2$, the index m in $(R^7)_m$ is zero and the combination of $R^1$ and $R^6$ for a compound corresponds in each case to one row of Table A Table 287
Compounds of the formula I.3A*, in which X is N—$CH_2C$≡CH, the index m in $(R^7)_m$ is zero and the combination of $R^1$ and $R^6$ for a compound corresponds in each case to one row of Table A Table 288
Compounds of the formula I.3A*, in which X is N—$CH_2CN$, the index m in $(R^7)_m$ is zero and the combination of $R^1$ and $R^6$ for a compound corresponds in each case to one row of Table A Table 289
Compounds of the formula I.3A*, in which X is N—$CH_2CF_3$, the index m in $(R^7)_m$ is zero and the combination of $R^1$ and $R^6$ for a compound corresponds in each case to one row of Table A Table 290
Compounds of the formula I.3A*, in which X is N—$CH_2C_6H_5$, the index m in $(R^7)_m$ is zero and the combination of $R^1$ and $R^6$ for a compound corresponds in each case to one row of Table A Table 291
Compounds of the formula I.3A*, in which X is N—H, $(R^7)_m$ is 4-Cl and the combination of $R^1$ and $R^6$ for a compound corresponds in each case to one row of Table A Table 292
Compounds of the formula I.3A*, in which X is N—$CH_3$, $(R^7)_m$ is 4-Cl and the combination of $R^1$ and $R^6$ for a compound corresponds in each case to one row of Table A Table 293
Compounds of the formula I.3A*, in which X is N—$C_2H_5$, $(R^7)_m$ is 4-Cl and the combination of $R^1$ and $R^6$ for a compound corresponds in each case to one row of Table A Table 294
Compounds of the formula I.3A*, in which X is N-n-$C_3H_7$, $(R^7)_m$ is 4-Cl and the combination of $R^1$ and $R^6$ for a compound corresponds in each case to one row of Table A Table 295
Compounds of the formula I.3A*, in which X is N—CH$(CH_3)_2$, $(R^7)_m$ is 4-Cl and the combination of $R^1$ and $R^6$ for a compound corresponds in each case to one row of Table A Table 296
Compounds of the formula I.3A*, in which X is N-n-$C_4H_9$, $(R^7)_m$ is 4-Cl and the combination of $R^1$ and $R^6$ for a compound corresponds in each case to one row of Table A Table 297
Compounds of the formula I.3A*, in which X is N—$CH_2CH$=$CH_2$, $(R^7)_m$ is 4-Cl and the combination of $R^1$ and $R^6$ for a compound corresponds in each case to one row of Table A Table 298
Compounds of the formula I.3A*, in which X is N—$CH_2C$≡CH, $(R^7)_m$ is 4-Cl and the combination of $R^1$ and $R^6$ for a compound corresponds in each case to one row of Table A Table 299
Compounds of the formula I.3A*, in which X is N—$CH_2CN$, $(R^7)_m$ is 4-Cl and the combination of $R^1$ and $R^6$ for a compound corresponds in each case to one row of Table A Table 300
Compounds of the formula I.3A*, in which X is N—$CH_2CF_3$, $(R^7)_m$ is 4-Cl and the combination of $R^1$ and $R^6$ for a compound corresponds in each case to one row of Table A Table 301
Compounds of the formula I.3A*, in which X is N—$CH_2C_6H_5$, $(R^7)_m$ is 4-Cl and the combination of $R^1$ and $R^6$ for a compound corresponds in each case to one row of Table A Table 302
Compounds of the formula I.3A*, in which X is N—H, $(R^7)_m$ is 3-F and the combination of $R^1$ and $R^6$ for a compound corresponds in each case to one row of Table A Table 303
Compounds of the formula I.3A*, in which X is N—$CH_3$, $(R^7)_m$ is 3-F and the combination of $R^1$ and $R^6$ for a compound corresponds in each case to one row of Table A Table 304
Compounds of the formula I.3A*, in which X is N—$C_2H_5$, $(R^7)_m$ is 3-F and the combination of $R^1$ and $R^6$ for a compound corresponds in each case to one row of Table A Table 305
Compounds of the formula I.3A*, in which X is N-n-$C_3H_7$, $(R^7)_m$ is 3-F and the combination of $R^1$ and $R^6$ for a compound corresponds in each case to one row of Table A Table 306
Compounds of the formula I.3A*, in which X is N—CH$(CH_3)_2$, $(R^7)_m$ is 3-F and the combination of $R^1$ and $R^6$ for a compound corresponds in each case to one row of Table A Table 307
Compounds of the formula I.3A*, in which X is N-n-$C_4H_9$, $(R^7)_m$ is 3-F and the combination of $R^1$ and $R^6$ for a compound corresponds in each case to one row of Table A Table 308
Compounds of the formula I.3A*, in which X is N—$CH_2CH$=$CH_2$, $(R^7)_m$ is 3-F and the combination of $R^1$ and $R^6$ for a compound corresponds in each case to one row of Table A Table 309
Compounds of the formula I.3A*, in which X is N—$CH_2C$≡CH, $(R^7)_m$ is 3-F and the combination of $R^1$ and $R^6$ for a compound corresponds in each case to one row of Table A Table 310
Compounds of the formula I.3A*, in which X is N—$CH_2CN$, $(R^7)_m$ is 3-F and the combination of $R^1$ and $R^6$ for a compound corresponds in each case to one row of Table A Table 311
Compounds of the formula I.3A*, in which X is N—CH$_2$CF$_3$, (R$^7$)$_m$ is 3-F and the combination of R$^1$ and R$^6$ for a compound corresponds in each case to one row of Table A Table 312
Compounds of the formula I.3A*, in which X is N—CH$_2$C$_6$H$_5$, (R$^7$)$_m$ is 3-F and the combination of R$^1$ and R$^6$ for a compound corresponds in each case to one row of Table A Table 313
Compounds of the formula I.3A*, in which X is N—H, (R$^7$)$_m$ is 4-F and the combination of R$^1$ and R$^6$ for a compound corresponds in each case to one row of Table A Table 314
Compounds of the formula I.3A*, in which X is N—CH$_3$, (R$^7$)$_m$ is 4-F and the combination of R$^1$ and R$^6$ for a compound corresponds in each case to one row of Table A Table 315
Compounds of the formula I.3A*, in which X is N—C$_2$H$_5$, (R$^7$)$_m$ is 4-F and the combination of R$^1$ and R$^6$ for a compound corresponds in each case to one row of Table A Table 316
Compounds of the formula I.3A*, in which X is N-n-C$_3$H$_7$, (R$^7$)$_m$ is 4-F and the combination of R$^1$ and R$^6$ for a compound corresponds in each case to one row of Table A Table 317
Compounds of the formula I.3A*, in which X is N—CH(CH$_3$)$_2$, (R$^7$)$_m$ is 4-F and the combination of R$^1$ and R$^6$ for a compound corresponds in each case to one row of Table A Table 318
Compounds of the formula I.3A*, in which X is N-n-C$_4$H$_9$, (R$^7$)$_m$ is 4-F and the combination of R$^1$ and R$^6$ for a compound corresponds in each case to one row of Table A Table 319
Compounds of the formula I.3A*, in which X is N—CH$_2$CH═CH$_2$, (R$^7$)$_m$ is 4-F and the combination of R$^1$ and R$^6$ for a compound corresponds in each case to one row of Table A Table 320
Compounds of the formula I.3A*, in which X is N—CH$_2$C≡CH, (R$^7$)$_m$ is 4-F and the combination of R$^1$ and R$^6$ for a compound corresponds in each case to one row of Table A Table 321
Compounds of the formula I.3A*, in which X is N—CH$_2$CN, (R$^7$)$_m$ is 4-F and the combination of R$^1$ and R$^6$ for a compound corresponds in each case to one row of Table A Table 322
Compounds of the formula I.3A*, in which X is N—CH$_2$CF$_3$, (RR$^{76}$)$_m$ is 4-F and the combination of R$^1$ and R$^6$ for a compound corresponds in each case to one row of Table A Table 323
Compounds of the formula I.3A*, in which X is N—CH$_2$C$_6$H$_5$, (R$^7$)$_m$ is 4-F and the combination of R$^1$ and R$^6$ for a compound corresponds in each case to one row of Table A Table 324
Compounds of the formula I.3A*, in which X is N—H, (R$^7$)$_m$ is 5-F and the combination of R$^1$ and R$^6$ for a compound corresponds in each case to one row of Table A Table 325
Compounds of the formula I.3A*, in which X is N—CH$_3$, (R$^7$)$_m$ is 5-F and the combination of R$^1$ and R$^6$ for a compound corresponds in each case to one row of Table A Table 326
Compounds of the formula I.3A*, in which X is N—C$_2$H$_5$, (R$^7$)$_m$ is 5-F and the combination of R$^1$ and R$^6$ for a compound corresponds in each case to one row of Table A Table 327
Compounds of the formula I.3A*, in which X is N-n-C$_3$H$_7$, (R$^7$)$_m$ is 5-F and the combination of R$^1$ and R$^6$ for a compound corresponds in each case to one row of Table A Table 328
Compounds of the formula I.3A*, in which X is N—CH(CH$_3$)$_2$, (R$^7$)$_m$ is 5-F and the combination of R$^1$ and R$^6$ for a compound corresponds in each case to one row of Table A Table 329
Compounds of the formula I.3A*, in which X is N-n-C$_4$H$_9$, (R$^7$)$_m$ is 5-F and the combination of R$^1$ and R$^6$ for a compound corresponds in each case to one row of Table A Table 330
Compounds of the formula I.3A*, in which X is N—CH$_2$CH═CH$_2$, (R$^7$)$_m$ is 5-F and the combination of R$^1$ and R$^6$ for a compound corresponds in each case to one row of Table A Table 331
Compounds of the formula I.3A*, in which X is N—CH$_2$C≡CH, (R$^7$)$_m$ is 5-F and the combination of R$^1$ and R$^6$ for a compound corresponds in each case to one row of Table A Table 332
Compounds of the formula I.3A*, in which X is N—CH$_2$CN, (R$^7$)$_m$ is 5-F and the combination of R$^1$ and R$^6$ for a compound corresponds in each case to one row of Table A Table 333
Compounds of the formula I.3A*, in which X is N—CH$_2$CF$_3$, (R$^7$)$_m$ is 5-F and the combination of R$^1$ and R$^6$ for a compound corresponds in each case to one row of Table A Table 334
Compounds of the formula I.3A*, in which X is N—CH$_2$C$_6$H$_5$, (R$^7$)$_m$ is 5-F and the combination of R$^1$ and R$^6$ for a compound corresponds in each case to one row of Table A Table 335
Compounds of the formula I.3A*, in which X is N—H, (R$^7$)$_m$ is 6-F and the combination of R$^1$ and R$^6$ for a compound corresponds in each case to one row of Table A Table 336
Compounds of the formula I.3A*, in which X is N—CH$_3$, (R$^7$)$_m$ is 6-F and the combination of R$^1$ and R$^6$ for a compound corresponds in each case to one row of Table A Table 337
Compounds of the formula I.3A*, in which X is N—C$_2$H$_5$, (R$^7$)$_m$ is 6-F and the combination of R$^1$ and R$^6$ for a compound corresponds in each case to one row of Table A Table 338
Compounds of the formula I.3A*, in which X is N-n-C$_3$H$_7$, (R$^7$)$_m$ is 6-F and the combination of R$^1$ and R$^6$ for a compound corresponds in each case to one row of Table A Table 339
Compounds of the formula I.3A*, in which X is N—CH(CH$_3$)$_2$, (R$^7$)$_m$ is 6-F and the combination of R$^1$ and R$^6$ for a compound corresponds in each case to one row of Table A Table 340
Compounds of the formula I.3A*, in which X is N-n-C$_4$H$_9$, (R$^7$)$_m$ is 6-F and the combination of R$^1$ and R$^6$ for a compound corresponds in each case to one row of Table A Table 341
Compounds of the formula I.3A*, in which X is N—CH$_2$CH═CH$_2$, (R$^7$)$_m$ is 6-F and the combination of R$^1$ and R$^6$ for a compound corresponds in each case to one row of Table A Table 342
Compounds of the formula I.3A*, in which X is N—CH$_2$C≡CH, (R$^7$)$_m$ is 6-F and the combination of R$^1$ and R$^6$ for a compound corresponds in each case to one row of Table A Table 343
Compounds of the formula I.3A*, in which X is N—CH$_2$CN, (R$^7$)$_m$ is 6-F and the combination of R$^1$ and R$^6$ for a compound corresponds in each case to one row of Table A Table 344
Compounds of the formula I.3A*, in which X is N—CH$_2$CF$_3$, (R$^7$)$_m$ is 6-F and the combination of R$^1$ and R$^6$ for a compound corresponds in each case to one row of Table A Table 345
Compounds of the formula I.3A*, in which X is N—CH$_2$C$_6$H$_5$, (R$^7$)$_m$ is 6-F and the combination of R$^1$ and R$^6$ for a compound corresponds in each case to one row of Table A Table 346
Compounds of the formula I.3A*, in which X is N—H, (R$^7$)$_m$ is 4-CF$_3$ and the combination of R$^1$ and R$^6$ for a compound corresponds in each case to one row of Table A Table 347
Compounds of the formula I.3A*, in which X is N—CH$_3$, (R$^7$)$_m$ is 4-CF$_3$ and the combination of R$^1$ and R$^6$ for a compound corresponds in each case to one row of Table A Table 348
Compounds of the formula I.3A*, in which X is N—C$_2$H$_5$, (R$^7$)$_m$ is 4-CF$_3$ and the combination of R$^1$ and R$^6$ for a compound corresponds in each case to one row of Table A Table 349
Compounds of the formula I.3A*, in which X is N-n-C$_3$H$_7$, (R$^7$)$_m$ is 4-CF$_3$ and the combination of R$^1$ and R$^6$ for a compound corresponds in each case to one row of Table A Table 350
Compounds of the formula I.3A*, in which X is N—CH(CH$_3$)$_2$, (R$^7$)$_m$ is 4-CF$_3$ and the combination of R$^1$ and R$^6$ for a compound corresponds in each case to one row of Table A Table 351
Compounds of the formula I.3A*, in which X is N-n-C$_4$H$_9$, (R$^7$)$_m$ is 4-CF$_3$ and the combination of R$^1$ and R$^6$ for a compound corresponds in each case to one row of Table A Table 352
Compounds of the formula I.3A*, in which X is N—CH$_2$CH=CH$_2$, (R$^7$)$_m$ is 4-CF$_3$ and the combination of R$^1$ and R$^6$ for a compound corresponds in each case to one row of Table A Table 353
Compounds of the formula I.3A*, in which X is N—CH$_2$C≡CH, (R$^7$)$_m$ is 4-CF$_3$ and the combination of R$^1$ and R$^6$ for a compound corresponds in each case to one row of Table A Table 354
Compounds of the formula I.3A*, in which X is N—CH$_2$CN, (R$^7$)$_m$ is 4-CF$_3$ and the combination of R$^1$ and R$^6$ for a compound corresponds in each case to one row of Table A Table 355
Compounds of the formula I.3A*, in which X is N—CH$_2$CF$_3$, (R$^7$)$_m$ is 4-CF$_3$ and the combination of R$^1$ and R$^6$ for a compound corresponds in each case to one row of Table A Table 356
Compounds of the formula I.3A*, in which X is N—CH$_2$C$_6$H$_5$, (R$^7$)$_m$ is 4-CF$_3$ and the combination of R$^1$ and R$^6$ for a compound corresponds in each case to one row of Table A Table 357
Compounds of the formula I.3A*, in which X is N—H, (R$^7$)$_m$ is 5-CF$_3$ and the combination of R$^1$ and R$^6$ for a compound corresponds in each case to one row of Table A Table 358
Compounds of the formula I.3A*, in which X is N—CH$_3$, (R$^7$)$_m$ is 5-CF$_3$ and the combination of R$^1$ and R$^6$ for a compound corresponds in each case to one row of Table A Table 359
Compounds of the formula I.3A*, in which X is N—C$_2$H$_5$, (R$^7$)$_m$ is 5-CF$_3$ and the combination of R$^1$ and R$^6$ for a compound corresponds in each case to one row of Table A Table 360
Compounds of the formula I.3A*, in which X is N-n-C$_3$H$_7$, (R$^7$)$_m$ is 5-CF$_3$ and the combination of R$^1$ and R$^6$ for a compound corresponds in each case to one row of Table A Table 361
Compounds of the formula I.3A*, in which X is N—CH(CH$_3$)$_2$, (R$^7$)$_m$ is 5-CF$_3$ and the combination of R$^1$ and R$^6$ for a compound corresponds in each case to one row of Table A Table 362
Compounds of the formula I.3A*, in which X is N-n-C$_4$H$_9$, (R$^7$)$_m$ is 5-CF$_3$ and the combination of R$^1$ and R$^6$ for a compound corresponds in each case to one row of Table A Table 363
Compounds of the formula I.3A*, in which X is N—CH$_2$CH=CH$_2$, (R$^7$)$_m$ is 5-CF$_3$ and the combination of R$^1$ and R$^6$ for a compound corresponds in each case to one row of Table A Table 364
Compounds of the formula I.3A*, in which X is N—CH$_2$C≡CH, (R$^7$)$_m$ is 5-CF$_3$ and the combination of R$^1$ and R$^6$ for a compound corresponds in each case to one row of Table A Table 365
Compounds of the formula I.3A*, in which X is N—CH$_2$CN, (R$^7$)$_m$ is 5-CF$_3$ and the combination of R$^1$ and R$^6$ for a compound corresponds in each case to one row of Table A Table 366
Compounds of the formula I.3A*, in which X is N—CH$_2$CF$_3$, (R$^7$)$_m$ is 5-CF$_3$ and the combination of R$^1$ and R$^6$ for a compound corresponds in each case to one row of Table A Table 367
Compounds of the formula I.3A*, in which X is N—CH$_2$C$_6$H$_5$, (R$^7$)$_m$ is 5-CF$_3$ and the combination of R$^1$ and R$^6$ for a compound corresponds in each case to one row of Table A Table 368
Compounds of the formula I.3A*, in which X is N—H, (R$^7$)$_m$ is 3,6-F$_2$ and the combination of R$^1$ and R$^6$ for a compound corresponds in each case to one row of Table A Table 369
Compounds of the formula I.3A*, in which X is N—CH$_3$, (R$^7$)$_m$ is 3,6-F$_2$ and the combination of R$^1$ and R$^6$ for a compound corresponds in each case to one row of Table A Table 370
Compounds of the formula I.3A*, in which X is N—C$_2$H$_5$, (R$^7$)$_m$ is 3,6-F$_2$ and the combination of R$^1$ and R$^6$ for a compound corresponds in each case to one row of Table A Table 371
Compounds of the formula I.3A*, in which X is N-n-C$_3$H$_7$, (R$^7$)$_m$ is 3,6-F$_2$ and the combination of R$^1$ and R$^6$ for a compound corresponds in each case to one row of Table A Table 372
Compounds of the formula I.3A*, in which X is N—CH(CH$_3$)$_2$, (R$^7$)$_m$ is 3,6-F$_2$ and the combination of R$^1$ and R$^6$ for a compound corresponds in each case to one row of Table A Table 373
Compounds of the formula I.3A*, in which X is N-n-$C_4H_9$, $(R^7)_m$ is 3,6-$F_2$ and the combination of $R^1$ and $R^6$ for a compound corresponds in each case to one row of Table A Table 374
Compounds of the formula I.3A*, in which X is N—$CH_2CH$=$CH_2$, $(R^7)_m$ is 3,6-$F_2$ and the combination of $R^1$ and $R^6$ for a compound corresponds in each case to one row of Table A Table 375
Compounds of the formula I.3A*, in which X is N—$CH_2C$≡CH, $(R^7)_m$ is 3,6-$F_2$ and the combination of $R^1$ and $R^6$ for a compound corresponds in each case to one row of Table A Table 376
Compounds of the formula I.3A*, in which X is N—$CH_2CN$, $(R^7)_m$ is 3,6-$F_2$ and the combination of $R^1$ and $R^6$ for a compound corresponds in each case to one row of Table A Table 377
Compounds of the formula I.3A*, in which X is N—$CH_2CF_3$, $(R^7)_m$ is 3,6-$F_2$ and the combination of $R^1$ and $R^6$ for a compound corresponds in each case to one row of Table A Table 378
Compounds of the formula I.3A*, in which X is N—$CH_2C_6H_5$, $(R^7)_m$ is 3,6-$F_2$ and the combination of $R^1$ and $R^6$ for a compound corresponds in each case to one row of Table A Table 379
Compounds of the formula I.4A*, in which X is oxygen, the index m in $(R^7)_m$ is zero and the combination of $R^1$ and $R^6$ for a compound corresponds in each case to one row of Table A Table 380
Compounds of the formula I.4A*, in which X is oxygen, $(R^7)_m$ is 4-Cl and the combination of $R^1$ and $R^6$ for a compound corresponds in each case to one row of Table A Table 381
Compounds of the formula I.4A*, in which X is oxygen, $(R^7)_m$ is 3-F and the combination of $R^1$ and $R^6$ for a compound corresponds in each case to one row of Table A Table 382
Compounds of the formula I.4A*, in which X is oxygen, $(R^7)_m$ is 4-F and the combination of $R^1$ and $R^6$ for a compound corresponds in each case to one row of Table A Table 383
Compounds of the formula I.4A*, in which X is oxygen, $(R^7)_m$ is 5-F and the combination of $R^1$ and $R^6$ for a compound corresponds in each case to one row of Table A Table 384
Compounds of the formula I.4A*, in which X is oxygen, $(R^7)_m$ is 6-F and the combination of $R^1$ and $R^6$ for a compound corresponds in each case to one row of Table A Table 385
Compounds of the formula I.4A*, in which X is oxygen, $(R^7)_m$ is 4-$CF_3$ and the combination of $R^1$ and $R^6$ for a compound corresponds in each case to one row of Table A Table 386
Compounds of the formula I.4A*, in which X is oxygen, $(R^7)_m$ is 5-$CF_3$ and the combination of $R^1$ and $R^6$ for a compound corresponds in each case to one row of Table A Table 387
Compounds of the formula I.4A*, in which X is oxygen, $(R^7)_m$ is 3,6-$F_2$ and the combination of $R^1$ and $R^6$ for a compound corresponds in each case to one row of Table A Table 388
Compounds of the formula I.4A*, in which X is sulfur, the index m in $(R^7)_m$ is zero and the combination of $R^1$ and $R^6$ for a compound corresponds in each case to one row of Table A Table 389
Compounds of the formula I.4A*, in which X is sulfur, $(R^7)_m$ is 4-Cl and the combination of $R^1$ and $R^6$ for a compound corresponds in each case to one row of Table A Table 390
Compounds of the formula I.4A*, in which X is sulfur, $(R^7)_m$ is 3-F and the combination of $R^1$ and $R^6$ for a compound corresponds in each case to one row of Table A Table 391
Compounds of the formula I.4A*, in which X is sulfur, $(R^7)_m$ is 4-F and the combination of $R^1$ and $R^6$ for a compound corresponds in each case to one row of Table A Table 392
Compounds of the formula I.4A*, in which X is sulfur, $(R^7)_m$ is 5-F and the combination of $R^1$ and $R^6$ for a compound corresponds in each case to one row of Table A Table 393
Compounds of the formula I.4A*, in which X is sulfur, $(R^7)_m$ is 6-F and the combination of $R^1$ and $R^6$ for a compound corresponds in each case to one row of Table A Table 394
Compounds of the formula I.4A*, in which X is sulfur, $(R^7)_m$ is 4-$CF_3$ and the combination of $R^1$ and $R^6$ for a compound corresponds in each case to one row of Table A Table 395
Compounds of the formula I.4A*, in which X is sulfur, $(R^7)_m$ is 5-$CF_3$ and the combination of $R^1$ and $R^6$ for a compound corresponds in each case to one row of Table A Table 396
Compounds of the formula I.4A*, in which X is sulfur, $(R^7)_m$ is 3,6-$F_2$ and the combination of $R^1$ and $R^6$ for a compound corresponds in each case to one row of Table A Table 397
Compounds of the formula I.4A*, in which X is sulfur, the index m in $(R^7)_m$ is zero and the combination of $R^1$ and $R^6$ for a compound corresponds in each case to one row of Table A Table 398
Compounds of the formula I.4A*, in which X is sulfur, $(R^7)_m$ is 4-Cl and the combination of W and $R^6$ for a compound corresponds in each case to one row of Table A Table 399
Compounds of the formula I.4A*, in which X is sulfur, $(R^7)_m$ is 3-F and the combination of W and $R^6$ for a compound corresponds in each case to one row of Table A Table 400
Compounds of the formula I.4A*, in which X is sulfur, $(R^7)_m$ is 4-F and the combination of W and $R^6$ for a compound corresponds in each case to one row of Table A Table 401
Compounds of the formula I.4A*, in which X is sulfur, $(R^7)_m$ is 5-F and the combination of $R^1$ and $R^6$ for a compound corresponds in each case to one row of Table A Table 402
Compounds of the formula I.4A*, in which X is sulfur, $(R^7)_m$ is 6-F and the combination of $R^1$ and $R^6$ for a compound corresponds in each case to one row of Table A Table 403
Compounds of the formula I.4A*, in which X is sulfur, $(R^7)_m$ is 4-$CF_3$ and the combination of $R^1$ and $R^6$ for a compound corresponds in each case to one row of Table A Table 404
Compounds of the formula I.4A*, in which X is sulfur, $(R^7)_m$ is 5-$CF_3$ and the combination of $R^1$ and $R^6$ for a compound corresponds in each case to one row of Table A Table 405
Compounds of the formula I.4A*, in which X is sulfur, $(R^7)_m$ is 3,6-$F_2$ and the combination of $R^1$ and $R^6$ for a compound corresponds in each case to one row of Table A Table 406
Compounds of the formula I.4A*, in which X is N—H, the index m in $(R^7)_m$ is zero and the combination of $R^1$ and $R^6$ for a compound corresponds in each case to one row of Table A Table 407
Compounds of the formula I.4A*, in which X is N—$CH_3$, the index m in $(R^7)_m$ is zero and the combination of $R^1$ and $R^6$ for a compound corresponds in each case to one row of Table A Table 408
Compounds of the formula I.4A*, in which X is N—$C_2H_5$, the index m in $(R^7)_m$ is zero and the combination of $R^1$ and $R^6$ for a compound corresponds in each case to one row of Table A Table 409
Compounds of the formula I.4A*, in which X is N-n-$C_3H_7$, the index m in $(R^7)_m$ is zero and the combination of $R^1$ and $R^6$ for a compound corresponds in each case to one row of Table A Table 410
Compounds of the formula I.4A*, in which X is N—CH$(CH_3)_2$, the index m in $(R^7)_m$ is zero and the combination of $R^1$ and $R^6$ for a compound corresponds in each case to one row of Table A Table 411
Compounds of the formula I.4A*, in which X is N-n-$C_4H_9$, the index m in $(R^7)_m$ is zero and the combination of $R^1$ and $R^6$ for a compound corresponds in each case to one row of Table A Table 412
Compounds of the formula I.4A*, in which X is N—$CH_2CH$=$CH_2$, the index m in $(R^7)_m$ is zero and the combination of $R^1$ and $R^6$ for a compound corresponds in each case to one row of Table A Table 413
Compounds of the formula I.4A*, in which X is N—$CH_2C$≡CH, the index m in $(R^7)_m$ is zero and the combination of $R^1$ and $R^6$ for a compound corresponds in each case to one row of Table A Table 414
Compounds of the formula I.4A*, in which X is N—$CH_2CN$, the index m in $(R^7)_m$ is zero and the combination of $R^1$ and $R^6$ for a compound corresponds in each case to one row of Table A Table 415
Compounds of the formula I.4A*, in which X is N—$CH_2CF_3$, the index m in $(R^7)_m$ is zero and the combination of $R^1$ and $R^6$ for a compound corresponds in each case to one row of Table A Table 416
Compounds of the formula I.4A*, in which X is N—$CH_2C_6H_5$, the index m in $(R^7)_m$ is zero and the combination of $R^1$ and $R^6$ for a compound corresponds in each case to one row of Table A Table 417
Compounds of the formula I.4A*, in which X is N—H, $(R^7)_m$ is 4-Cl and the combination of $R^1$ and $R^6$ for a compound corresponds in each case to one row of Table A Table 418
Compounds of the formula I.4A*, in which X is N—$CH_3$, $(R^7)_m$ is 4-Cl and the combination of $R^1$ and $R^6$ for a compound corresponds in each case to one row of Table A Table 419
Compounds of the formula I.4A*, in which X is N—$C_2H_5$, $(R^7)_m$ is 4-Cl and the combination of $R^1$ and $R^6$ for a compound corresponds in each case to one row of Table A Table 420
Compounds of the formula I.4A*, in which X is N-n-$C_3H_7$, $(R^7)_m$ is 4-Cl and the combination of $R^1$ and $R^6$ for a compound corresponds in each case to one row of Table A Table 421
Compounds of the formula I.4A*, in which X is N—CH$(CH_3)_2$, $(R^7)_m$ is 4-Cl and the combination of $R^1$ and $R^6$ for a compound corresponds in each case to one row of Table A Table 422
Compounds of the formula I.4A*, in which X is N-n-$C_4H_9$, $(R^7)_m$ is 4-Cl and the combination of $R^1$ and $R^6$ for a compound corresponds in each case to one row of Table A Table 423
Compounds of the formula I.4A*, in which X is N—$CH_2CH$=$CH_2$, $(R^7)_m$ is 4-Cl and the combination of $R^1$ and $R^6$ for a compound corresponds in each case to one row of Table A Table 424
Compounds of the formula I.4A*, in which X is N—$CH_2C$≡CH, $(R^7)_m$ is 4-Cl and the combination of $R^1$ and $R^6$ for a compound corresponds in each case to one row of Table A Table 425
Compounds of the formula I.4A*, in which X is N—$CH_2CN$, $(R^7)_m$ is 4-Cl and the combination of $R^1$ and $R^6$ for a compound corresponds in each case to one row of Table A Table 426
Compounds of the formula I.4A*, in which X is N—$CH_2CF_3$, $(R^7)_m$ is 4-Cl and the combination of $R^1$ and $R^6$ for a compound corresponds in each case to one row of Table A Table 427
Compounds of the formula I.4A*, in which X is N—$CH_2C_6H_5$, $(R^7)_m$ is 4-Cl and the combination of $R^1$ and $R^6$ for a compound corresponds in each case to one row of Table A Table 428
Compounds of the formula I.4A*, in which X is N—H, $(R^7)_m$ is 3-F and the combination of $R^1$ and $R^6$ for a compound corresponds in each case to one row of Table A Table 429
Compounds of the formula I.4A*, in which X is N—$CH_3$, $(R^7)_m$ is 3-F and the combination of $R^1$ and $R^6$ for a compound corresponds in each case to one row of Table A Table 430
Compounds of the formula I.4A*, in which X is N—$C_2H_5$, $(R^7)_m$ is 3-F and the combination of $R^1$ and $R^6$ for a compound corresponds in each case to one row of Table A Table 431
Compounds of the formula I.4A*, in which X is N-n-$C_3H_7$, $(R^7)_m$ is 3-F and the combination of $R^1$ and $R^6$ for a compound corresponds in each case to one row of Table A Table 432
Compounds of the formula I.4A*, in which X is N—CH$(CH_3)_2$, $(R^7)_m$ is 3-F and the combination of $R^1$ and $R^6$ for a compound corresponds in each case to one row of Table A Table 433
Compounds of the formula I.4A*, in which X is N-n-$C_4H_9$, $(R^7)_m$ is 3-F and the combination of $R^1$ and $R^6$ for a compound corresponds in each case to one row of Table A Table 434
Compounds of the formula I.4A*, in which X is N—$CH_2CH$=$CH_2$, $(R^7)_m$ is 3-F and the combination of $R^1$ and $R^6$ for a compound corresponds in each case to one row of Table A Table 435
Compounds of the formula I.4A*, in which X is N—CH$_2$C≡CH, (R$^7$)$_m$ is 3-F and the combination of R$^1$ and R$^6$ for a compound corresponds in each case to one row of Table A Table 436
Compounds of the formula I.4A*, in which X is N—CH$_2$CN, (R$^7$)$_m$ is 3-F and the combination of R$^1$ and R$^6$ for a compound corresponds in each case to one row of Table A Table 437
Compounds of the formula I.4A*, in which X is N—CH$_2$CF$_3$, (R$^7$)$_m$ is 3-F and the combination of R$^1$ and R$^6$ for a compound corresponds in each case to one row of Table A Table 438
Compounds of the formula I.4A*, in which X is N—CH$_2$C$_6$H$_5$, (R$^7$)$_m$ is 3-F and the combination of R$^1$ and R$^6$ for a compound corresponds in each case to one row of Table A Table 439
Compounds of the formula I.4A*, in which X is N—H, (R$^7$)$_m$ is 4-F and the combination of R$^1$ and R$^6$ for a compound corresponds in each case to one row of Table A Table 440
Compounds of the formula I.4A*, in which X is N—CH$_3$, (R$^7$)$_m$ is 4-F and the combination of R$^1$ and R$^6$ for a compound corresponds in each case to one row of Table A Table 441
Compounds of the formula I.4A*, in which X is N—C$_2$H$_5$, (R$^7$)$_m$ is 4-F and the combination of R$^1$ and R$^6$ for a compound corresponds in each case to one row of Table A Table 442
Compounds of the formula I.4A*, in which X is N-n-C$_3$H$_7$, (R$^7$)$_m$ is 4-F and the combination of R$^1$ and R$^6$ for a compound corresponds in each case to one row of Table A Table 443
Compounds of the formula I.4A*, in which X is N—CH(CH$_3$)$_2$, (R$^7$)$_m$ is 4-F and the combination of R$^1$ and R$^6$ for a compound corresponds in each case to one row of Table A Table 444
Compounds of the formula I.4A*, in which X is N-n-C$_4$H$_9$, (R$^7$)$_m$ is 4-F and the combination of R$^1$ and R$^6$ for a compound corresponds in each case to one row of Table A Table 445
Compounds of the formula I.4A*, in which X is N—CH$_2$CH═CH$_2$, (R$^7$)$_m$ is 4-F and the combination of R$^1$ and R$^6$ for a compound corresponds in each case to one row of Table A Table 446
Compounds of the formula I.4A*, in which X is N—CH$_2$C≡CH, (R$^7$)$_m$ is 4-F and the combination of R$^1$ and R$^6$ for a compound corresponds in each case to one row of Table A Table 447
Compounds of the formula I.4A*, in which X is N—CH$_2$CN, (R$^7$)$_m$ is 4-F and the combination of R$^1$ and R$^6$ for a compound corresponds in each case to one row of Table A Table 448
Compounds of the formula I.4A*, in which X is N—CH$_2$CF$_3$, (R$^7$)$_m$ is 4-F and the combination of R$^1$ and R$^6$ for a compound corresponds in each case to one row of Table A Table 449
Compounds of the formula I.4A*, in which X is N—CH$_2$C$_6$H$_5$, (R$^7$)$_m$ is 4-F and the combination of R$^1$ and R$^6$ for a compound corresponds in each case to one row of Table A Table 450
Compounds of the formula I.4A*, in which X is N—H, (R$^7$)$_m$ is 5-F and the combination of R$^1$ and R$^6$ for a compound corresponds in each case to one row of Table A Table 451
Compounds of the formula I.4A*, in which X is N—CH$_3$, (R$^7$)$_m$ is 5-F and the combination of R$^1$ and R$^6$ for a compound corresponds in each case to one row of Table A Table 452
Compounds of the formula I.4A*, in which X is N—C$_2$H$_5$, (R$^7$)$_m$ is 5-F and the combination of R$^1$ and R$^6$ for a compound corresponds in each case to one row of Table A Table 453
Compounds of the formula I.4A*, in which X is N-n-C$_3$H$_7$, (R$^7$)$_m$ is 5-F and the combination of R$^1$ and R$^6$ for a compound corresponds in each case to one row of Table A Table 454
Compounds of the formula I.4A*, in which X is N—CH(CH$_3$)$_2$, (R$^7$)$_m$ is 5-F and the combination of R$^1$ and R$^6$ for a compound corresponds in each case to one row of Table A Table 455
Compounds of the formula I.4A*, in which X is N-n-C$_4$H$_9$, (R$^7$)$_m$ is 5-F and the combination of R$^1$ and R$^6$ for a compound corresponds in each case to one row of Table A Table 456
Compounds of the formula I.4A*, in which X is N—CH$_2$CH═CH$_2$, (R$^7$)$_m$ is 5-F and the combination of R$^1$ and R$^6$ for a compound corresponds in each case to one row of Table A Table 457
Compounds of the formula I.4A*, in which X is N—CH$_2$C≡CH, (R$^7$)$_m$ is 5-F and the combination of R$^1$ and R$^6$ for a compound corresponds in each case to one row of Table A Table 458
Compounds of the formula I.4A*, in which X is N—CH$_2$CN, (R$^7$)$_m$ is 5-F and the combination of R$^1$ and R$^6$ for a compound corresponds in each case to one row of Table A Table 459
Compounds of the formula I.4A*, in which X is N—CH$_2$CF$_3$, (R$^7$)$_m$ is 5-F and the combination of R$^1$ and R$^6$ for a compound corresponds in each case to one row of Table A Table 460
Compounds of the formula I.4A*, in which X is N—CH$_2$C$_6$H$_5$, (R$^7$)$_m$ is 5-F and the combination of R$^1$ and R$^6$ for a compound corresponds in each case to one row of Table A Table 461
Compounds of the formula I.4A*, in which X is N—H, (R$^7$)$_m$ is 6-F and the combination of R$^1$ and R$^6$ for a compound corresponds in each case to one row of Table A Table 462
Compounds of the formula I.4A*, in which X is N—CH$_3$, (R$^7$)$_m$ is 6-F and the combination of R$^1$ and R$^6$ for a compound corresponds in each case to one row of Table A Table 463
Compounds of the formula I.4A*, in which X is N—C$_2$H$_5$, (R$^7$)$_m$ is 6-F and the combination of R$^1$ and R$^6$ for a compound corresponds in each case to one row of Table A Table 464
Compounds of the formula I.4A*, in which X is N-n-C$_3$H$_7$, (R$^7$)$_m$ is 6-F and the combination of R$^1$ and R$^6$ for a compound corresponds in each case to one row of Table A Table 465
Compounds of the formula I.4A*, in which X is N—CH(CH$_3$)$_2$, (R$^7$)$_m$ is 6-F and the combination of R$^1$ and R$^6$ for a compound corresponds in each case to one row of Table A Table 466
Compounds of the formula I.4A*, in which X is N-n-$C_4H_9$, $(R^7)_m$ is 6-F and the combination of $R^1$ and $R^6$ for a compound corresponds in each case to one row of Table A Table 467
Compounds of the formula I.4A*, in which X is N—$CH_2CH=CH_2$, $(R^7)_m$ is 6-F and the combination of $R^1$ and $R^6$ for a compound corresponds in each case to one row of Table A Table 468
Compounds of the formula I.4A*, in which X is N—$CH_2C\equiv CH$, $(R^7)_m$ is 6-F and the combination of $R^1$ and $R^6$ for a compound corresponds in each case to one row of Table A Table 469
Compounds of the formula I.4A*, in which X is N—$CH_2CN$, $(R^7)_m$ is 6-F and the combination of $R^1$ and $R^6$ for a compound corresponds in each case to one row of Table A Table 470
Compounds of the formula I.4A*, in which X is N—$CH_2CF_3$, $(R^7)_m$ is 6-F and the combination of $R^1$ and $R^6$ for a compound corresponds in each case to one row of Table A Table 471
Compounds of the formula I.4A*, in which X is N—$CH_2C_6H_5$, $(R^7)_m$ is 6-F and the combination of $R^1$ and $R^6$ for a compound corresponds in each case to one row of Table A Table 472
Compounds of the formula I.4A*, in which X is N—H, $(R^7)_m$ is 4-$CF_3$ and the combination of $R^1$ and $R^6$ for a compound corresponds in each case to one row of Table A Table 473
Compounds of the formula I.4A*, in which X is N—$CH_3$, $(R^7)_m$ is 4-$CF_3$ and the combination of $R^1$ and $R^6$ for a compound corresponds in each case to one row of Table A Table 474
Compounds of the formula I.4A*, in which X is N—$C_2H_5$, $(R^7)_m$ is 4-$CF_3$ and the combination of $R^1$ and $R^6$ for a compound corresponds in each case to one row of Table A Table 475
Compounds of the formula I.4A*, in which X is N-n-$C_3H_7$, $(R^7)_m$ is 4-$CF_3$ and the combination of $R^1$ and $R^6$ for a compound corresponds in each case to one row of Table A Table 476
Compounds of the formula I.4A*, in which X is N—CH$(CH_3)_2$, $(R^7)_m$ is 4-$CF_3$ and the combination of $R^1$ and $R^6$ for a compound corresponds in each case to one row of Table A Table 477
Compounds of the formula I.4A*, in which X is N-n-$C_4H_9$, $(R^7)_m$ is 4-$CF_3$ and the combination of $R^1$ and $R^6$ for a compound corresponds in each case to one row of Table A Table 478
Compounds of the formula I.4A*, in which X is N—$CH_2CH=CH_2$, $(R^7)_m$ is 4-$CF_3$ and the combination of $R^1$ and $R^6$ for a compound corresponds in each case to one row of Table A Table 479
Compounds of the formula I.4A*, in which X is N—$CH_2C\equiv CH$, $(R^7)_m$ is 4-$CF_3$ and the combination of $R^1$ and $R^6$ for a compound corresponds in each case to one row of Table A Table 480
Compounds of the formula I.4A*, in which X is N—$CH_2CN$, $(R^7)_m$ is 4-$CF_3$ and the combination of $R^1$ and $R^6$ for a compound corresponds in each case to one row of Table A Table 481
Compounds of the formula I.4A*, in which X is N—$CH_2CF_3$, $(R^7)_m$ is 4-$CF_3$ and the combination of $R^1$ and $R^6$ for a compound corresponds in each case to one row of Table A Table 482
Compounds of the formula I.4A*, in which X is N—$CH_2C_6H_5$, $(R^7)_m$ is 4-$CF_3$ and the combination of $R^1$ and $R^6$ for a compound corresponds in each case to one row of Table A Table 483
Compounds of the formula I.4A*, in which X is N—H, $(R^7)_m$ is 5-$CF_3$ and the combination of $R^1$ and $R^6$ for a compound corresponds in each case to one row of Table A Table 484
Compounds of the formula I.4A*, in which X is N—$CH_3$, $(R^7)_m$ is 5-$CF_3$ and the combination of $R^1$ and $R^6$ for a compound corresponds in each case to one row of Table A Table 485
Compounds of the formula I.4A*, in which X is N—$C_2H_5$, $(R^7)_m$ is 5-$CF_3$ and the combination of $R^1$ and $R^6$ for a compound corresponds in each case to one row of Table A Table 486
Compounds of the formula I.4A*, in which X is N-n-$C_3H_7$, $(R^7)_m$ is 5-$CF_3$ and the combination of $R^1$ and $R^6$ for a compound corresponds in each case to one row of Table A Table 487
Compounds of the formula I.4A*, in which X is N—CH$(CH_3)_2$, $(R^7)_m$ is 5-$CF_3$ and the combination of $R^1$ and $R^6$ for a compound corresponds in each case to one row of Table A Table 488
Compounds of the formula I.4A*, in which X is N-n-$C_4H_9$, $(R^7)_m$ is 5-$CF_3$ and the combination of $R^1$ and $R^6$ for a compound corresponds in each case to one row of Table A Table 489
Compounds of the formula I.4A*, in which X is N—$CH_2CH=CH_2$, $(R^7)_m$ is 5-$CF_3$ and the combination of $R^1$ and $R^6$ for a compound corresponds in each case to one row of Table A Table 490
Compounds of the formula I.4A*, in which X is N—$CH_2C\equiv CH$, $(R^7)_m$ is 5-$CF_3$ and the combination of $R^1$ and $R^6$ for a compound corresponds in each case to one row of Table A Table 491
Compounds of the formula I.4A*, in which X is N—$CH_2CN$, $(R^7)_m$ is 5-$CF_3$ and the combination of $R^1$ and $R^6$ for a compound corresponds in each case to one row of Table A Table 492
Compounds of the formula I.4A*, in which X is N—$CH_2CF_3$, $(R^7)_m$ is 5-$CF_3$ and the combination of $R^1$ and $R^6$ for a compound corresponds in each case to one row of Table A Table 493
Compounds of the formula I.4A*, in which X is N—$CH_2C_6H_5$, $(R^7)_m$ is 5-$CF_3$ and the combination of $R^1$ and $R^6$ for a compound corresponds in each case to one row of Table A Table 494
Compounds of the formula I.4A*, in which X is N—H, $(R^7)_m$ is 3,6-$F_2$ and the combination of $R^1$ and $R^6$ for a compound corresponds in each case to one row of Table A Table 495
Compounds of the formula I.4A*, in which X is N—$CH_3$, $(R^7)_m$ is 3,6-$F_2$ and the combination of $R^1$ and $R^6$ for a compound corresponds in each case to one row of Table A Table 496
Compounds of the formula I.4A*, in which X is N—$C_2H_5$, $(R^7)_m$ is 3,6-$F_2$ and the combination of $R^1$ and $R^6$ for a compound corresponds in each case to one row of Table A Table 497
Compounds of the formula I.4A*, in which X is N-n-$C_3H_7$, $(R^7)_m$ is 3,6-$F_2$ and the combination of $R^1$ and $R^6$ for a compound corresponds in each case to one row of Table A Table 498
Compounds of the formula I.4A*, in which X is N—CH$(CH_3)_2$, $(R^7)_m$ is 3,6-$F_2$ and the combination of $R^1$ and $R^6$ for a compound corresponds in each case to one row of Table A Table 499
Compounds of the formula I.4A*, in which X is N-n-$C_4H_9$, $(R^7)_m$ is 3,6-$F_2$ and the combination of $R^1$ and $R^6$ for a compound corresponds in each case to one row of Table A Table 500
Compounds of the formula I.4A*, in which X is N—$CH_2CH$=$CH_2$, $(R^7)_m$ is 3,6-$F_2$ and the combination of $R^1$ and $R^6$ for a compound corresponds in each case to one row of Table A Table 501
Compounds of the formula I.4A*, in which X is N—$CH_2C$≡CH, $(R^7)_m$ is 3,6-$F_2$ and the combination of $R^1$ and $R^6$ for a compound corresponds in each case to one row of Table A Table 502
Compounds of the formula I.4A*, in which X is N—$CH_2CN$, $(R^7)_m$ is 3,6-$F_2$ and the combination of $R^1$ and $R^6$ for a compound corresponds in each case to one row of Table A Table 503
Compounds of the formula I.4A*, in which X is N—$CH_2CF_3$, $(R^7)_m$ is 3,6-$F_2$ and the combination of $R^1$ and $R^6$ for a compound corresponds in each case to one row of Table A Table 504
Compounds of the formula I.4A*, in which X is N—$CH_2C_6H_5$, $(R^7)_m$ is 3,6-$F_2$ and the combination of $R^1$ and $R^6$ for a compound corresponds in each case to one row of Table A Table 505
Compounds of the formula I.5A*, in which X is oxygen, the index m in $(R^7)_m$ is zero and the combination of $R^1$ and $R^6$ for a compound corresponds in each case to one row of Table A Table 506
Compounds of the formula I.5A*, in which X is oxygen, $(R^7)_m$ is 4-Cl and the combination of $R^1$ and $R^6$ for a compound corresponds in each case to one row of Table A Table 507
Compounds of the formula I.5A*, in which X is oxygen, $(R^7)_m$ is 3-F and the combination of $R^1$ and $R^6$ for a compound corresponds in each case to one row of Table A Table 508
Compounds of the formula I.5A*, in which X is oxygen, $(R^7)_m$ is 4-F and the combination of $R^1$ and $R^6$ for a compound corresponds in each case to one row of Table A Table 509
Compounds of the formula I.5A*, in which X is oxygen, $(R^7)_m$ is 5-F and the combination of $R^1$ and $R^6$ for a compound corresponds in each case to one row of Table A Table 510
Compounds of the formula I.5A*, in which X is oxygen, $(R^7)_m$ is 6-F and the combination of $R^1$ and $R^6$ for a compound corresponds in each case to one row of Table A Table 511
Compounds of the formula I.5A*, in which X is oxygen, $(R^7)_m$ is 4-$CF_3$ and the combination of $R^1$ and $R^6$ for a compound corresponds in each case to one row of Table A Table 512
Compounds of the formula I.5A*, in which X is oxygen, $(R^7)_m$ is 5-$CF_3$ and the combination of $R^1$ and $R^6$ for a compound corresponds in each case to one row of Table A Table 513
Compounds of the formula I.5A*, in which X is oxygen, $(R^7)_m$ is 3,6-$F_2$ and the combination of $R^1$ and $R^6$ for a compound corresponds in each case to one row of Table A Table 514
Compounds of the formula I.5A*, in which X is sulfur, the index m in $(R^7)_m$ is zero and the combination of $R^1$ and $R^6$ for a compound corresponds in each case to one row of Table A Table 515
Compounds of the formula I.5A*, in which X is sulfur, $(R^7)_m$ is 4-Cl and the combination of $R^1$ and $R^6$ for a compound corresponds in each case to one row of Table A Table 516
Compounds of the formula I.5A*, in which X is sulfur, $(R^7)_m$ is 3-F and the combination of $R^1$ and $R^6$ for a compound corresponds in each case to one row of Table A Table 517
Compounds of the formula I.5A*, in which X is sulfur, $(R^7)_m$ is 4-F and the combination of $R^1$ and $R^6$ for a compound corresponds in each case to one row of Table A Table 518
Compounds of the formula I.5A*, in which X is sulfur, $(R^7)_m$ is 5-F and the combination of $R^1$ and $R^6$ for a compound corresponds in each case to one row of Table A Table 519
Compounds of the formula I.5A*, in which X is sulfur, $(R^7)_m$ is 6-F and the combination of $R^1$ and $R^6$ for a compound corresponds in each case to one row of Table A Table 520
Compounds of the formula I.5A*, in which X is sulfur, $(R^7)_m$ is 4-$CF_3$ and the combination of $R^1$ and $R^6$ for a compound corresponds in each case to one row of Table A Table 521
Compounds of the formula I.5A*, in which X is sulfur, $(R^7)_m$ is 5-$CF_3$ and the combination of $R^1$ and $R^6$ for a compound corresponds in each case to one row of Table A Table 522
Compounds of the formula I.5A*, in which X is sulfur, $(R^7)_m$ is 3,6-$F_2$ and the combination of $R^1$ and $R^6$ for a compound corresponds in each case to one row of Table A Table 523
Compounds of the formula I.5A*, in which X is sulfur, the index m in $(R^7)_m$ is zero and the combination of $R^1$ and $R^6$ for a compound corresponds in each case to one row of Table A Table 524
Compounds of the formula I.5A*, in which X is sulfur, $(R^7)_m$ is 4-Cl and the combination of $R^1$ and $R^6$ for a compound corresponds in each case to one row of Table A Table 525
Compounds of the formula I.5A*, in which X is sulfur, $(R^7)_m$ is 3-F and the combination of $R^1$ and $R^6$ for a compound corresponds in each case to one row of Table A Table 526
Compounds of the formula I.5A*, in which X is sulfur, $(R^7)_m$ is 4-F and the combination of $R^1$ and $R^6$ for a compound corresponds in each case to one row of Table A Table 527
Compounds of the formula I.5A*, in which X is sulfur, $(R^7)_m$ is 5-F and the combination of $R^1$ and $R^6$ for a compound corresponds in each case to one row of Table A Table 528
Compounds of the formula I.5A*, in which X is sulfur, $(R^7)_m$ is 6-F and the combination of $R^1$ and $R^6$ for a compound corresponds in each case to one row of Table A Table 529
Compounds of the formula I.5A*, in which X is sulfur, $(RR^{76})_m$ is 4-$CF_3$ and the combination of $R^1$ and $R^6$ for a compound corresponds in each case to one row of Table A Table 530
Compounds of the formula I.5A*, in which X is sulfur, $(R^7)_m$ is 5-$CF_3$ and the combination of $R^1$ and $R^6$ for a compound corresponds in each case to one row of Table A Table 531
Compounds of the formula I.5A*, in which X is sulfur, $(R^7)_m$ is 3,6-$F_2$ and the combination of $R^1$ and $R^6$ for a compound corresponds in each case to one row of Table A Table 532
Compounds of the formula I.5A*, in which X is N—H, the index m in $(R^7)_m$ is zero and the combination of $R^1$ and $R^6$ for a compound corresponds in each case to one row of Table A Table 533
Compounds of the formula I.5A*, in which X is N—$CH_3$, the index m in $(R^7)_m$ is zero and the combination of $R^1$ and $R^6$ for a compound corresponds in each case to one row of Table A Table 534
Compounds of the formula I.5A*, in which X is N—$C_2H_5$, the index m in $(R^7)_m$ is zero and the combination of $R^1$ and $R^6$ for a compound corresponds in each case to one row of Table A Table 535
Compounds of the formula I.5A*, in which X is N-n-$C_3H_7$, the index m in $(R^7)_m$ is zero and the combination of $R^1$ and $R^6$ for a compound corresponds in each case to one row of Table A Table 536
Compounds of the formula I.5A*, in which X is N—CH$(CH_3)_2$, the index m in $(R^7)_m$ is zero and the combination of $R^1$ and $R^6$ for a compound corresponds in each case to one row of Table A Table 537
Compounds of the formula I.5A*, in which X is N-n-$C_4H_9$, the index m in $(R^7)_m$ is zero and the combination of $R^1$ and $R^6$ for a compound corresponds in each case to one row of Table A Table 538
Compounds of the formula I.5A*, in which X is N—$CH_2CH$=$CH_2$, the index m in $(R^7)_m$ is zero and the combination of $R^1$ and $R^6$ for a compound corresponds in each case to one row of Table A Table 539
Compounds of the formula I.5A*, in which X is N—$CH_2C$≡CH, the index m in $(R^7)_m$ is zero and the combination of $R^1$ and $R^6$ for a compound corresponds in each case to one row of Table A Table 540
Compounds of the formula I.5A*, in which X is N—$CH_2CN$, the index m in $(R^7)_m$ is zero and the combination of $R^1$ and $R^6$ for a compound corresponds in each case to one row of Table A Table 541
Compounds of the formula I.5A*, in which X is N—$CH_2CF_3$, the index m in $(R^7)_m$ is zero and the combination of $R^1$ and $R^6$ for a compound corresponds in each case to one row of Table A Table 542
Compounds of the formula I.5A*, in which X is N—$CH_2C_6H_5$, the index m in $(R^7)_m$ is zero and the combination of $R^1$ and $R^6$ for a compound corresponds in each case to one row of Table A Table 543
Compounds of the formula I.5A*, in which X is N—H, $(R^7)_m$ is 4-Cl and the combination of $R^1$ and $R^6$ for a compound corresponds in each case to one row of Table A Table 544
Compounds of the formula I.5A*, in which X is N—$CH_3$, $(R^7)_m$ is 4-Cl and the combination of $R^1$ and $R^6$ for a compound corresponds in each case to one row of Table A Table 545
Compounds of the formula I.5A*, in which X is N—$C_2H_5$, $(R^7)_m$ is 4-Cl and the combination of $R^1$ and $R^6$ for a compound corresponds in each case to one row of Table A Table 546
Compounds of the formula I.5A*, in which X is N-n-$C_3H_7$, $(R^7)_m$ is 4-Cl and the combination of $R^1$ and $R^6$ for a compound corresponds in each case to one row of Table A Table 547
Compounds of the formula I.5A*, in which X is N—CH$(CH_3)_2$, $(R^7)_m$ is 4-Cl and the combination of $R^1$ and $R^6$ for a compound corresponds in each case to one row of Table A Table 548
Compounds of the formula I.5A*, in which X is N-n-$C_4H_9$, $(R^7)_m$ is 4-Cl and the combination of $R^1$ and $R^6$ for a compound corresponds in each case to one row of Table A Table 549
Compounds of the formula I.5A*, in which X is N—$CH_2CH$=$CH_2$, $(R^7)_m$ is 4-Cl and the combination of $R^1$ and $R^6$ for a compound corresponds in each case to one row of Table A Table 550
Compounds of the formula I.5A*, in which X is N—$CH_2C$≡CH, $(R^7)_m$ is 4-Cl and the combination of $R^1$ and $R^6$ for a compound corresponds in each case to one row of Table A Table 551
Compounds of the formula I.5A*, in which X is N—$CH_2CN$, $(R^7)_m$ is 4-Cl and the combination of $R^1$ and $R^6$ for a compound corresponds in each case to one row of Table A Table 552
Compounds of the formula I.5A*, in which X is N—$CH_2CF_3$, $(R^7)_m$ is 4-Cl and the combination of $R^1$ and $R^6$ for a compound corresponds in each case to one row of Table A Table 553
Compounds of the formula I.5A*, in which X is N—$CH_2C_6H_5$, $(R^7)_m$ is 4-Cl and the combination of $R^1$ and $R^6$ for a compound corresponds in each case to one row of Table A Table 554
Compounds of the formula I.5A*, in which X is N—H, $(R^7)_m$ is 3-F and the combination of $R^1$ and $R^6$ for a compound corresponds in each case to one row of Table A Table 555
Compounds of the formula I.5A*, in which X is N—$CH_3$, $(R^7)_m$ is 3-F and the combination of $R^1$ and $R^6$ for a compound corresponds in each case to one row of Table A Table 556
Compounds of the formula I.5A*, in which X is N—$C_2H_5$, $(R^7)_m$ is 3-F and the combination of $R^1$ and $R^6$ for a compound corresponds in each case to one row of Table A Table 557
Compounds of the formula I.5A*, in which X is N-n-$C_3H_7$, $(R^7)_m$ is 3-F and the combination of $R^1$ and $R^6$ for a compound corresponds in each case to one row of Table A Table 558
Compounds of the formula I.5A*, in which X is N—CH$(CH_3)_2$, $(R^7)_m$ is 3-F and the combination of $R^1$ and $R^6$ for a compound corresponds in each case to one row of Table A Table 559
Compounds of the formula I.5A*, in which X is N-n-$C_4H_9$, $(R^7)_m$ is 3-F and the combination of $R^1$ and $R^6$ for a compound corresponds in each case to one row of Table A Table 560
Compounds of the formula I.5A*, in which X is N—$CH_2CH$=$CH_2$, $(R^7)_m$ is 3-F and the combination of $R^1$ and $R^6$ for a compound corresponds in each case to one row of Table A Table 561
Compounds of the formula I.5A*, in which X is N—$CH_2C$≡$CH$, $(R^7)_m$ is 3-F and the combination of $R^1$ and $R^6$ for a compound corresponds in each case to one row of Table A Table 562
Compounds of the formula I.5A*, in which X is N—$CH_2CN$, $(R^7)_m$ is 3-F and the combination of $R^1$ and $R^6$ for a compound corresponds in each case to one row of Table A Table 563
Compounds of the formula I.5A*, in which X is N—$CH_2CF_3$, $(R^7)_m$ is 3-F and the combination of $R^1$ and $R^6$ for a compound corresponds in each case to one row of Table A Table 564
Compounds of the formula I.5A*, in which X is N—$CH_2C_6H_5$, $(R^7)_m$ is 3-F and the combination of $R^1$ and $R^6$ for a compound corresponds in each case to one row of Table A Table 565
Compounds of the formula I.5A*, in which X is N—H, $(R^7)_m$ is 4-F and the combination of $R^1$ and $R^6$ for a compound corresponds in each case to one row of Table A Table 566
Compounds of the formula I.5A*, in which X is N—$CH_3$, $(R^7)_m$ is 4-F and the combination of $R^1$ and $R^6$ for a compound corresponds in each case to one row of Table A Table 567
Compounds of the formula I.5A*, in which X is N—$C_2H_5$, $(R^7)_m$ is 4-F and the combination of $R^1$ and $R^6$ for a compound corresponds in each case to one row of Table A Table 568
Compounds of the formula I.5A*, in which X is N-n-$C_3H_7$, $(R^7)_m$ is 4-F and the combination of $R^1$ and $R^6$ for a compound corresponds in each case to one row of Table A Table 569
Compounds of the formula I.5A*, in which X is N—CH($CH_3$)$_2$, $(R^7)_m$ is 4-F and the combination of $R^1$ and $R^6$ for a compound corresponds in each case to one row of Table A Table 570
Compounds of the formula I.5A*, in which X is N-n-$C_4H_9$, $(R^7)_m$ is 4-F and the combination of $R^1$ and $R^6$ for a compound corresponds in each case to one row of Table A Table 571
Compounds of the formula I.5A*, in which X is N—$CH_2CH$=$CH_2$, $(R^7)_m$ is 4-F and the combination of $R^1$ and $R^6$ for a compound corresponds in each case to one row of Table A Table 572
Compounds of the formula I.5A*, in which X is N—$CH_2C$≡$CH$, $(R^7)_m$ is 4-F and the combination of $R^1$ and $R^6$ for a compound corresponds in each case to one row of Table A Table 573
Compounds of the formula I.5A*, in which X is N—$CH_2CN$, $(R^7)_m$ is 4-F and the combination of $R^1$ and $R^6$ for a compound corresponds in each case to one row of Table A Table 574
Compounds of the formula I.5A*, in which X is N—$CH_2CF_3$, $(R^7)_m$ is 4-F and the combination of $R^1$ and $R^6$ for a compound corresponds in each case to one row of Table A Table 575
Compounds of the formula I.5A*, in which X is N—$CH_2C_6H_5$, $(R^7)_m$ is 4-F and the combination of $R^1$ and $R^6$ for a compound corresponds in each case to one row of Table A Table 576
Compounds of the formula I.5A*, in which X is N—H, $(R^7)_m$ is 5-F and the combination of $R^1$ and $R^6$ for a compound corresponds in each case to one row of Table A Table 577
Compounds of the formula I.5A*, in which X is N—$CH_3$, $(R^7)_m$ is 5-F and the combination of $R^1$ and $R^6$ for a compound corresponds in each case to one row of Table A Table 578
Compounds of the formula I.5A*, in which X is N—$C_2H_5$, $(R^7)_m$ is 5-F and the combination of $R^1$ and $R^6$ for a compound corresponds in each case to one row of Table A Table 579
Compounds of the formula I.5A*, in which X is N-n-$C_3H_7$, $(R^7)_m$ is 5-F and the combination of $R^1$ and $R^6$ for a compound corresponds in each case to one row of Table A Table 580
Compounds of the formula I.5A*, in which X is N—CH($CH_3$)$_2$, $(R^7)_m$ is 5-F and the combination of $R^1$ and $R^6$ for a compound corresponds in each case to one row of Table A Table 581
Compounds of the formula I.5A*, in which X is N-n-$C_4H_9$, $(R^7)_m$ is 5-F and the combination of $R^1$ and $R^6$ for a compound corresponds in each case to one row of Table A Table 582
Compounds of the formula I.5A*, in which X is N—$CH_2CH$=$CH_2$, $(R^7)_m$ is 5-F and the combination of $R^1$ and $R^6$ for a compound corresponds in each case to one row of Table A Table 583
Compounds of the formula I.5A*, in which X is N—$CH_2C$≡$CH$, $(R^7)_m$ is 5-F and the combination of $R^1$ and $R^6$ for a compound corresponds in each case to one row of Table A Table 584
Compounds of the formula I.5A*, in which X is N—$CH_2CN$, $(R^7)_m$ is 5-F and the combination of $R^1$ and $R^6$ for a compound corresponds in each case to one row of Table A Table 585
Compounds of the formula I.5A*, in which X is N—$CH_2CF_3$, $(R^7)_m$ is 5-F and the combination of $R^1$ and $R^6$ for a compound corresponds in each case to one row of Table A Table 586
Compounds of the formula I.5A*, in which X is N—$CH_2C_6H_5$, $(R^7)_m$ is 5-F and the combination of $R^1$ and $R^6$ for a compound corresponds in each case to one row of Table A Table 587
Compounds of the formula I.5A*, in which X is N—H, $(R^7)_m$ is 6-F and the combination of $R^1$ and $R^6$ for a compound corresponds in each case to one row of Table A Table 588
Compounds of the formula I.5A*, in which X is N—$CH_3$, $(R^7)_m$ is 6-F and the combination of $R^1$ and $R^6$ for a compound corresponds in each case to one row of Table A Table 589
Compounds of the formula I.5A*, in which X is N—$C_2H_5$, $(R^7)_m$ is 6-F and the combination of $R^1$ and $R^6$ for a compound corresponds in each case to one row of Table A Table 590
Compounds of the formula I.5A*, in which X is N-n-$C_3H_7$, $(R^7)_m$ is 6-F and the combination of $R^1$ and $R^6$ for a compound corresponds in each case to one row of Table A Table 591
Compounds of the formula I.5A*, in which X is N—CH$(CH_3)_2$, $(R^7)_m$ is 6-F and the combination of $R^1$ and $R^6$ for a compound corresponds in each case to one row of Table A Table 592
Compounds of the formula I.5A*, in which X is N-n-$C_4H_9$, $(R^7)_m$ is 6-F and the combination of $R^1$ and $R^6$ for a compound corresponds in each case to one row of Table A Table 593
Compounds of the formula I.5A*, in which X is N—$CH_2CH$=$CH_2$, $(R^7)_m$ is 6-F and the combination of $R^1$ and $R^6$ for a compound corresponds in each case to one row of Table A Table 594
Compounds of the formula I.5A*, in which X is N—$CH_2C$≡CH, $(R^7)_m$ is 6-F and the combination of $R^1$ and $R^6$ for a compound corresponds in each case to one row of Table A Table 595
Compounds of the formula I.5A*, in which X is N—$CH_2CN$, $(R^7)_m$ is 6-F and the combination of $R^1$ and $R^6$ for a compound corresponds in each case to one row of Table A Table 596
Compounds of the formula I.5A*, in which X is N—$CH_2CF_3$, $(R^7)_m$ is 6-F and the combination of $R^1$ and $R^6$ for a compound corresponds in each case to one row of Table A Table 597
Compounds of the formula I.5A*, in which X is N—$CH_2C_6H_5$, $(R^7)_m$ is 6-F and the combination of $R^1$ and $R^6$ for a compound corresponds in each case to one row of Table A Table 598
Compounds of the formula I.5A*, in which X is N—H, $(R^7)_m$ is 4-$CF_3$ and the combination of $R^1$ and $R^6$ for a compound corresponds in each case to one row of Table A Table 599
Compounds of the formula I.5A*, in which X is N—$CH_3$, $(R^7)_m$ is 4-$CF_3$ and the combination of $R^1$ and $R^6$ for a compound corresponds in each case to one row of Table A Table 600
Compounds of the formula I.5A*, in which X is N—$C_2H_5$, $(R^7)_m$ is 4-$CF_3$ and the combination of $R^1$ and $R^6$ for a compound corresponds in each case to one row of Table A Table 601
Compounds of the formula I.5A*, in which X is N-n-$C_3H_7$, $(R^7)_m$ is 4-$CF_3$ and the combination of $R^1$ and $R^6$ for a compound corresponds in each case to one row of Table A Table 602
Compounds of the formula I.5A*, in which X is N—CH$(CH_3)_2$, $(R^7)_m$ is 4-$CF_3$ and the combination of $R^1$ and $R^6$ for a compound corresponds in each case to one row of Table A Table 603
Compounds of the formula I.5A*, in which X is N-n-$C_4H_9$, $(R^7)_m$ is 4-$CF_3$ and the combination of $R^1$ and $R^6$ for a compound corresponds in each case to one row of Table A Table 604
Compounds of the formula I.5A*, in which X is N—$CH_2CH$=$CH_2$, $(R^7)_m$ is 4-$CF_3$ and the combination of $R^1$ and $R^6$ for a compound corresponds in each case to one row of Table A Table 605
Compounds of the formula I.5A*, in which X is N—$CH_2C$≡CH, $(R^7)_m$ is 4-$CF_3$ and the combination of $R^1$ and $R^6$ for a compound corresponds in each case to one row of Table A Table 606
Compounds of the formula I.5A*, in which X is N—$CH_2CN$, $(R^7)_m$ is 4-$CF_3$ and the combination of $R^1$ and $R^6$ for a compound corresponds in each case to one row of Table A Table 607
Compounds of the formula I.5A*, in which X is N—$CH_2CF_3$, $(R^7)_m$ is 4-$CF_3$ and the combination of $R^1$ and $R^6$ for a compound corresponds in each case to one row of Table A Table 608
Compounds of the formula I.5A*, in which X is N—$CH_2C_6H_5$, $(R^7)_m$ is 4-$CF_3$ and the combination of $R^1$ and $R^6$ for a compound corresponds in each case to one row of Table A Table 609
Compounds of the formula I.5A*, in which X is N—H, $(R^7)_m$ is 5-$CF_3$ and the combination of $R^1$ and $R^6$ for a compound corresponds in each case to one row of Table A Table 610
Compounds of the formula I.5A*, in which X is N—$CH_3$, $(R^7)_m$ is 5-$CF_3$ and the combination of $R^1$ and $R^6$ for a compound corresponds in each case to one row of Table A Table 611
Compounds of the formula I.5A*, in which X is N—$C_2H_5$, $(R^7)_m$ is 5-$CF_3$ and the combination of $R^1$ and $R^6$ for a compound corresponds in each case to one row of Table A Table 612
Compounds of the formula I.5A*, in which X is N-n-$C_3H_7$, $(R^7)_m$ is 5-$CF_3$ and the combination of $R^1$ and $R^6$ for a compound corresponds in each case to one row of Table A Table 613
Compounds of the formula I.5A*, in which X is N—CH$(CH_3)_2$, $(R^7)_m$ is 5-$CF_3$ and the combination of $R^1$ and $R^6$ for a compound corresponds in each case to one row of Table A Table 614
Compounds of the formula I.5A*, in which X is N-n-$C_4H_9$, $(R^7)_m$ is 5-$CF_3$ and the combination of $R^1$ and $R^6$ for a compound corresponds in each case to one row of Table A Table 615
Compounds of the formula I.5A*, in which X is N—$CH_2CH$=$CH_2$, $(R^7)_m$ is 5-$CF_3$ and the combination of $R^1$ and $R^6$ for a compound corresponds in each case to one row of Table A Table 616
Compounds of the formula I.5A*, in which X is N—$CH_2C$≡CH, $(R^7)_m$ is 5-$CF_3$ and the combination of $R^1$ and $R^6$ for a compound corresponds in each case to one row of Table A Table 617
Compounds of the formula I.5A*, in which X is N—$CH_2CN$, $(R^7)_m$ is 5-$CF_3$ and the combination of $R^1$ and $R^6$ for a compound corresponds in each case to one row of Table A Table 618
Compounds of the formula I.5A*, in which X is N—$CH_2CF_3$, $(R^7)_m$ is 5-$CF_3$ and the combination of $R^1$ and $R^6$ for a compound corresponds in each case to one row of Table A Table 619
Compounds of the formula I.5A*, in which X is N—$CH_2C_6H_5$, $(R^7)_m$ is 5-$CF_3$ and the combination of $R^1$ and $R^6$ for a compound corresponds in each case to one row of Table A Table 620
Compounds of the formula I.5A*, in which X is N—H, $(R^7)_m$ is 3,6-$F_2$ and the combination of $R^1$ and $R^6$ for a compound corresponds in each case to one row of Table A Table 621
Compounds of the formula I.5A*, in which X is N—$CH_3$, $(R^7)_m$ is 3,6-$F_2$ and the combination of $R^1$ and $R^6$ for a compound corresponds in each case to one row of Table A Table 622
Compounds of the formula I.5A*, in which X is N—$C_2H_5$, $(R^7)_m$ is 3,6-$F_2$ and the combination of $R^1$ and $R^6$ for a compound corresponds in each case to one row of Table A Table 623
Compounds of the formula I.5A*, in which X is N-n-$C_3H_7$, $(R^7)_m$ is 3,6-$F_2$ and the combination of $R^1$ and $R^6$ for a compound corresponds in each case to one row of Table A Table 624
Compounds of the formula I.5A*, in which X is N—CH$(CH_3)_2$, $(R^7)_m$ is 3,6-$F_2$ and the combination of $R^1$ and $R^6$ for a compound corresponds in each case to one row of Table A Table 625
Compounds of the formula I.5A*, in which X is N-n-$C_4H_9$, $(R^7)_m$ is 3,6-$F_2$ and the combination of $R^1$ and $R^6$ for a compound corresponds in each case to one row of Table A Table 626
Compounds of the formula I.5A*, in which X is N—$CH_2CH$=$CH_2$, $(R^7)_m$ is 3,6-$F_2$ and the combination of $R^1$ and $R^6$ for a compound corresponds in each case to one row of Table A Table 627
Compounds of the formula I.5A*, in which X is N—$CH_2C$≡$CH$, $(R^7)_m$ is 3,6-$F_2$ and the combination of $R^1$ and $R^6$ for a compound corresponds in each case to one row of Table A Table 628
Compounds of the formula I.5A*, in which X is N—$CH_2CN$, $(R^7)_m$ is 3,6-$F_2$ and the combination of $R^1$ and $R^6$ for a compound corresponds in each case to one row of Table A Table 629
Compounds of the formula I.5A*, in which X is N—$CH_2CF_3$, $(R^7)_m$ is 3,6-$F_2$ and the combination of $R^1$ and $R^6$ for a compound corresponds in each case to one row of Table A Table 630
Compounds of the formula I.5A*, in which X is N—$CH_2C_6H_5$, $(R^7)_m$ is 3,6-$F_2$ and the combination of $R^1$ and $R^6$ for a compound corresponds in each case to one row of Table A

| No. | $R^1$ | $R^6$ |
|---|---|---|
| A-1 | OH | Br |
| A-2 | $OCH_3$ | Br |
| A-3 | $OC(O)CH_3$ | Br |
| A-4 | $OC(O)CH_2CH_3$ | Br |
| A-5 | $OC(O)CH(CH_3)_2$ | Br |
| A-6 | $OC(O)C(CH_3)_3$ | Br |
| A-7 | $OC(O)$-c-$C_3H_5$ | Br |
| A-8 | $OC(O)$—$C_6H_5$ | Br |
| A-9 | $OC(O)$—$CH_2C_6H_5$ | Br |
| A-10 | $OC(O)CH_2Cl$ | Br |
| A-11 | $OC(O)$—$CF_3$ | Br |
| A-12 | $OC(O)$—$CH_2OCH_3$ | Br |
| A-13 | $OC(O)$—$N(CH_3)_2$ | Br |
| A-14 | $OC(O)$—$OCH_2CH_3$ | Br |
| A-15 | $OS(O)_2$—$CH_3$ | Br |
| A-16 | $OS(O)_2$—$C_2H_5$ | Br |
| A-17 | $OS(O)_2$—$C_3H_7$ | Br |
| A-18 | $OS(O)_2$—$CH(CH_3)_2$ | Br |
| A-19 | $OS(O)_2$—$C_6H_5$ | Br |
| A-20 | $OS(O)_2$—T1 | Br |
| A-21 | $OS(O)_2$—T2 | Br |
| A-22 | $OS(O)_2$—T3 | Br |
| A-23 | $OS(O)_2$—T4 | Br |
| A-24 | $OS(O)_2$—T5 | Br |
| A-25 | $OS(O)_2$—T6 | Br |
| A-26 | $OS(O)_2$—T7 | Br |
| A-27 | $OS(O)_2$—T8 | Br |
| A-28 | $OS(O)_2$—T9 | Br |
| A-29 | $OS(O)_2$—T10 | Br |
| A-30 | $OS(O)_2$—T11 | Br |
| A-31 | $OS(O)_2$—T12 | Br |
| A-32 | OH | Cl |
| A-33 | $OCH_3$ | Cl |
| A-34 | $OC(O)CH_3$ | Cl |
| A-35 | $OC(O)CH_2CH_3$ | Cl |
| A-36 | $OC(O)CH(CH_3)_2$ | Cl |
| A-37 | $OC(O)C(CH_3)_3$ | Cl |
| A-38 | $OC(O)$-c-$C_3H_5$ | Cl |
| A-39 | $OC(O)$—$C_6H_5$ | Cl |
| A-40 | $OC(O)$—$CH_2C_6H_5$ | Cl |
| A-41 | $OC(O)CH_2Cl$ | Cl |
| A-42 | $OC(O)$—$CF_3$ | Cl |
| A-43 | $OC(O)$—$CH_2OCH_3$ | Cl |
| A-44 | $OC(O)$—$N(CH_3)_2$ | Cl |
| A-45 | $OC(O)$—$OCH_2CH_3$ | Cl |
| A-46 | $OS(O)_2$—$CH_3$ | Cl |
| A-47 | $OS(O)_2$—$C_2H_5$ | Cl |
| A-48 | $OS(O)_2$—$C_3H_7$ | Cl |
| A-49 | $OS(O)_2$—$CH(CH_3)_2$ | Cl |
| A-50 | $OS(O)_2$—$C_6H_5$ | Cl |
| A-51 | $OS(O)_2$—T1 | Cl |
| A-52 | $OS(O)_2$—T2 | Cl |
| A-53 | $OS(O)_2$—T3 | Cl |
| A-54 | $OS(O)_2$—T4 | Cl |
| A-55 | $OS(O)_2$—T5 | Cl |
| A-56 | $OS(O)_2$—T6 | Cl |
| A-57 | $OS(O)_2$—T7 | Cl |
| A-58 | $OS(O)_2$—T8 | Cl |
| A-59 | $OS(O)_2$—T9 | Cl |
| A-60 | $OS(O)_2$—T10 | Cl |
| A-61 | $OS(O)_2$—T11 | Cl |
| A-62 | $OS(O)_2$—T12 | Cl |
| A-63 | OH | F |
| A-64 | $OCH_3$ | F |
| A-65 | $OC(O)CH_3$ | F |
| A-66 | $OC(O)CH_2CH_3$ | F |
| A-67 | $OC(O)CH(CH_3)_2$ | F |
| A-68 | $OC(O)C(CH_3)_3$ | F |
| A-69 | $OC(O)$-c-$C_3H_5$ | F |
| A-70 | $OC(O)$—$C_6H_5$ | F |
| A-71 | $OC(O)$—$CH_2C_6H_5$ | F |
| A-72 | $OC(O)CH_2Cl$ | F |
| A-73 | $OC(O)$—$CF_3$ | F |
| A-74 | $OC(O)$—$CH_2OCH_3$ | F |
| A-75 | $OC(O)$—$N(CH_3)_2$ | F |
| A-76 | $OC(O)$—$OCH_2CH_3$ | F |
| A-77 | $OS(O)_2$—$CH_3$ | F |
| A-78 | $OS(O)_2$—$C_2H_5$ | F |
| A-79 | $OS(O)_2$—$C_3H_7$ | F |
| A-80 | $OS(O)_2$—$CH(CH_3)_2$ | F |
| A-81 | $OS(O)_2$—$C_6H_5$ | F |
| A-82 | $OS(O)_2$—T1 | F |
| A-83 | $OS(O)_2$—T2 | F |
| A-84 | $OS(O)_2$—T3 | F |
| A-85 | $OS(O)_2$—T4 | F |
| A-86 | $OS(O)_2$—T5 | F |
| A-87 | $OS(O)_2$—T6 | F |
| A-88 | $OS(O)_2$—T7 | F |
| A-89 | $OS(O)_2$—T8 | F |
| A-90 | $OS(O)_2$—T9 | F |
| A-91 | $OS(O)_2$—T10 | F |
| A-92 | $OS(O)_2$—T11 | F |
| A-93 | $OS(O)_2$—T12 | F |
| A-94 | OH | $NO_2$ |
| A-95 | $OCH_3$ | $NO_2$ |
| A-96 | $OC(O)CH_3$ | $NO_2$ |

-continued

| No. | R¹ | R⁶ |
|---|---|---|
| A-97 | OC(O)CH₂CH₃ | NO₂ |
| A-98 | OC(O)CH(CH₃)₂ | NO₂ |
| A-99 | OC(O)C(CH₃)₃ | NO₂ |
| A-100 | OC(O)-c-C₃H₅ | NO₂ |
| A-101 | OC(O)—C₆H₅ | NO₂ |
| A-102 | OC(O)—CH₂C₆H₅ | NO₂ |
| A-103 | OC(O)CH₂Cl | NO₂ |
| A-104 | OC(O)—CF₃ | NO₂ |
| A-105 | OC(O)—CH₂OCH₃ | NO₂ |
| A-106 | OC(O)—N(CH₃)₂ | NO₂ |
| A-107 | OC(O)—OCH₂CH₃ | NO₂ |
| A-108 | OS(O)₂—CH₃ | NO₂ |
| A-109 | OS(O)₂—C₂H₅ | NO₂ |
| A-110 | OS(O)₂—C₃H₇ | NO₂ |
| A-111 | OS(O)₂—CH(CH₃)₂ | NO₂ |
| A-112 | OS(O)₂—C₆H₅ | NO₂ |
| A-113 | OS(O)₂—T1 | NO₂ |
| A-114 | OS(O)₂—T2 | NO₂ |
| A-115 | OS(O)₂—T3 | NO₂ |
| A-116 | OS(O)₂—T4 | NO₂ |
| A-117 | OS(O)₂—T5 | NO₂ |
| A-118 | OS(O)₂—T6 | NO₂ |
| A-119 | OS(O)₂—T7 | NO₂ |
| A-120 | OS(O)₂—T8 | NO₂ |
| A-121 | OS(O)₂—T9 | NO₂ |
| A-122 | OS(O)₂—T10 | NO₂ |
| A-123 | OS(O)₂—T11 | NO₂ |
| A-124 | OS(O)₂—T12 | NO₂ |
| A-125 | OH | CN |
| A-126 | OCH₃ | CN |
| A-127 | OC(O)CH₃ | CN |
| A-128 | OC(O)CH₂CH₃ | CN |
| A-129 | OC(O)CH(CH₃)₂ | CN |
| A-130 | OC(O)C(CH₃)₃ | CN |
| A-131 | OC(O)-c-C₃H₅ | CN |
| A-132 | OC(O)—C₆H₅ | CN |
| A-133 | OC(O)—CH₂C₆H₅ | CN |
| A-134 | OC(O)CH₂Cl | CN |
| A-135 | OC(O)—CF₃ | CN |
| A-136 | OC(O)—CH₂OCH₃ | CN |
| A-137 | OC(O)—N(CH₃)₂ | CN |
| A-138 | OC(O)—OCH₂CH₃ | CN |
| A-139 | OS(O)₂—CH₃ | CN |
| A-140 | OS(O)₂—C₂H₅ | CN |
| A-141 | OS(O)₂—C₃H₇ | CN |
| A-142 | OS(O)₂—CH(CH₃)₂ | CN |
| A-143 | OS(O)₂—C₆H₅ | CN |
| A-144 | OS(O)₂—T1 | CN |
| A-145 | OS(O)₂—T2 | CN |
| A-146 | OS(O)₂—T3 | CN |
| A-147 | OS(O)₂—T4 | CN |
| A-148 | OS(O)₂—T5 | CN |
| A-149 | OS(O)₂—T6 | CN |
| A-150 | OS(O)₂—T7 | CN |
| A-151 | OS(O)₂—T8 | CN |
| A-152 | OS(O)₂—T9 | CN |
| A-153 | OS(O)₂—T10 | CN |
| A-154 | OS(O)₂—T11 | CN |
| A-155 | OS(O)₂—T12 | CN |
| A-156 | OH | CH₃ |
| A-157 | OCH₃ | CH₃ |
| A-158 | OC(O)CH₃ | CH₃ |
| A-159 | OC(O)CH₂CH₃ | CH₃ |
| A-160 | OC(O)CH(CH₃)₂ | CH₃ |
| A-161 | OC(O)C(CH₃)₃ | CH₃ |
| A-162 | OC(O)-c-C₃H₅ | CH₃ |
| A-163 | OC(O)—C₆H₅ | CH₃ |
| A-164 | OC(O)—CH₂C₆H₅ | CH₃ |
| A-165 | OC(O)CH₂Cl | CH₃ |
| A-166 | OC(O)—CF₃ | CH₃ |
| A-167 | OC(O)—CH₂OCH₃ | CH₃ |
| A-168 | OC(O)—N(CH₃)₂ | CH₃ |
| A-169 | OC(O)—OCH₂CH₃ | CH₃ |
| A-170 | OS(O)₂—CH₃ | CH₃ |
| A-171 | OS(O)₂—C₂H₅ | CH₃ |
| A-172 | OS(O)₂—C₃H₇ | CH₃ |
| A-173 | OS(O)₂—CH(CH₃)₂ | CH₃ |
| A-174 | OS(O)₂—C₆H₅ | CH₃ |
| A-175 | OS(O)₂—T1 | CH₃ |
| A-176 | OS(O)₂—T2 | CH₃ |
| A-177 | OS(O)₂—T3 | CH₃ |
| A-178 | OS(O)₂—T4 | CH₃ |
| A-179 | OS(O)₂—T5 | CH₃ |
| A-180 | OS(O)₂—T6 | CH₃ |
| A-181 | OS(O)₂—T7 | CH₃ |
| A-182 | OS(O)₂—T8 | CH₃ |
| A-183 | OS(O)₂—T9 | CH₃ |
| A-184 | OS(O)₂—T10 | CH₃ |
| A-185 | OS(O)₂—T11 | CH₃ |
| A-186 | OS(O)₂—T12 | CH₃ |
| A-187 | OH | OCH₃ |
| A-188 | OCH₃ | OCH₃ |
| A-189 | OC(O)CH₃ | OCH₃ |
| A-190 | OC(O)CH₂CH₃ | OCH₃ |
| A-191 | OC(O)CH(CH₃)₂ | OCH₃ |
| A-192 | OC(O)C(CH₃)₃ | OCH₃ |
| A-193 | OC(O)-c-C₃H₅ | OCH₃ |
| A-194 | OC(O)—C₆H₅ | OCH₃ |
| A-195 | OC(O)—CH₂C₆H₅ | OCH₃ |
| A-196 | OC(O)CH₂Cl | OCH₃ |
| A-197 | OC(O)—CF₃ | OCH₃ |
| A-198 | OC(O)—CH₂OCH₃ | OCH₃ |
| A-199 | OC(O)—N(CH₃)₂ | OCH₃ |
| A-200 | OC(O)—OCH₂CH₃ | OCH₃ |
| A-201 | OS(O)₂—CH₃ | OCH₃ |
| A-202 | OS(O)₂—C₂H₅ | OCH₃ |
| A-203 | OS(O)₂—C₃H₇ | OCH₃ |
| A-204 | OS(O)₂—CH(CH₃)₂ | OCH₃ |
| A-205 | OS(O)₂—C₆H₅ | OCH₃ |
| A-206 | OS(O)₂—T1 | OCH₃ |
| A-207 | OS(O)₂—T2 | OCH₃ |
| A-208 | OS(O)₂—T3 | OCH₃ |
| A-209 | OS(O)₂—T4 | OCH₃ |
| A-210 | OS(O)₂—T5 | OCH₃ |
| A-211 | OS(O)₂—T6 | OCH₃ |
| A-212 | OS(O)₂—T7 | OCH₃ |
| A-213 | OS(O)₂—T8 | OCH₃ |
| A-214 | OS(O)₂—T9 | OCH₃ |
| A-215 | OS(O)₂—T10 | OCH₃ |
| A-216 | OS(O)₂—T11 | OCH₃ |
| A-217 | OS(O)₂—T12 | OCH₃ |
| A-218 | OH | CHF₂ |
| A-219 | OCH₃ | CHF₂ |
| A-220 | OC(O)CH₃ | CHF₂ |
| A-221 | OC(O)CH₂CH₃ | CHF₂ |
| A-222 | OC(O)CH(CH₃)₂ | CHF₂ |
| A-223 | OC(O)C(CH₃)₃ | CHF₂ |
| A-224 | OC(O)-c-C₃H₅ | CHF₂ |
| A-225 | OC(O)—C₆H₅ | CHF₂ |
| A-226 | OC(O)—CH₂C₆H₅ | CHF₂ |
| A-227 | OC(O)CH₂Cl | CHF₂ |
| A-228 | OC(O)—CF₃ | CHF₂ |
| A-229 | OC(O)—CH₂OCH₃ | CHF₂ |
| A-230 | OC(O)—N(CH₃)₂ | CHF₂ |
| A-231 | OC(O)—OCH₂CH₃ | CHF₂ |
| A-232 | OS(O)₂—CH₃ | CHF₂ |
| A-233 | OS(O)₂—C₂H₅ | CHF₂ |
| A-234 | OS(O)₂—C₃H₇ | CHF₂ |
| A-235 | OS(O)₂—CH(CH₃)₂ | CHF₂ |
| A-236 | OS(O)₂—C₆H₅ | CHF₂ |
| A-237 | OS(O)₂—T1 | CHF₂ |
| A-238 | OS(O)₂—T2 | CHF₂ |
| A-239 | OS(O)₂—T3 | CHF₂ |
| A-240 | OS(O)₂—T4 | CHF₂ |
| A-241 | OS(O)₂—T5 | CHF₂ |
| A-242 | OS(O)₂—T6 | CHF₂ |
| A-243 | OS(O)₂—T7 | CHF₂ |
| A-244 | OS(O)₂—T8 | CHF₂ |
| A-245 | OS(O)₂—T9 | CHF₂ |
| A-246 | OS(O)₂—T10 | CHF₂ |
| A-247 | OS(O)₂—T11 | CHF₂ |
| A-248 | OS(O)₂—T12 | CHF₂ |
| A-249 | OH | CF₃ |
| A-250 | OCH₃ | CF₃ |
| A-251 | OC(O)CH₃ | CF₃ |
| A-252 | OC(O)CH₂CH₃ | CF₃ |

| No. | R¹ | R⁶ |
|---|---|---|
| A-253 | OC(O)CH(CH₃)₂ | CF₃ |
| A-254 | OC(O)C(CH₃)₃ | CF₃ |
| A-255 | OC(O)-c-C₃H₅ | CF₃ |
| A-256 | OC(O)—C₆H₅ | CF₃ |
| A-257 | OC(O)—CH₂C₆H₅ | CF₃ |
| A-258 | OC(O)CH₂Cl | CF₃ |
| A-259 | OC(O)—CF₃ | CF₃ |
| A-260 | OC(O)—CH₂OCH₃ | CF₃ |
| A-261 | OC(O)—N(CH₃)₂ | CF₃ |
| A-262 | OC(O)—OCH₂CH₃ | CF₃ |
| A-263 | OS(O)₂—CH₃ | CF₃ |
| A-264 | OS(O)₂—C₂H₅ | CF₃ |
| A-265 | OS(O)₂—C₃H₇ | CF₃ |
| A-266 | OS(O)₂—CH(CH₃)₂ | CF₃ |
| A-267 | OS(O)₂—C₆H₅ | CF₃ |
| A-268 | OS(O)₂—T1 | CF₃ |
| A-269 | OS(O)₂—T2 | CF₃ |
| A-270 | OS(O)₂—T3 | CF₃ |
| A-271 | OS(O)₂—T4 | CF₃ |
| A-272 | OS(O)₂—T5 | CF₃ |
| A-273 | OS(O)₂—T6 | CF₃ |
| A-274 | OS(O)₂—T7 | CF₃ |
| A-275 | OS(O)₂—T8 | CF₃ |
| A-276 | OS(O)₂—T9 | CF₃ |
| A-277 | OS(O)₂—T10 | CF₃ |
| A-278 | OS(O)₂—T11 | CF₃ |
| A-279 | OS(O)₂—T12 | CF₃ |
| A-280 | OH | OCHF₂ |
| A-281 | OCH₃ | OCHF₂ |
| A-282 | OC(O)CH₃ | OCHF₂ |
| A-283 | OC(O)CH₂CH₃ | OCHF₂ |
| A-284 | OC(O)CH(CH₃)₂ | OCHF₂ |
| A-285 | OC(O)C(CH₃)₃ | OCHF₂ |
| A-286 | OC(O)-c-C₃H₅ | OCHF₂ |
| A-287 | OC(O)—C₆H₅ | OCHF₂ |
| A-288 | OC(O)—CH₂C₆H₅ | OCHF₂ |
| A-289 | OC(O)CH₂Cl | OCHF₂ |
| A-290 | OC(O)—CF₃ | OCHF₂ |
| A-291 | OC(O)—CH₂OCH₃ | OCHF₂ |
| A-292 | OC(O)—N(CH₃)₂ | OCHF₂ |
| A-293 | OC(O)—OCH₂CH₃ | OCHF₂ |
| A-294 | OS(O)₂—CH₃ | OCHF₂ |
| A-295 | OS(O)₂—C₂H₅ | OCHF₂ |
| A-296 | OS(O)₂—C₃H₇ | OCHF₂ |
| A-297 | OS(O)₂—CH(CH₃)₂ | OCHF₂ |
| A-298 | OS(O)₂—C₆H₅ | OCHF₂ |
| A-299 | OS(O)₂—T1 | OCHF₂ |
| A-300 | OS(O)₂—T2 | OCHF₂ |
| A-301 | OS(O)₂—T3 | OCHF₂ |
| A-302 | OS(O)₂—T4 | OCHF₂ |
| A-303 | OS(O)₂—T5 | OCHF₂ |
| A-304 | OS(O)₂—T6 | OCHF₂ |
| A-305 | OS(O)₂—T7 | OCHF₂ |
| A-306 | OS(O)₂—T8 | OCHF₂ |
| A-307 | OS(O)₂—T9 | OCHF₂ |
| A-308 | OS(O)₂—T10 | OCHF₂ |
| A-309 | OS(O)₂—T11 | OCHF₂ |
| A-310 | OS(O)₂—T12 | OCHF₂ |
| A-311 | OH | OCF₃ |
| A-312 | OCH₃ | OCF₃ |
| A-313 | OC(O)CH₃ | OCF₃ |
| A-314 | OC(O)CH₂CH₃ | OCF₃ |
| A-315 | OC(O)CH(CH₃)₂ | OCF₃ |
| A-316 | OC(O)C(CH₃)₃ | OCF₃ |
| A-317 | OC(O)-c-C₃H₅ | OCF₃ |
| A-318 | OC(O)—C₆H₅ | OCF₃ |
| A-319 | OC(O)—CH₂C₆H₅ | OCF₃ |
| A-320 | OC(O)CH₂Cl | OCF₃ |
| A-321 | OC(O)—CF₃ | OCF₃ |
| A-322 | OC(O)—CH₂OCH₃ | OCF₃ |
| A-323 | OC(O)—N(CH₃)₂ | OCF₃ |
| A-324 | OC(O)—OCH₂CH₃ | OCF₃ |
| A-325 | OS(O)₂—CH₃ | OCF₃ |
| A-326 | OS(O)₂—C₂H₅ | OCF₃ |
| A-327 | OS(O)₂—C₃H₇ | OCF₃ |
| A-328 | OS(O)₂—CH(CH₃)₂ | OCF₃ |
| A-329 | OS(O)₂—C₆H₅ | OCF₃ |
| A-330 | OS(O)₂—T1 | OCF₃ |
| A-331 | OS(O)₂—T2 | OCF₃ |
| A-332 | OS(O)₂—T3 | OCF₃ |
| A-333 | OS(O)₂—T4 | OCF₃ |
| A-334 | OS(O)₂—T5 | OCF₃ |
| A-335 | OS(O)₂—T6 | OCF₃ |
| A-336 | OS(O)₂—T7 | OCF₃ |
| A-337 | OS(O)₂—T8 | OCF₃ |
| A-338 | OS(O)₂—T9 | OCF₃ |
| A-339 | OS(O)₂—T10 | OCF₃ |
| A-340 | OS(O)₂—T11 | OCF₃ |
| A-341 | OS(O)₂—T12 | OCF₃ |

T1 = NH(4-CH₃—C₆H₄)
T2 = N(CH₃)₂
T3 = N(CH₃)CH₂CH₃
T4 = N(CH₃)C₃H₇
T5 = N(CH₃)CH(CH₃)₂
T6 = NH(2-Cl-6-COOH—C₆H₃)
T7 = NH(2,6-Cl₂—C₆H₃)
T8 = NH(2,6-F₂—C₆H₃)
T9 = NH(2,6-Cl₂-3-CH₃—C₆H₂)
T10 = NH(2-CF₃-6-CH₂CHF₂—C₆H₃)
T11 = NH(2-CF₃-6-OCF₃—C₆H₃)
T12 = NH(2-CF₃-6-OCH₂CHF₂—C₆H₃)

The compounds I and their agriculturally useful salts are suitable, both as isomer mixtures and in the form of the pure isomers, as herbicides. They are suitable as such or as an appropriately formulated composition. The herbicidal compositions comprising the compound I, in particular the preferred aspects thereof, control vegetation on non-crop areas very efficiently, especially at high rates of application. They act against broad-leaved weeds and weed grasses in crops such as wheat, rice, corn, soybeans and cotton without causing any significant damage to the crop plants. This effect is mainly observed at low rates of application.

Depending on the application method in question, the compounds I, in particular the preferred aspects thereof, or compositions comprising them can additionally be employed in a further number of crop plants for eliminating unwanted plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays.*

The term "crop plants" also includes plants which have been modified by breeding, mutagenesis or genetic engineering. Genetically modified plants are plants whose genetic material has been modified in a manner which does not occur under natural conditions by crossing, mutations or natural recombination (i.e. reassembly of the genetic information). Here, in general, one or more genes are integrated into the genetic material of the plant to improve the properties of the plant.

Accordingly, the term "crop plants" also includes plants which, by breeding and genetic engineering, have acquired tolerance to certain classes of herbicides, such as hydroxyphenylpyruvate dioxygenase (HPPD) inhibitors, acetolactate synthase (ALS) inhibitors, such as, for example, sulfonylureas (EP-A 257 993, U.S. Pat. No. 5,013,659) or imidazolinones (see, for example, U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors, such as, for example, glyphosate (see, for example, WO 92/00377), glutamine synthetase (GS) inhibitors, such as, for example, glufosinate (see, for example, EP-A 242 236, EP-A 242 246), or oxynil herbicides (see, for example, U.S. Pat. No. 5,559,024).

Numerous crop plants, for example Clearfield® oilseed rape, tolerant to imidazolinones, for example imazamox, have been generated with the aid of classic breeding methods (mutagenesis). Crop plants such as soybeans, cotton, corn, beet and oilseed rape, resistant to glyphosate or glufosinate, which are available under the tradenames RoundupReady® (glyphosate) and Liberty Link® (glufosinate) have been generated with the aid of genetic engineering methods.

Accordingly, the term "crop plants" also includes plants which, with the aid of genetic engineering, produce one or more toxins, for example those of the bacterial strain *Bacillus* ssp. Toxins which are produced by such genetically modified plants include, for example, insecticidal proteins of *Bacillus* spp., in particular *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetative insecticidal proteins (VIPs), for example VIP1, VIP2, VIP3, or VIP3A; insecticidal proteins of nematode-colonizing bacteria, for example *Photorhabdus* spp. or *Xenorhabdus* spp.; toxins of animal organisms, for example wasp, spider or scorpion toxins; fungal toxins, for example from *Streptomycetes*; plant lectins, for example from peas or barley; agglutinins; proteinase inhibitors, for example trypsin inhibitors, serine protease inhibitors, patatin, cystatin or papain inhibitors, ribosome-inactivating proteins (RIPs), for example ricin, corn-RIP, abrin, luffin, saporin or bryodin; steroid-metabolizing enzymes, for example 3-hydroxysteroid oxidase, ecdysteroid-IDP glycosyl transferase, cholesterol oxidase, ecdysone inhibitors, or HMG-CoA reductase; ion channel blockers, for example inhibitors of sodium channels or calcium channels; juvenile hormone esterase; receptors of the diuretic hormone (helicokinin receptors); stilbene synthase, bibenzyl synthase, chitinases and glucanases. In the plants, these toxins may also be produced as pretoxins, hybrid proteins or truncated or otherwise modified proteins. Hybrid proteins are characterized by a novel combination of different protein domains (see, for example, WO 2002/015701). Further examples of such toxins or genetically modified plants which produce these toxins are disclosed in EP-A 374 753, WO 93/007278, WO 95/34656, EP-A 427 529, EP-A 451 878, WO 03/018810 and WO 03/052073. The methods for producing these genetically modified plants are known to the person skilled in the art and disclosed, for example, in the publications mentioned above. Numerous of the toxins mentioned above bestow, upon the plants by which they are produced, tolerance to pests from all taxonomic classes of arthropods, in particular to beetles (*Coeleropta*), dipterans (*Diptera*) and butterflies (*Lepidoptera*) and to nematodes (*Nematoda*).

Genetically modified plants which produce one or more genes coding for insecticidal toxins are described, for example, in the publications mentioned above, and some of them are commercially available, such as, for example, Yield-Gard® (corn varieties producing the toxin Cry1Ab), Yield-Gard® Plus (corn varieties which produce the toxins Cry1Ab and Cry3Bb1), Starlink® (corn varieties which produce the toxin Cry9c), Herculex® RW (corn varieties which produce the toxins Cry34Ab1, Cry35Ab1 and the enzyme phosphinothricin-N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf° (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France (corn varieties which produce the toxin Cry1Ab and the PAT enzyme), MIR604 from Syngenta Seeds SAS, France (corn varieties which produce a modified version of the toxin Cry3A, see WO 03/018810), MON 863 from Monsanto Europe S.A., Belgium (corn varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (corn varieties which produce the toxin Cry1F and the PAT enzyme).

Accordingly, the term "crop plants" also includes plants which, with the aid of genetic engineering, produce one or more proteins which are more robust or have increased resistance to bacterial, viral or fungal pathogens, such as, for example, pathogenesis-related proteins (PR proteins, see EP-A 0 392 225), resistance proteins (for example potato varieties producing two resistance genes against *Phytophthora infestans* from the wild Mexican potato *Solanum bulbocastanum*) or T4 lysozyme (for example potato cultivars which, by producing this protein, are resistant to bacteria such as *Erwinia amylvora*).

Accordingly, the term "crop plants" also includes plants whose productivity has been improved with the aid of genetic engineering methods, for example by enhancing the potential yield (for example biomass, grain yield, starch, oil or protein content), tolerance to drought, salt or other limiting environmental factors or resistance to pests and fungal, bacterial and viral pathogens.

The term "crop plants" also includes plants whose ingredients have been modified with the aid of genetic engineering methods in particular for improving human or animal diet, for example by oil plants producing health-promoting long-chain omega 3 fatty acids or monounsaturated omega 9 fatty acids (for example Nexera® oilseed rape).

The term "crop plants" also includes plants which have been modified with the aid of genetic engineering methods for improving the production of raw materials, for example by increasing the amylopectin content of potatoes (Amflora® potato).

Furthermore, it has been found that the compounds of the formula I are also suitable for the defoliation and/or desiccation of plant parts, for which crop plants such as cotton, potato, oilseed rape, sunflower, soybean or field beans, in particular cotton, are suitable. In this regard, there have been found compositions for the desiccation and/or defoliation of plants, processes for preparing these compositions and methods for desiccating and/or defoliating plants using the compounds of the formula I.

As desiccants, the compounds of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the readily controllable defoliation of useful plants, in particular cotton.

Moreover, a shortening of the time interval in which the individual cotton plants mature leads to an increased fiber quality after harvesting.

The compounds I, or the herbicidal compositions comprising the compounds I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in each case, they should ensure the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, if appropriate colorants and, for seed formulations, adhesives.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulation. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following:
mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the compounds of the formula I or Ia, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

The concentrations of the compounds of the formula I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The compounds I of the invention can for example be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (e.g. Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are ground to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

The compounds I or the herbicidal compositions comprising them can be applied pre- or post-emergence, or together with the seed of a crop plant. It is also possible to apply the herbicidal compositions or active compounds by applying seed, pretreated with the herbicidal compositions or active compounds, of a crop plant. If the active compounds are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the compounds of the formula I or the herbicidal compositions can be applied by treating seed.

The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term seed comprises seed of all types, such as, for example, corns, seeds, fruits, tubers, cuttings and similar forms. Here, preferably, the term seed describes corns and seeds.

The seed used can be seed of the useful plants mentioned above, but also the seed of transgenic plants or plants obtained by customary breeding methods.

The rates of application of active compound are from 0.001 to 3.0, preferably 0.01 to 1.0, kg/ha of active substance (a.s.), depending on the control target, the season, the target plants and the growth stage. To treat the seed, the compounds I are generally employed in amounts of from 0.001 to 10 kg per 100 kg of seed.

It may also be advantageous to use the compounds of the formula I in combination with safeners. Safeners are chemical compounds which prevent or reduce damage to useful plants without substantially affecting the herbicidal action of the compounds of the formula I on unwanted plants. They can be used both before sowing (for example in the treatment of seed, or on cuttings or seedlings) and before or after the emergence of the useful plant. The safeners and the compounds of the formula I can be used simultaneously or in succession. Suitable safeners are, for example, (quinolin-8- oxy)acetic acids, 1-phenyl-5-haloalkyl-1H-1,2,4-triazole-3-carboxylic acids, 1-phenyl-4,5-dihydro-5-alkyl-1H-pyrazole-3,5-dicarboxylic acids, 4,5-dihydro-5,5-diaryl-3-isoxazolecarboxylic acids, dichloroacetamides, alpha-oximinophenylacetonitriles, acetophenone oximes, 4,6-dihalo-2-phenylpyrimidines, N-[[4-(aminocarbonyl)phenyl]-sulfonyl]-2-benzamides, 1,8-naphthalic anhydride, 2-halo-4-(haloalkyl)-5-thiazolecarboxylic acids, phosphorothiolates and O-phenyl N-alkylcarbamates and their agriculturally useful salts and, provided that they have an acid function, their agriculturally useful derivatives, such as amides, esters and thioesters.

To broaden the activity spectrum and to obtain synergistic effects, the compounds of the formula I can be mixed and jointly applied with numerous representatives of other herbicidal or growth-regulating groups of active compounds or with safeners. Suitable mixing partners are, for example, 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-CF$_3$-phenyl derivatives, carbamates, quinoline carboxylic acid and its derivatives, chloroacetanilides, cyclohexenone oxime ether derivates, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils and also phenylpyrazolines and isoxazolines and their derivatives.

Moreover, it may be useful to apply the compounds I alone or in combination with other herbicides or else also mixed with further crop protection agents, jointly, for example with compositions for controlling pests or phytopathogenic fungi or bacteria. Also of interest is the miscibility with mineral salt solutions which are employed for alleviating nutritional and trace element deficiencies. Other additives such as nonphytotoxic oils and oil concentrates may also be added.

Examples of herbicides which can be used in combination with the pyridine compounds of the formula I according to the present invention are:

b1) from the group of the lipid biosynthesis inhibitors:

alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

amidosulfuron, azimsulfuron, bensulfuron, bensulfuron-methyl, bispyribac, bispyribac-sodium, chlorimuron, chlorimuron-ethyl, chlorsulfuron, cinosulfuron, cloransulam, cloransulam-methyl, cyclosulfamuron, diclosulam, ethametsulfuron, ethametsulfuron-methyl, ethoxysulfuron, flazasulfuron, florasulam, flucarbazone, flucarbazone-sodium, flucetosulfuron, flumetsulam, flupyrsulfuron, flupyrsulfuron-methyl-sodium, foramsulfuron, halosulfuron, halosulfuron-methyl, imazamethabenz, imazamethabenz-methyl, imazamox, imazapic, imazapyr, imazaquin, imazethapyr, imazosulfuron, iodosulfuron, iodosulfuron-methyl-sodium, mesosulfuron, metosulam, metsulfuron, metsulfuron-methyl, nicosulfuron, orthosulfamuron, oxasulfuron, penoxsulam, primisulfuron, primisulfuron-methyl, propoxycarbazone, propoxycarbazone-sodium, prosulfuron, pyrazosulfuron, pyrazosulfuron-ethyl, pyribenzoxim, pyrimisulfan, pyriftalid, pyriminobac, pyriminobac-methyl, pyrithiobac, pyrithiobac-sodium, pyroxsulam, rimsulfuron, sulfometuron, sulfometuron-methyl, sulfosulfuron, thiencarbazone, thiencarbazone-methyl, thifensulfuron, thifensulfuron-methyl, triasulfuron, tribenuron, tribenuron-methyl, trifloxysulfuron, triflusulfuron, triflusulfuron-methyl and tritosulfuron;

b3) from the group of the photosynthesis inhibitors:

ametryn, amicarbazone, atrazine, bentazone, bentazone-sodium, bromacil, bromofenoxim, bromoxynil and its salts and esters, chlorobromuron, chloridazone, chlorotoluron, chloroxuron, cyanazine, desmedipham, desmetryn, dimefuron, dimethametryn, diquat, diquat-dibromide, diuron, fluometuron, hexazinone, ioxynil and its salts and esters, isoproturon, isouron, karbutilate, lenacil, linuron, metamitron, methabenzthiazuron, metobenzuron, metoxuron, metribuzin, monolinuron, neburon, paraquat, paraquat-dichloride, paraquat-dimetilsulfate, pentanochlor, phenmedipham, phenmedipham-ethyl, prometon, prometryn, propanil, propazine, pyridafol, pyridate, siduron, simazine, simetryn, tebuthiuron, terbacil, terbumeton, terbuthylazine, terbutryn, thidiazuron and trietazine;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, 2-chloro-5-[3,6-dihydro-3-methyl-2,6-dioxo-4-(trifluoromethyl)-1(2H)-pyrimidinyl]-4-fluoro-N-[(isopropyl)-methylsulfamoyl]benzamide (H-1; CAS 372137-35-4), ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (H-2; CAS 353292-31-6), N-ethyl-3-(2,6-dichloro-4-trifluoromethylphenoxy)-5-methyl-1H-pyrazole-1-carboxamide (H-3; CAS 452098-92-9), N-tetrahydrofurfuryl-3-(2,6-dichloro-4-trifluoromethylphenoxy)-5-methyl-1H-pyrazole-1-carboxamide (H-4; CAS 915396-43-9), N-ethyl-3-(2-chloro-6-fluoro-4-trifluoromethylphenoxy)-5-methyl-1H-pyrazole-1-carboxamide (H-5; CAS 452099-05-7) and N-tetrahydrofurfuryl-3-(2-chloro-6-fluoro-4-trifluoromethylphenoxy)-5-methyl-1H-pyrazole-1-carboxamide (H-6; CAS 45100-03-7);

b5) from the group of the bleacher herbicides:

aclonifen, amitrol, beflubutamid, benzobicyclon, benzolenap, clomazone, diflufenican, fluridone, fluorochloridone, flurtamone, isoxaflutole, mesotrione, norflurazon, picolinafen, pyrasulfutole, pyrazolynate, pyrazoxyfen, sulcotrione, tefuryltrione, tembotrione, topramezone, 4-hydroxy-3-[[2-[(2-methoxyethoxy)methyl]-6-(trifluoromethyl)-3-pyridyl]

carbonyl]bicyclo[3.2.1]oct-3-en-2-one (H-7; CAS 352010-68-5) and 4-(3-trifluoromethylphenoxy)-2-(4-trifluoromethylphenyl)pyrimidine (H-8; CAS 180608-33-7);

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate and glufosinate-ammonium;

b8) from the group of the DHP synthase inhibitors:
asulam;

b9) from the group of the mitose inhibitors:
amiprophos, amiprophos-methyl, benfluralin, butamiphos, butralin, carbetamide, chlorpropham, chlorthal, chlorthal-dimethyl, dinitramine, dithiopyr, ethalfluralin, fluchloralin, oryzalin, pendimethalin, prodiamine, propham, propyzamide, tebutam, thiazopyr and trifluralin;

b10) from the group of the VLCFA inhibitors:
acetochlor, alachlor, anilofos, butachlor, cafenstrole, dimethachlor, dimethanamid, dimethenamid-P, diphenamid, fentrazamide, flufenacet, mefenacet, metazachlor, metolachlor, metolachlor-S, naproanilide, napropamide, pethoxamid, piperophos, pretilachlor, propachlor, propisochlor, pyroxasulfone (KIH-485) and thenylchlor;

Compounds of the formula 2:

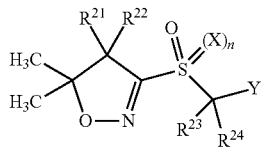

in which the variables have the following meanings:
Y is phenyl or 5- or 6-membered heteroaryl as defined at the outset, which radicals may be substituted by one to three groups $R^{aa}$; $R^{21}$, $R^{22}$, $R^{23}$, $R^{24}$ are H, halogen or $C_1$-$C_4$-alkyl; X is O or NH; N is 0 or 1.

Compounds of the formula 2 have in particular the following meanings:
Y is

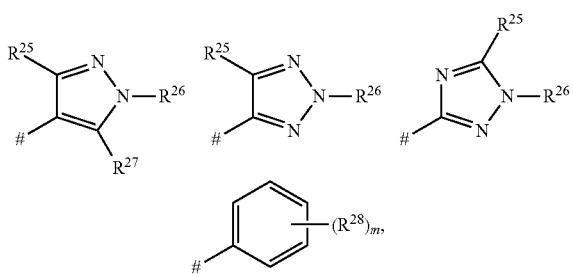

where # denotes the bond to the skeleton of the molecule; and $R^{21}$, $R^{22}$, $R^{23}$, $R^{24}$ are H, Cl, F or $CH_3$; $R^{25}$ is halogen, $C_1$-$C_4$-alkyl or $C_1$-$C_4$-haloalkyl; $R^{26}$ is $C_1$-$C_4$-alkyl; $R^{27}$ is halogen, $C_1$-$C_4$-alkoxy or $C_1$-$C_4$-haloalkoxy; $R^{28}$ is H, halogen, $C_1$-$C_4$-alkyl, $C_1$-$C_4$-haloalkyl or $C_1$-$C_4$-haloalkoxy; M is 0, 1, 2 or 3; X is oxygen; N is 0 or 1.

Preferred compounds of the formula 2 have the following meanings:
Y

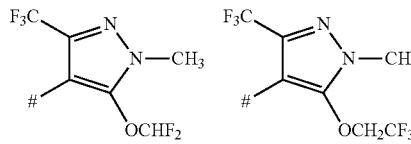

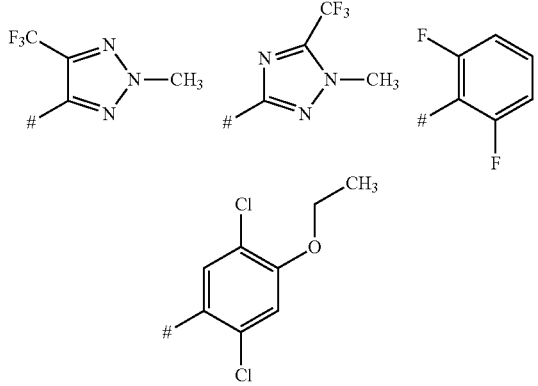

$R^{21}$ is H; $R^{22}$, $R^{23}$ are F; $R^{24}$ is H or F; X is oxygen; N is 0 or 1.

Particularly preferred compounds of the formula 2 are:
3-[5-(2,2-difluoroethoxy)-1-methyl-3-trifluoromethyl-1H-pyrazol-4-ylmethanesulfonyl]-4-fluoro-5,5-dimethyl-4,5-dihydroisoxazole (2-1); 3-{[5-(2,2-difluoroethoxy)-1-methyl-3-trifluoromethyl-1H-pyrazol-4-yl]fluoromethanesulfonyl}-5,5-dimethyl-4,5-dihydroisoxazole (2-2); 4-(4-fluoro-5,5-dimethyl-4,5-dihydroisoxazole-3-sulfonylmethyl)-2-methyl-5-trifluoromethyl-2H-[1,2,3]triazole (2-3); 4-[(5,5-dimethyl-4,5-dihydroisoxazole-3-sulfonyl)fluoromethyl]-2-methyl-5-trifluoromethyl-2H-[1,2,3]triazole (2-4); 4-(5,5-dimethyl-4,5-dihydroisoxazole-3-sulfonylmethyl)-2-methyl-5-trifluoromethyl-2H-[1,2,3]triazole (2-5); 3-{[5-(2,2-difluoroethoxy)-1-methyl-3-trifluoromethyl-1H-pyrazol-4-yl]difluoromethanesulfonyl}-5,5-dimethyl-4,5-dihydroisoxazole (2-6); 4-[(5,5-dimethyl-4,5-dihydroisoxazole-3-sulfonyl)difluoromethyl]-2-methyl-5-trifluoromethyl-2H-[1,2,3]triazole (2-7); 3-{[5-(2,2-difluoroethoxy)-1-methyl-3-trifluoromethyl-1H-pyrazol-4-yl]difluoromethanesulfonyl}-4-fluoro-5,5-dimethyl-4,5-dihydroisoxazole (2-8); 4-[difluoro-(4-fluoro-5,5-dimethyl-4,5-dihydroisoxazole-3-sulfonyl)methyl]-2-methyl-5-trifluoromethyl-2H-[1,2,3]triazole (2-9);

b11) from the group of the cellulose biosynthesis inhibitors:
chlorthiamid, dichlobenil, flupoxam and isoxaben;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorpropand its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecopropand its salts and esters, mecoprop-P and its salts and esters, picloram and its salts and esters, quinclorac, quinmerac, TBA (2,3,6) and its salts and esters, triclopyr and its salts and esters, and 5,6-dichloro-2-cyclopropyl-4-pyrimidinecarboxylic acid (H-9; CAS 858956-08-8) and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (H-10; CAS 499223-49-3) and its salts and esters.

Examples of preferred safeners C are benoxacor, cloquintocet, cyometrinil, cyprosulfamide, dichlormid, dicyclonone, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (H-11; MON4660, CAS 71526-07-3) and 2,2,5-trimethyl-3-(dichloroacetyl)-1,3-oxazolidine (H-12; R-29148, CAS 52836-31-4).

The active compounds of groups b1) to b15) and the safeners C are known herbicides and safeners, see, for example, The Compendium of Pesticide Common Names (http://www.alanwood.net/pesticides/); B. Hock, C. Fedtke, R. R. Schmidt, Herbizide [Herbicides], Georg Thieme Verlag, Stuttgart, 1995. Further herbicidally active compounds are known from WO 96/26202, WO 97/41116, WO 97/41117, WO 97/41118, WO 01/83459 and WO 2008/074991 and from W. Kramer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one pyridine compound of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one pyridine compound of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

The active compounds in the compositions described are in each case preferably present in synergistically effective amounts.

The compounds I and the compositions according to the invention may also have a plant-strengthening action. Accordingly, they are suitable for mobilizing the defense system of the plants against attack by unwanted microorganisms, such as harmful fungi, but also viruses and bacteria. Plant-strengthening (resistance-inducing) substances are to be understood as meaning, in the present context, those substances which are capable of stimulating the defense system of treated plants in such a way that, when subsequently inoculated by unwanted microorganisms, the treated plants display a substantial degree of resistance to these microorganisms.

The compounds I can be employed for protecting plants against attack by unwanted microorganisms within a certain period of time after the treatment. The period of time within which their protection is effected generally extends from 1 to 28 days, preferably from 1 to 14 days, after the treatment of the plants with the compounds I, or, after treatment of the seed, for up to 9 months after sowing.

The compounds I and the compositions according to the invention are also suitable for increasing the harvest yield.

Moreover, they have reduced toxicity and are tolerated well by the plants.

Hereinbelow, the preparation of quinolinone compounds of the formula I is illustrated by way of examples, without limiting the subject matter of the present invention to the examples shown.

PREPARATION EXAMPLES

Preparation of 6,8-Dihydroxy-7-o-tolylquinoline

Step 1: 2-Iodo-1,3-dimethoxy-4-nitrobenzene

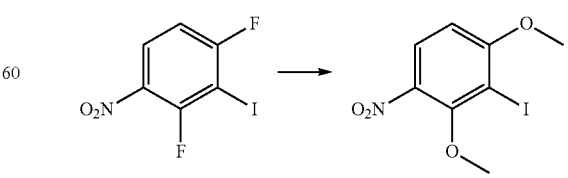

1,3-Difluoro-2-iodo-4-nitrobenzene (5.0 g, 17.5 mmol) was dissolved in 50 ml of methanol, and NaOMe (3.79 g, 70.1 mmol) was added. The solution was heated under reflux for 16 h. After concentration, the residue was chromatographed on silica gel using petroleum ether/ethyl acetate. This gave 2-iodo-1,3-dimethoxy-4-nitrobenzene (3 g) as a yellowish powder.

$^1$H-NMR (400 MHz, CDCl$_3$): 8.0 (d, 1H); 6.88 (d, 1H); 3.96 (s, 3H); 3.91 (s, 3H)

Step 2: 2,6-Dimethoxy-2'-methyl-3-nitrobiphenyl

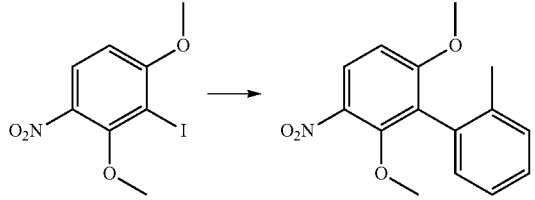

2-Iodo-1,3-dimethoxy-4-nitrobenzene (0.5 g, 1.62 mmol) was dissolved in dioxane/acetonitrile/water (10 ml/2 ml/2 ml), and 2-tolylboronic acid was added. Pd(dppf)Cl$_2$ (0.11 mg, 0.16 mmol) and K$_2$CO$_3$ (0.33 g, 2.43 mmol) were added to this, and the mixture was stirred at 90° C. for 32 h. After concentration, the residue was chromatographed on silica gel using petroleum ether/ethyl acetate. This gave 2,6-dimethoxy-2'-methyl-3-nitrobiphenyl (0.2 g) as a colorless powder.

$^1$H-NMR (400 MHz, CDCl$_3$): 7.99 (d, 1H); 7.15-7.35 (m, 4H); 6.79 (d, 1H); 3.82 (s, 3H); 3.45 (s, 3H); 2.10 (s, 3H)

Step 3: 2,6-Dimethoxy-2'-methylbiphenyl-3-ylamine

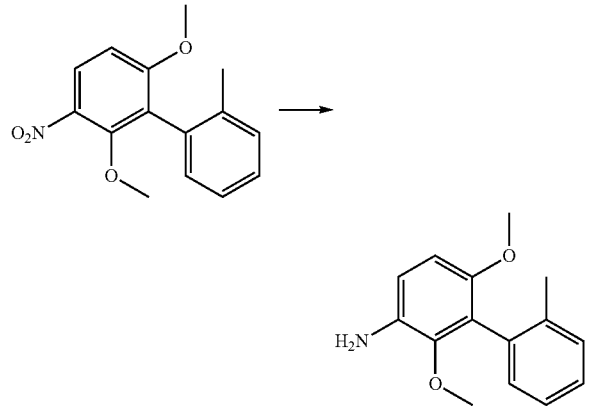

Pd/C (0.1 g) was added to 2,6-dimethoxy-2'-methyl-3-nitrobiphenyl (0.2 g, 0.73 mmol) in methanol (20 ml), and under 1 atm of H$_2$, the mixture was heated at 50° C. for 2 h. Filtration and concentration gave 2,6-dimethoxy-2'-methylbiphenyl-3-ylamine (0.14 g) as a colorless oil, which was directly reacted further.

Step 4: 6,8-Dimethoxy-7-o-tolylquinoline

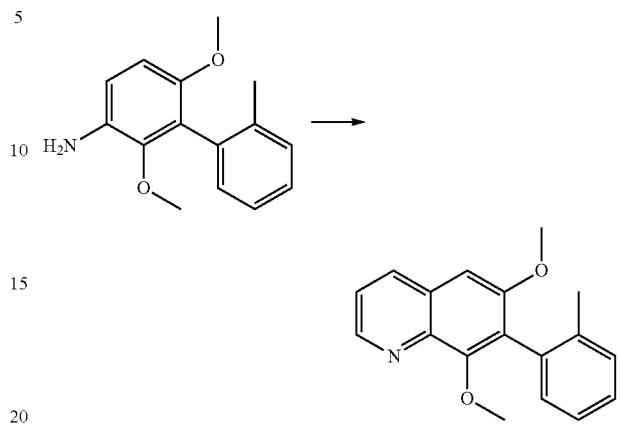

6-Dimethoxy-2'-methylbiphenyl-3-ylamine (0.14 g, 0.58 mmol), acrolein (100 mg, 1.8 mmol) and 1N HCl (4 ml) were heated at 90° C. for 2 h. After cooling, the mixture was diluted with ethyl acetate (10 ml) and neutralized with saturated NaHCO$_3$ solution, the aqueous phase was extracted 2× with ethyl acetate (3 ml) and the organic phase was dried with Na$_2$SO$_4$ and concentrated. The residue was chromatographed on silica gel using petroleum ether/ethyl acetate. This gave 6,8-dimethoxy-7-o-tolylquinoline (80 mg) as yellowish crystals.

$^1$H-NMR (400 MHz, CDCl$_3$): 8.83 (m, 1H); 8.10 (d, 1H); 7.2-7.4 (m, 5H); 6.95 (s, 1H); 3.85 (s, 3H); 3.77 (s, 3H); 2.13 (s, 3H)

Step 5: 6,8-Dihydroxy-7-o-tolylquinoline

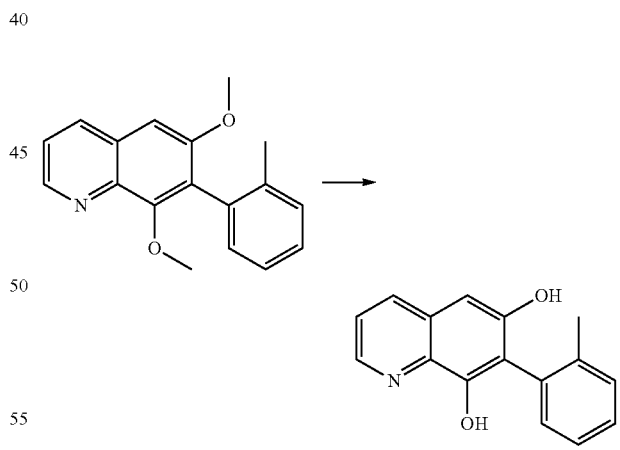

At −78° C., 1N BBr$_3$ in CH$_2$Cl$_2$ (1.5 ml, 1.5 mmol) was added to 6,8-dimethoxy-7-o-tolylquinoline (0.10 g, 0.36 mmol) in CH$_2$Cl$_2$ (5 ml), and the mixture was warmed to room temperature and stirred for 6 h. The solution was poured into ice-water and neutralized with saturated NaHCO$_3$ solution. The mixture was extracted with ethyl acetate, and the organic phase was dried with Na$_2$SO$_4$. Purification of the residue by HPLC gave 6,8-dihydroxy-7-o-tolylquinoline (7 mg) as a white powder.

$^1$H-NMR (400 MHz, CDCl$_3$): 8.63 (d, 1H); 8.05 (d, 1H); 7.30-7.45 (m, 5H); 6.89 (s, 1H); 2.21 (s, 3H)
MS (M+H): 251.9

Use Examples

The herbicidal activity of the compound of the formula I is demonstrated by the following greenhouse experiments:

The culture containers used are plastic flowerpots containing loamy sand with approximately 3.0% of humus as the substrate. The seeds of the test plants are sown separately for each species.

For the pre-emergence treatment, the active ingredients, which have been suspended or emulsified in water, are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the active ingredients.

For the post-emergence treatment, the test plants are first grown to a height of 3 to 15 cm, depending on the plant habit, and only then treated with the active ingredients which has been suspended or emulsified in water. For this purpose, the test plants are either sown directly and grown in the same containers, or they are first grown separately as seedlings and transplanted into the test containers a few days prior to treatment.

Depending on the species, the plants are kept at 10 to 25° C. or 20 to 35° C. The test period extends over 2 to 4 weeks. During this time, the plants are tended, and their response to the individual treatments is evaluated.

Evaluation is carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The invention claimed is:
1. A quinolinone compound of the formula I

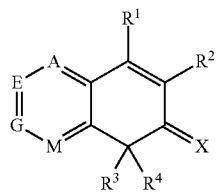

in which
$R^1$ is O—$R^A$, S(O)$_n$—$R^A$ or O—S(O)$_n$—$R^A$;
$R^A$ is hydrogen, C$_1$-C$_4$-alkyl, Z—C$_3$-C$_6$-cycloalkyl, C$_1$-C$_4$-haloalkyl, C$_2$-C$_6$-alkenyl, Z—C$_3$-C$_6$-cycloalkenyl, C$_2$-C$_6$-alkynyl, Z-(tri-C$_1$-C$_4$-alkyl)silyl, Z—C(=O)—$R^a$, Z—P(=O)(R$^a$)$_2$, NR$^i$R$^{ii}$, a 3- to 7-membered monocyclic or 9- or 10-membered bicyclic saturated, unsaturated or aromatic heterocycle which contains 1, 2, 3 or 4 heteroatoms selected from the group consisting of O, N and S, which may be partially or fully substituted by groups R$^a$ and/or R$^b$ and which is attached via carbon or nitrogen,
$R^a$ is hydrogen, OH, C$_1$-C$_8$-alkyl, C$_1$-C$_4$-haloalkyl, Z—C$_3$-C$_6$-cycloalkyl, C$_2$-C$_8$-alkenyl, Z—C$_5$-C$_6$-cycloalkenyl, C$_2$-C$_8$-alkynyl, Z—C$_1$-C$_6$-alkoxy, Z—C$_1$-C$_4$-haloalkoxy, Z—C$_3$-C$_8$-alkenyloxy, Z—C$_3$-C$_8$-alkynyloxy, NR$^i$R$^{ii}$, C$_1$-C$_6$-alkylsulfonyl, Z-(tri-C$_1$-C$_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R$^b$;
R$^i$, R$^{ii}$ independently of one another are hydrogen, C$_1$-C$_8$-alkyl, C$_1$-C$_4$-haloalkyl, C$_3$-C$_8$-alkenyl, C$_3$-C$_8$-alkynyl, Z—C$_3$-C$_6$-cycloalkyl, Z—C$_1$-C$_8$-alkoxy, Z—C$_1$-C$_8$-haloalkoxy, Z—C(=O)—$R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z; or
R$^i$ and R$^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;
Z is a covalent bond or C$_1$-C$_4$-alkylene;
n is 0, 1 or 2;
$R^2$ is phenyl, naphthyl or a 5- or 6-membered monocyclic or 9- or 10-membered bicyclic aromatic heterocycle which contains 1, 2, 3 or 4 heteroatoms selected from the group consisting of O, N and S, where the cyclic groups are unsubstituted or substituted by 1, 2, 3 or 4 groups R$^b$;
R$^b$ independently of one another are Z—CN, Z—OH, Z—NO$_2$, Z-halogen, C$_1$-C$_8$-alkyl, C$_1$-C$_4$-haloalkyl, C$_2$-C$_8$-alkenyl, C$_2$-C$_8$-alkynyl, Z—C$_1$-C$_8$-alkoxy, Z—C$_1$-C$_8$-haloalkoxy, Z—C$_3$-C$_{10}$-cycloalkyl, O—Z—C$_3$-C$_{10}$-cycloalkyl, Z—C(=O)—$R^a$, NR$^i$R$^{ii}$, Z-(tri-C$_1$-C$_4$-alkyl)silyl, Z-phenyl and S(O)$_n$R$^{bb}$,
where R$^{bb}$ is C$_1$-C$_8$-alkyl or C$_1$-C$_6$-haloalkyl and n is 0, 1 or 2;
R$^b$ together with the group R$^b$ attached to the adjacent carbon atom may also form a five- or six-membered saturated or partially or fully unsaturated ring which, in addition to carbon atoms, may contain 1, 2 or 3 heteroatoms selected from the group consisting of O, N and S;
X is O, S or N—$R^5$;
$R^3$, $R^4$, $R^5$ independently of one another are hydrogen, C$_1$-C$_6$-alkyl, C$_2$-C$_6$-alkenyl, C$_3$-C$_6$-alkynyl, Z—C$_3$-C$_{10}$-cycloalkyl, C$_1$-C$_6$-alkoxy-C$_1$-C$_6$-alkyl, C$_1$-C$_6$-cyanoalkyl, Z-phenyl, Z—C(=O)—$R^a$2 or tri-C$_1$-C$_4$-alkylsilyl;
$R^a$2 is C$_1$-C$_6$-alkyl, C$_1$-C$_4$-haloalkyl, Z—C$_1$-C$_6$-alkoxy, Z—C$_1$-C$_4$-haloalkoxy or NR$^i$R$^{ii}$;
one of A, E, G, and M is N and the other three are C—R$^c$;
R$^c$ is hydrogen or one of the groups mentioned for R$^b$;
where in the groups R$^A$, R$^3$, R$^4$ and R$^5$ and their substituents, the carbon chains and/or the cyclic groups may be partially or fully substituted by groups R$^b$,
or a N-oxide or an agriculturally suitable salt thereof.
2. The compound of the formula I according to claim 1 in which X is O.
3. The compound of the formula I according to claim 1 in which X is S.

4. The compound of the formula I according to claim 1 in which X is N—$R^5$.

5. The compound of the formula I according to claim 1 in which $R^1$ is O—$R^4$ or O—S(O)$_n$—$R^4$.

6. The compound of the formula I according to claim 1 which corresponds to the formula I.1

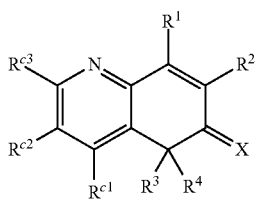

in which $R^{c1}$, $R^{c2}$ and $R^{c3}$ each correspond to a group $R^c$.

7. The compound of the formula I according to claim 1 which corresponds to the formula I.2

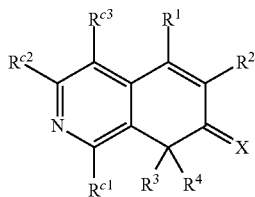

in which $R^{c1}$, $R^{c2}$ and $R^{c4}$ each correspond to a group $R^c$.

8. The compound of the formula I according to claim 1 which corresponds to the formula I.A

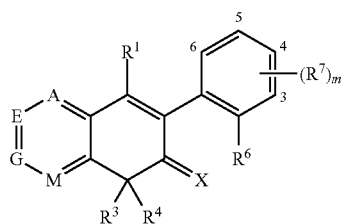

in which $R^6$ and $R^7$ are groups $R^b$ and m is zero or an integer from one to four.

9. A composition comprising a herbicidally effective amount of at least one quinolinone of the formula I or an agriculturally suitable salt thereof according to claim 1 and auxiliaries customary for formulating crop protection agents.

10. The composition according to claim 9 which comprises at least one further active compound.

11. The composition according to claim 9 which comprises two further active compounds from the group of the herbicides and/or safeners.

12. A method for controlling unwanted vegetation which comprises allowing a herbicidally effective amount of at least one quinolinone of the formula I or of an agriculturally suitable salt thereof according to claim 1 to act on plants, their seed and/or their habitat.

13. The method of claim 12, wherein X is O.

14. The method of claim 12, wherein X is S.

15. The method of claim 12, wherein X is N—$R^5$.

16. The method of claim 12, wherein $R^1$ is O—$R^4$ or O—S(O)$_n$—$R^4$.

17. The method of claim 12, wherein the compound of formula I is I.1

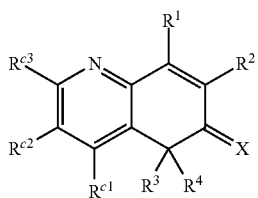

in which $R^{c1}$, $R^{c2}$ and $R^{c3}$ each correspond to a group $R^c$.

18. The method of claim 12, wherein the compound of formula I is I.2

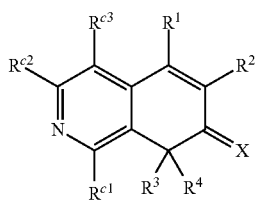

in which $R^{c1}$, $R^{c2}$ and $R^{c4}$ each correspond to a group $R^c$.

19. The method of claim 12, wherein the compound of formula I is I.A

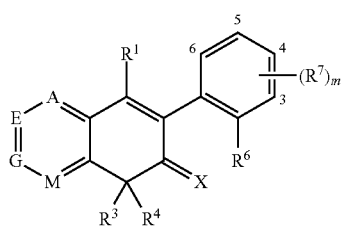

in which $R^6$ and $R^7$ are groups $R^b$ and m is zero or an integer from one to four.

* * * * *

UNITED STATES PATENT AND TRADEMARK OFFICE
CERTIFICATE OF CORRECTION

PATENT NO. : 8,329,619 B2  
APPLICATION NO. : 12/915608  
DATED : December 11, 2012  
INVENTOR(S) : Dschun Song et al.

Page 1 of 1

It is certified that error appears in the above-identified patent and that said Letters Patent is hereby corrected as shown below:

In the Claims

In Claim 1
  col. 73, line 58, after "Z-C(=O)-$R^a$," insert -- Z-$NR^i$-C(O)-$NR^iR^{ii}$ --;
  col. 74, line 52, after "$C_1$-$C_6$-alkyl," insert -- $C_1$-$C_4$-haloalkyl, --;
  col. 74, line 56, delete "$R^a2$" and insert therefore, -- $R^{a2}$ --.

Signed and Sealed this
Eighth Day of October, 2013

Teresa Stanek Rea
*Deputy Director of the United States Patent and Trademark Office*